US012781189B2

(12) United States Patent
Shepherd et al.

(10) Patent No.: US 12,781,189 B2
(45) Date of Patent: Nov. 3, 2026

(54) COMPOSITIONS AND PROCESSES FOR ENGINEERING URETERIC BUD KIDNEY TISSUES AND IN-VITRO COMPOSITIONS THEREOF

(71) Applicant: Trestle Biotherapeutics, Inc., San Diego, CA (US)

(72) Inventors: Benjamin Shepherd, Encinitas, CA (US); Alice Chen, San Diego, CA (US); J. William Higgins, III, Santee, CA (US)

(73) Assignee: Trestle Biotherapeutics, Inc., San Diego, CA (US)

( * ) Notice: Subject to any disclaimer, the term of this patent is extended or adjusted under 35 U.S.C. 154(b) by 0 days.

(21) Appl. No.: 19/285,431

(22) Filed: Jul. 30, 2025

(65) Prior Publication Data

US 2026/0098246 A1 Apr. 9, 2026

Related U.S. Application Data

(60) Provisional application No. 63/702,872, filed on Oct. 3, 2024.

(51) Int. Cl.

| | |
|---|---|
| ***C12N 5/071*** | (2010.01) |
| ***B33Y 80/00*** | (2015.01) |
| ***C12N 5/00*** | (2006.01) |

(52) U.S. Cl.

CPC ............ *C12N 5/0686* (2013.01); *B33Y 80/00* (2014.12); *C12N 5/0018* (2013.01); *C12N 2500/84* (2013.01); *C12N 2501/113* (2013.01); *C12N 2501/119* (2013.01); *C12N 2501/13* (2013.01); *C12N 2501/155* (2013.01); *C12N 2501/385* (2013.01); *C12N 2501/415* (2013.01); *C12N 2501/727* (2013.01); *C12N 2506/45* (2013.01); *C12N 2513/00* (2013.01)

(58) Field of Classification Search

CPC .. C12N 5/0686; C12N 5/0018; C12N 5/0687; B33Y 80/00

See application file for complete search history.

(56) References Cited

U.S. PATENT DOCUMENTS

| | | | |
|---|---|---|---|
| 9,242,027 | B2 | 1/2016 | Bellan |
| 9,452,239 | B2 | 9/2016 | West |
| 9,456,893 | B2 | 10/2016 | Ling |
| 9,657,261 | B2 | 5/2017 | Charest |
| 9,717,841 | B2 | 8/2017 | Mcneil |
| 9,791,433 | B2 | 10/2017 | Marx |
| 10,195,644 | B2 | 2/2019 | Boland |
| 10,767,149 | B2 | 9/2020 | Kamm |
| 10,828,399 | B2 | 11/2020 | Burdick |
| 11,214,768 | B2 | 1/2022 | Lewis |
| 11,305,038 | B2 | 4/2022 | Yoo |
| 11,559,607 | B2 | 1/2023 | Kolesky |
| 11,903,612 | B2 | 2/2024 | Ozbolat |
| 2017/0067014 | A1 | 3/2017 | Takebe |
| 2020/0063107 | A1 | 2/2020 | Kong |
| 2020/0164109 | A1 | 5/2020 | Kroll |
| 2020/0248147 | A1 | 8/2020 | Homan |
| 2020/0289709 | A1 | 9/2020 | Skylar-Scott |
| 2022/0282222 | A1 | 9/2022 | Little |
| 2026/0098246 | A1 | 4/2026 | Shepherd |

FOREIGN PATENT DOCUMENTS

| | | | |
|---|---|---|---|
| WO | 2020095423 | A1 | 5/2020 |
| WO | 2024206297 | A1 | 10/2024 |
| WO | 2026050176 | A1 | 3/2026 |

OTHER PUBLICATIONS

Constantini (Developmental Cell 18, May 18, 2010, pp. 698-712).*

Mae (2018 Biochemical and Biophysical Research Communications 495: 954-961).*

Mae (2020, Cell Reports 32, 107963).*

Nishinakamura R. Stem cells in the embryonic kidney. Kidney Int. Apr. 2008;73(8):913-7. doi: 10.1038/sj.ki.5002784.

Shi M, McCracken KW, Patel AB, Zhang W, Ester L, Valerius MT, Bonventre JV. Human ureteric bud organoids recapitulate branching morphogenesis and differentiate into functional collecting duct cell types. Nat Biotechnol. Feb. 2023;41(2):252-261.

Shi, Min, et al. "Integrating collecting systems in kidney organoids through fusion of distal nephron to ureteric bud." bioRxiv (2024).

Taguchi A, Nishinakamura R. Higher-Order Kidney Organogenesis from Pluripotent Stem Cells. Cell Stem Cell. Dec. 7, 2017;21(6):730-746.e6. doi: 10.1016/j.stem.2017.10.011.

International Search Report issued Jun. 24, 2026 for International Application No. PCT/US25/049481, 7 pages.

Kim, Kyeongseok, et al. "Improved isolation and culture of urine-derived stem cells (USCs) and enhanced production of immune cells from the USC-derived induced pluripotent stem cells." Journal of Clinical Medicine 9.3 (2020): 827.

Porter, Catherine M., et al. "Highly parallel production of designer organoids by mosaic patterning of progenitors." Cell systems 15.7 (2024): 649-661.

* cited by examiner

*Primary Examiner* — Valarie E Bertoglio

(74) *Attorney, Agent, or Firm* — Greenberg Traurig, LLP; George E. Banis

(57) ABSTRACT

This disclosure provides compositions comprising engineered ureteric bud kidney tissues and methods of making lumenized ureteric bud kidney tissues. Also provided herein are in vitro kidneys comprising nephron progenitor cells and ureteric bud cells. Methods of making the compositions and in vitro kidneys and uses thereof are disclosed herein. In some aspects, provided herein are methods for generating a lumenized kidney tissue having a spatially-controlled 3-dimensional (3D) tubular architecture in vitro.

11 Claims, 26 Drawing Sheets

Specification includes a Sequence Listing.

5 4 3 2 1

| Markers | KEY |
| --- | --- |
| MAFB-GFP | *UE: ureteric epithelium; |
| LRP2 | CS: connecting segment |
| CK8 | DT: distal tubule |
| GATA3 | PT: proximal tubule |

SEQUENCE LISTING

```
Sequence total quantity: 21
SEQ ID NO: 1            moltype = AA  length = 1114
FEATURE                 Location/Qualifiers
source                  1..1114
                        mol_type = protein
                        organism = Homo sapiens
SEQUENCE: 1
MAKATSGAAG LRLLLLLLLP LLGKVALGLY FSRDAYWEKL YVDQAAGTPL LYVHALRDAP  60
EEVPSFRLGQ HLYGTYRTRL HENNWICIQE DTGLLYLNRS LDHSSWEKLS VRNRGFPLLT  120
VYLKVFLSPT SLREGECQWP GCARVYFSFF NTSFPACSSL KPRELCFPET RPSFRIRENR  180
PPGTFHQFRL LPVQFLCPNI SVAYRLLEGE GLPFRCAPDS LEVSTRWALD REQREKYELV  240
AVCTVHAGAR EEVVMVPFPV TVYDEDDSAP TFPAGVDTAS AVVEFKRKED TVVATLRVFD  300
ADVVPASGEL VRRYTSTLLP GDTWAQQTFR VEHWPNETSV QANGSFVRAT VHDYRLVLNR  360
NLSISENRTM QLAVLVNDSD FQGPGAGVLL LHFNVSVLPV SLHLPSTYSL SVSRRARRFA  420
QIGKVCVENC QAFSGINVQY KLHSSGANCS TLGVVTSAED TSGILFVNDT KALRRPKCAE  480
LHYMVVATDQ QTSRQAQAQL LVTVEGSYVA EEAGCPLSCA VSKRRLECEE CGGLGSPTGR  540
CEWRQGDGKG ITRNFSTCSP STKTCPDGHC DVVETQDINI CPQDCLRGSI VGGHEPGEPR  600
GIKAGYGTCN CFPEEEKCFC EPEDIQDPLC DELCRTVIAA AVLFSFIVSV LLSAFCIHCY  660
HKFAHKPPIS SAEMTFRRPA QAFPVSYSSS GARRPSLDSM ENQVSVDAFK ILEDPKWEFP  720
RKNLVLGKTL GEGEFGKVVK ATAFHLKGRA GYTTVAVKML KENASPSELR DLLSEFNVLK  780
QVNHPHVIKL YGACSQDGPL LLIVEYAKYG SLRGFLRESR KVGPGYLGSG GSRNSSSLDH  840
PDERALTMGD LISFAWQISQ GMQYLAEMKL VHRDLAARNI LVAEGRKMKI SDFGLSRDVY  900
EEDSYVKRSQ GRIPVKWMAI ESLFDHIYTT QSDVWSFGVL LWEIVTLGGN PYPGIPPERL  960
FNLLKTGHRM ERPDNCSEEM YRLMLQCWKQ EPDKRPVFAD ISKDLEKMMV KRRDYLDLAA  1020
STPSDSLIYD DGLSEEETPL VDCNNAPLPR ALPSTWIENK LYGMSDPNWP GESPVPLTRA  1080
DGTNTGFPRY PNDSVYANWM LSPSAAKLMD TFDS                              1114

SEQ ID NO: 2            moltype = AA  length = 511
FEATURE                 Location/Qualifiers
source                  1..511
                        mol_type = protein
                        organism = Homo sapiens
SEQUENCE: 2
MNGVSWSQDL QEGISAWFGP PASTPASTMS IRVTQKSYKV STSGPRAFSS RSYTSGPGSR  60
ISSSSFSRVG SSNFRGGLGG GYGGASGMGG ITAVTVNQSL LSPLVLEVDP NIQAVRTQEK  120
EQIKTLNNKF ASFIDKVRFL EQQNKMLETK WSLLQQQKTA RSNMDNMFES YINNLRRQLE  180
TLGQEKLKLE AELGNMQGLV EDFKNKYEDE INKRTEMENE FVLIKKDVDE AYMNKVELES  240
```

```
RLEGLTDEIN FLRQLYEEEI RELQSQISDT SVVLSMDNSR SLDMDSIIAE VKAQYEDIAN  300
RSRAEAESMY QIKYEELQSL AGKHGDDLRR TKTEISEMNR NISRLQAEIE GLKGQRASLE  360
AAIADAEQRG ELAIKDANAK LSELEAALQR AKQDMARQLR EYQELMNVKL ALDIEIATYR  420
KLLEGEESRL ESGMQNMSIH TKTTSGYAGG LSSAYGGLTS PGLSYSLGSS FGSGAGSSSF  480
SRTSSSRAVV VKKIETRDGK LVSESSDVLP K                                511

SEQ ID NO: 3            moltype = AA  length = 509
FEATURE                 Location/Qualifiers
source                  1..509
                        mol_type = protein
                        organism = Homo sapiens
SEQUENCE: 3
MNLLDPFMKM TDEQEKGLSG APSPTMSEDS AGSPCPSGSG SDTENTRPQE NTFPKGEPDL  60
KKESEEDKFP VCIREAVSQV LKGYDWTLVP MPVRVNGSSK NKPHVKRPMN AFMVWAQAAR  120
RKLADQYPHL HNAELSKTLG KLWRLLNESE KRPFVEEAER LRVQHKKDHP DYKYQPRRRK  180
SVKNGQAEAE EATEQTHISP NAIFKALQAD SPHSSSGMSE VHSPGEHSGQ SQGPPTPPTT  240
PKTDVQPGKA DLKREGRPLP EGGRQPPIDF RDVDIGELSS DVISNIETFD VNEFDQYLPP  300
NGHPGVPATH GQVTYTGSYG ISSTAATPAS AGHVWMSKQQ APPPPPQQPP QAPPAPQAPP  360
QPQAAPPQQP AAPPQQPQAH TLTTLSSEPG QSQRTHIKTE QLSPSHYSEQ QQHSPQQIAY  420
SPFNLPHYSP SYPPITRSQY DYTDHQNSSS YYSHAAGQGT GLYSTFTYMN PAQRPMYTPI  480
ADTSGVPSIP QTHSPQHWEQ PVYTQLTRP                                   509

SEQ ID NO: 4            moltype = AA  length = 356
FEATURE                 Location/Qualifiers
source                  1..356
                        mol_type = protein
                        organism = Homo sapiens
SEQUENCE: 4
MSIPLPLLQI YTSDNYTEEM GSGDYDSMKE PCFREENANF NKIFLPTIYS IIFLTGIVGN  60
GLVILVMGYQ KKLRSMTDKY RLHLSVADLL FVITLPFWAV DAVANWYFGN FLCKAVHVIY  120
TVNLYSSVLI LAFISLDRYL AIVHATNSQR PRKLLAEKVV YVGVWIPALL LTIPDFIFAN  180
VSEADDRYIC DRFYPNDLWV VVFQFQHIMV GLILPGIVIL SCYCIIISKL SHSKGHQKRK  240
ALKTTVILIL AFFACWLPYY IGISIDSFIL LEIIKQGCEF ENTVHKWISI TEALAFFHCC  300
LNPILYAFLG AKFKTSAQHA LTSVSRGSSL KILSKGKRGG HSSVSTESES SSFHSS     356

SEQ ID NO: 5            moltype = AA  length = 976
FEATURE                 Location/Qualifiers
source                  1..976
                        mol_type = protein
                        organism = Homo sapiens
SEQUENCE: 5
MRGARGAWDF LCVLLLLLRV QTGSSQPSVS PGEPSPPSIH PGKSDLIVRV GDEIRLLCTD  60
PGFVKWTFEI LDETNENKQN EWITEKAEAT NTGKYTCTNK HGLSNSIYVF VRDPAKLFLV  120
DRSLYGKEDN DTLVRCPLTD PEVTNYSLKG CQGKPLPKDL RFIPDPKAGI MIKSVKRAYH  180
RLCLHCSVDQ EGKSVLSEKF ILKVRPAFKA VPVVSVSKAS YLLREGEEFT VTCTIKDVSS  240
SVYSTWKREN SQTKLQEKYN SWHHGDFNYE RQATLTISSA RVNDSGVFMC YANNTFGSAN  300
VTTTLEVVDK GFINIFPMIN TTVFVNDGEN VDLIVEYEAF PKPEHQQWIY MNRTFTDKWE  360
DYPKSENESN IRYVSELHLT RLKGTEGGTY TFLVSNSDVN AAIAFNVYVN TKPEILTYDR  420
LVNGMLQCVA AGFPEPTIDW YFCPGTEQRC SASVLPVDVQ TLNSSGPPFG KLVVQSSIDS  480
SAFKHNGTVE CKAYNDVGKT SAYFNFAFKG NNKEQIHPHT LFTPLLIGFV IVAGMMCIIV  540
MILTYKYLQK PMYEVQWKVV EEINGNNYVY IDPTQLPYDH KWEFPRNRLS FGKTLGAGAF  600
GKVVEATAYG LIKSDAAMTV AVKMLKPSAH LTEREALMSE LKVLSYLGNH MNIVNLLGAC  660
TIGGPTLVIT EYCCYGDLLN FLRRKRDSFI CSKQEDHAEA ALYKNLLHSK ESSCSDSTNE  720
YMDMKPGVSY VVPTKADKRR SVRIGSYIER DVTPAIMEDD ELALDLEDLL SFSYQVAKGM  780
AFLASKNCIH RDLAARNILL THGRITKICD FGLARDIKND SNYVVKGNAR LPVKWMAPES  840
IFNCVYTFES DVWSYGIFLW ELFSLGSSPY PGMPVDSKFY KMIKEGFRML SPEHAPAEMY  900
DIMKTCWDAD PLKRPTFKQI VQLIEKQISE STNHIYSNLA NCSPNRQKPV VDHSVRINSV  960
GSTASSSQPL LVHDDV                                                 976

SEQ ID NO: 6            moltype = AA  length = 444
FEATURE                 Location/Qualifiers
source                  1..444
                        mol_type = protein
                        organism = Homo sapiens
SEQUENCE: 6
MEVTADQPRW VSHHHPAVLN GQHPDTHHPG LSHSYMDAAQ YPLPEEVDVL FNIDGQGNHV  60
PPYYGNSVRA TVQRYPPTHH GSQVCRPPLL HGSLPWLDGG KALGSHHTAS PWNLSPFSKT  120
SIHHGSPGPL SVYPPASSSS LSGGHASPHL FTFPPTPPKD VSPDPSLSTP GSAGSARQDE  180
KECLKYQVPL PDSMKLESSH SRGSMTALGG ASSSTHHPIT TYPPYVPEYS SGLFPPSSLL  240
GGSPTGFGCK SRPKARSSTE GRECVNCGAT STPLWRRDGT GHYLCNACGL YHKMNGQNRP  300
LIKPKRRLSA ARRAGTSCAN CQTTTTTLWR RNANGDPVCN ACGLYYKLHN INRPLTMKKE  360
GIQTRNRKMS SKSKKCKKVH DSLEDFPKNS SFNPAALSRH MSSLSHISPF SHSSHMLTTP  420
TPMHPPSSLS FGPHHPSSMV TAMG                                        444

SEQ ID NO: 7            moltype = AA  length = 217
FEATURE                 Location/Qualifiers
source                  1..217
                        mol_type = protein
                        organism = Homo sapiens
```

```
SEQUENCE: 7
MSSLYYANTL FSKYPASSSV FATGAFPEQT SCAFASNPQR PGYGAGSGAS FAASMQGLYP  60
GGGGMAGQSA AGVYAAGYGL EPSSFNMHCA PFEQNLSGVC PGDSAKAAGA KEQRDSDLAA  120
ESNFRIYPWM RSSGTDRKRG RQTYTRYQTL ELEKEFHYNR YLTRRRRIEI AHTLCLTERQ  180
IKIWFQNRRM KWKKENKTAG PGTTGQDRAE AEEEEEE                           217

SEQ ID NO: 8           moltype = AA  length = 169
FEATURE                Location/Qualifiers
source                 1..169
                       mol_type = protein
                       organism = Homo sapiens
SEQUENCE: 8
MFQPAPKRCF TIESLVAKDS PLPASRSEDP IRPAALSYAN SSPINPFLNG FHSAAAAAAG  60
RGVYSNPDLV FAEAVSHPPN PAVPVHPVPP PHALAAHPLP SSHSPHPLFA SQQRDPSTFY  120
PWLIHRYRYL GHRFQGKSMV SEPKNKVQKA EAGGRRLRFA TKEKRDAPY              169

SEQ ID NO: 9           moltype = AA  length = 417
FEATURE                Location/Qualifiers
source                 1..417
                       mol_type = protein
                       organism = Homo sapiens
SEQUENCE: 9
MDMHCKADPF SAMHPGHGGV NQLGGVFVNG RPLPDVVRQR IVELAHQGVR PCDISRQLRV  60
SHGCVSKILG RYYETGSIKP GVIGGSKPKV ATPKVVDKIA EYKRQNPTMF AWEIRDRLLA  120
EGICDNDTVP SVSSINRIIR TKVQQPFHPT PDGAGTGVTA PGHTIVPSTA SPPVSSASND  180
PVGSYSINGI LGIPRSNGEK RKRDEVEVYT DPAHIRGGGG LHLVWTLRDV SEGSVPNGDS  240
QSGVDSLRKH LRADTFTQQQ LEALDRVFER PSYPDVFQAS EHIKSEQGNE YSLPALTPGL  300
DEVKSSLSAS TNPELGSNVS GTQTYPVVTG RDMASTTLPG YPPHVPPTGQ GSYPTSTLAG  360
MVPGSEFSGN PYSHPQYTAY NEAWRFSNPA LLSSPYYYSA APRGSAPAAA AAYDRH      417

SEQ ID NO: 10          moltype = AA  length = 354
FEATURE                Location/Qualifiers
source                 1..354
                       mol_type = protein
                       organism = Homo sapiens
SEQUENCE: 10
MRARPQVCEA LLFALALQTG VCYGIKWLAL SKTPSALALN QTQHCKQLEG LVSAQVQLCR  60
SNLELMHTVV HAAREVMKAC RRAFADMRWN CSSIELAPNY LLDLERGTRE SAFVYALSAA  120
AISHAIARAC TSGDLPGCSC GPVPGEPPGP GNRWGGCADN LSYGLLMGAK FSDAPMKVKK  180
TGSQANKLMR LHNSEVGRQA LRASLEMKCK CHGVSGSCSI RTCWKGLQEL QDVAADLKTR  240
YLSATKVVHR PMGTRKHLVP KDLDIRPVKD SELVYLQSSP DFCMKNEKVG SHGTQDRQCN  300
KTSNGSDSCD LMCCGRGYNP YTDRVVERCH CKYHWCCYVT CRRCERTVER YVCK        354

SEQ ID NO: 11          moltype = AA  length = 882
FEATURE                Location/Qualifiers
source                 1..882
                       mol_type = protein
                       organism = Homo sapiens
SEQUENCE: 11
MGPWSRSLSA LLLLLQVSSW LCQEPEPCHP GFDAESYTFT VPRRHLERGR VLGRVNFEDC  60
TGRQRTAYFS LDTRFKVGTD GVITVKRPLR FHNPQIHFLV YAWDSTYRKF STKVTLNTVG  120
HHHRPPPHQA SVSGIQAELL TFPNSSPGLR RQKRDWVIPP ISCPENEKGP FPKNLVQIKS  180
NKDKEGKVFY SITGQGADTP PVGVFIIERE TGWLKVTEPL DRERIATYTL FSHAVSSNGN  240
AVEDPMEILI TVTDQNDNKP EFTQEVFKGS VMEGALPGTS VMEVTATDAD DDVNTYNAAI  300
AYTILSQDPE LPDKNMFTIN RNTGVISVVT TGLDRESFPT YTLVVQAADL QGEGLSTTAT  360
AVITVTDTND NPPIFNPTTY KGQVPENEAN VVITTLKVTD ADAPNTPAWE AVYTILNDDG  420
GQFVVTTNPV NNDGILKTAK GLDFEAKQQY ILHVAVTNVV PFEVSLTTST ATVTVDVLDV  480
NEAPIFVPPE KRVEVSEDFG VGQEITSYTA QEPDTFMEQK ITYRIWRDTA NWLEINPDTG  540
AISTRAELDR EDFEHVKNST YTALIIATDN GSPVATGTGT LLLILSDVND NAPIPEPRTI  600
FFCERNPKPQ VINIIDADLP PNTSPFTAEL THGASANWTI QYNDPTQESI ILKPKMALEV  660
GDYKINLKLM DNQNKDQVTT LEVSVCDCEG AAGVCRKAQP VEAGLQIPAI LGILGGILAL  720
LILILLLLLF LRRRAVVKEP LLPPEDDTRD NVYYYDEEGG GEEDQDFDLS QLHRGLDARP  780
EVTRNDVAPT LMSVPRYLPR PANPDEIGNF IDENLKAADT DPTAPPYDSL LVFDYEGSGS  840
EAASLSSLNS SESDKDQDYD YLNEWGNRFK KLADMYGGGE DD                     882

SEQ ID NO: 12          moltype = AA  length = 425
FEATURE                Location/Qualifiers
source                 1..425
                       mol_type = protein
                       organism = Homo sapiens
SEQUENCE: 12
MVSKLTSLQQ ELLSALLSSG VTKEVLVQAL EELLPSPNFG VKLETLPLSP GSGAEPDTKP  60
VFHTLTNGHA KGRLSGDEGS EDGDDYDTPP ILKELQALNT EEAAEQRAEV DRMLSEDPWR  120
AAKMIKGYMQ QHNIPQREVV DVTGLNQSHL SQHLNKGTPM KTQKRAALYT WYVRKQREIL  180
RQFNQTVQSS GNMTDKSSQD QLLFLFPEFS QQSHGPGQSD DACSEPTNKK MRRNRFKWGP  240
ASQQILYQAY DRQKNPSKEE REALVEECNR AECLQRGVSP SKAHGLGSNL VTEVRVYNWF  300
ANRRKEEAFR QKLAMDAYSS NQTHSLNPLL SHGSPHHQPS SSPPNKLSGV RYSQQGNNEI  360
TSSSTISHHG NSAMVTSQSV LQQVSPASLD PGHNLLSPDG KMDLSLRRRF APSQHLDEYP  420
QPLPP                                                              425
```

```
SEQ ID NO: 13           moltype = AA  length = 291
FEATURE                 Location/Qualifiers
source                  1..291
                        mol_type = protein
                        organism = Homo sapiens
SEQUENCE: 13
MSMLPTFGFT QEQVACVCEV LQQGGNIERL GRFLWSLPAC EHLHKNESVL KAKAVVAFHR  60
GNFRELYKIL ESHQFSPHNH AKLQQLWLKA HYIEAEKLRG RPLGAVGKYR VRRKFPLPRS  120
IWDGEETSYC FKEKSRSVLR EWYAHNPYPS PREKRELAEA TGLTTTQVSN WFKNRRQRDR  180
AAEAKERENN ENSNSNSHNP LNGSGKSVLG SSEDEKTPSG TPDHSSSSPA LLLSPPPPGL  240
PSLHSLGHPP GPSAVPVPVP GGGGADPLQH HHGLQDSILN PMSANLVDLG S           291

SEQ ID NO: 14           moltype = AA  length = 193
FEATURE                 Location/Qualifiers
source                  1..193
                        mol_type = protein
                        organism = Homo sapiens
SEQUENCE: 14
MPTTSRPALD VKGGTSPAKE DANQEMSSVA YSNLAVKDRK AVAILHYPGV ASNGTKASGA  60
PTSSSGSPIG SPTTTPPTKP PSFNLHPAPH LLASMHLQKL NSQYQGMAAA TPGQPGEAGP  120
LQNWDFGAQA GGAESLSPSA GAQSPAIIDS DPVDEEVLMS LVVELGLDRA NELPELWLGQ  180
NEFDFTADFP SSC                                                    193

SEQ ID NO: 15           moltype = AA  length = 4655
FEATURE                 Location/Qualifiers
source                  1..4655
                        mol_type = protein
                        organism = Homo sapiens
SEQUENCE: 15
MDRGPAAVAC TLLLALVACL APASGQECDS AHFRCGSGHC IPADWRCDGT KDCSDDADEI  60
GCAVVTCQQG YFKCQSEGQC IPNSWVCDQD QDCDDGSDER QDCSQSTCSS HQITCSNGQC  120
IPSEYRCDHV RDCPDGADEN DCQYPTCEQL TCDNGACYNT SQKCDWKVDC RDSSDEINCT  180
EICLHNEFSC GNGECIPRAY VCDHDNDCQD GSDEHACNYP TCGGYQFTCP SGRCIYQNWV  240
CDGEDDCKDN GDEDGCESGP HDVHKCSPRE WSCPESGRCI SIYKVCDGIL DCPGREDENN  300
TSTGKYCSMT LCSALNCQYQ CHETPYGGAC FCPPGYIINH NDSRTCVEFD DCQIWGICDQ  360
KCESRPGRHL CHCEEGYILE RGQYCKANDS FGEASIIFSN GRDLLIGDIH GRSFRILVES  420
QNRGVAVGVA FHYHLQRVFW TDTVQNKVFS VDINGLNIQE VLNVSVETPE NLAVDWVNNK  480
IYLVETKVNR IDMVNLDGSY RVTLITENLG HPRGIAVDPT VGYLFFSDWE SLSGEPKLER  540
AFMDGSNRKD LVKTKLGWPA GVTLDMISKR VYWVDSRFDY IETVTYDGIQ RKTVVHGGSL  600
IPHPFGVSLF EGQVFFTDWT KMAVLKANKF TETNPQVYYQ ASLRPYGVTV YHSLRQPYAT  660
NPCKDNNGGC EQVCVLSHRT DNDGLGFRCK CTFGFQLDTD ERHCIAVQNF LIFSSQVAIR  720
GIPFTLSTQE DVMVPVSGNP SFFVGIDFDA QDSTIFFSDM SKHMIFKQKI DGTGREILAA  780
NRVENVESLA FDWISKNLYW TDSHYKSISV MRLADKTRRT VVQYLNNPRS VVVHPFAGYL  840
FFTDWFRPAK IMRAWSDGSH LLPVINTTLG WPNGLAIDWA ASRLYWVDAY FDKIEHSTFD  900
GLDRRRLGHI EQMTHPFGLA IFGEHLFFTD WRLGAIIRVR KADGGEMTVI RSGIAYILHL  960
KSYDVNIQTG SNACNQPTHP NGDCSHFCFP VPNFQRVCGC PYGMRLASNH LTCEGDPTNE  1020
PPTEQCGLFS FPCKNGRCVP NYYLCDGVDD CHDNSDEQLC GTLNNTCSSS AFTCGHGECI  1080
PAHWRCDKRN DCVDGSDEHN CPTHAPASCL DTQYTCDNHQ CISKNWVCDT DNDCGDGSDE  1140
KNCNSTETCQ PSQFNCPNHR CIDLSFVCDG DKDCVDGSDE VGCVLNCTAS QFKCASGDKC  1200
IGVTNRCDGV FDCSDNSDEA GCPTRPPGMC HSDEFQCQED GICIPNFWEC DGHPDCLYGS  1260
DEHNACVPKT CPSSYFHCDN GNCIHRAWLC DRDNDCGDMS DEKDCPTQPF RCPSWQWQCL  1320
GHNICVNLSV VCDGIFDCPN GTDESPLCNG NSCSDFNGGC THECVQEPFG AKCLCPLGFL  1380
LANDSKTCED IDECDILGSC SQHCYNMRGS FRCSCDTGYM LESDGRTCKV TASESLLLLV  1440
ASQNKIIADS VTSQVHNIYS LVENGSYIVA VDFDSISGRI FWSDATQGKT WSAFQNGTDR  1500
RVVFDSSIIL TETIAIDWVG RNLYWTDYAL ETIEVSKIDG SHRTVLISKN LTNPRGLALD  1560
PRMNEHLLFW SDWGHHPRIE RASMDGSMRT VIVQDKIFWP CGLTIDYPNR LLYFMDSYLD  1620
YMDFCDYNGH HRRQVIASDL IIRHPYALTL FEDSVYWTDR ATRRVMRANK WHGGNQSVVM  1680
YNIQWPLGIV AVHPSKQPNS VNPCAFSRCS HLCLLSSQGP HFYSCVCPSG WSLSPDLLNC  1740
LRDDQPFLIT VRQHIIFGIS LNPEVKSNDA MVPIAGIQNG LDVEFDDAEQ YIYWVENPGE  1800
IHRVKTDGTN RTVFASISMV GPSMNLALDW ISRNLYSTNP RTQSIEVLTL HGDIRYRKTL  1860
IANDGTALGV GFPIGITVDP ARGKLYWSDQ GTDSGVPAKI ASANMDGTSV KTLFTGNLEH  1920
LECVTLDIEE QKLYWAVTGR GVIERGNVDG TDRMILVHQL SHPWGIAVHD SFLYYTDEQY  1980
EVIERVDKAT GANKIVLRDN VPNLRGLQVY HRRNAAESSN GCSNNMNACQ QICLPVPGGL  2040
FSCACATGFK LNPDNRSCSP YNSFIVVSML SAIRGFSLEL SDHSETMVPV AGQGRNALHV  2100
DVDVSSGFIY WCDFSSSVAS DNAIRRIKPD GSSLMNIVTH GIGENGVRGI AVDWVAGNLY  2160
FTNAFVSETL IEVLRINTTY RRVLLKVTVD MPRHIVVDPK NRYLFWADYG QRPKIERSFL  2220
DCTNRTVLVS EGIVTPRGLA VDRSDGYVYW VDDSLDIIAR IRINGENSEV IRYGSRYPTP  2280
YGITVFENSI IWVDRNLKKI FQASKEPENT EPPTVIRDNI NWLRDVTIFD KQVQPRSPAE  2340
VNNNPCLENN GGCSHLCFAL PGLHTPKCDC AFGTLQSDGK NCAISTENFL IFALSNSLRS  2400
LHLDPENHSP PFQTINVERT VMSLDYDSVS DRIYFTQNLA SGVGQISYAT LSSGIHTPTV  2460
IASGIGTADG IAFDWITRRI YYSDYLNQMI NSMAEDGSNR TVIARVPKPR AIVLDPCQGY  2520
LYWADWDTHA KIERATLGGN FRVPIVNSSL VMPSGLTLDY EEDLLYWVDA SLQRIERSTL  2580
TGVDREVIVN AAVHAFGLTL YGQYIYWTDL YTQRIYRANK YDGSGQIAMT TNLLSQPRGI  2640
NTVVKNQKQQ CNNPCEQFNG GCSHICAPGP NGAECQCPHE GNWYLANNRK HCIVDNGERC  2700
GASSFTCSNG RCISEEWKCD NDNDCGDGSD EMESVCALHT CSPTAFTCAN GRCVQYSYRC  2760
DYYNDCGDGS DEAGCLFRDC NATTEFMCNN RRCIPREFIC NGVDNCHDNN TSDEKNCPDR  2820
TCQSGYTKCH NSNICIPRVY LCDGDNDCGD NSDENPTYCT THTCSSSEFQ CASGRCIPQH  2880
WYCDQETDCF DASDEPASCG HSERTCLADE FKCDGGRCIP SEWICDGDND CGDMSDEDKR  2940
```

```
HQCQNQNCSD SEFLCVNDRP PDRRCIPQSW VCDGDVDCTD GYDENQNCTR RTCSENEFTC  3000
GYGLCIPKIF RCDRHNDCGD YSDERGCLYQ TCQQNQFTCQ NGRCISKTFV CDEDNDCGDG  3060
SDELMHLCHT PEPTCPPHEF KCDNGRCIEM MKLCNHLDDC LDNSDEKGCG INECHDPSIS  3120
GCDHNCTDTL TSFYCSCRPG YKLMSDKRTC VDIDECTEMP FVCSQKCENV IGSYICKCAP  3180
GYLREPDGKT CRQNSNIEPY LIFSNRYYLR NLTIDGYFYS LILEGLDNVV ALDFDRVEKR  3240
LYWIDTQRQV IERMFLNKTN KETIINHRLP AAESLAVDWV SRKLYWLDAR LDGLFVSDLN  3300
GGHRRMLAQH CVDANNTFCF DNPRGLALHP QYGYLYWADW GHRAYIGRVG MDGTNKSVII  3360
STKLEWPNGI TIDYTNDLLY WADAHLGYIE YSDLEGHHRH TVYDGALPHP FAITIFEDTI  3420
YWTDWNTRTV EKGNKYDGSN RQTLVNTTHR PFDIHVYHPY RQPIVSNPCG TNNGGCSHLC  3480
LIKPGGKGFT CECPDDFRTL QLSGSTYCMP MCSSTQFLCA NNEKCIPIWW KCDGQKDCSD  3540
GSDELALCPQ RFCRLGQFQC SDGNCTSPQT LCNAHQNCPD GSDEDRLLCE NHHCDSNEWQ  3600
CANKRCIPES WQCDTFNDCE DNSDEDSSHC ASRTCRPGQF RCANGRCIPQ AWKCDVDNDC  3660
GDHSDEPIEE CMSSAHLCDN FTEFSCKTNY RCIPKWAVCN GVDDCRDNSD EQGCEERTCH  3720
PVGDFRCKNH HCIPLRWQCD GQNDCGDNSD EENCAPRECT ESEFRCVNQQ CIPSRWICDH  3780
YNDCGDNSDE RDCEMRTCHP EYFQCTSGHC VHSELKCDGS ADCLDASDEA DCPTRFPDGA  3840
YCQATMFECK NHVCIPPYWK CDGDDDCGDG SDEELHLCLD VPCNSPNRFR CDNNRCIYSH  3900
EVCNGVDDCG DGTDETEEHC RKPTPKPCTE YEYKCGNGHC IPHDNVCDDA DDCGDWSDEL  3960
GCNKGKERTC AENICEQNCT QLNEGGFICS CTAGFETNVF DRTSCLDINE CEQFGTCPQH  4020
CRNTKGSYEC VCADGFTSMS DRPGKRCAAE GSSPLLLLPD NVRIRKYNLS SERFSEYLQD  4080
EEYIQAVDYD WDPKDIGLSV VYYTVRGEGS RFGAIKRAYI PNFESGRNNL VQEVDLKLKY  4140
VMQPDGIAVD WVGRHIYWSD VKNKRIEVAK LDGRYRKWLI STDLDQPAAI AVNPKLGLMF  4200
WTDWGKEPKI ESAWMNGEDR NILVFEDLGW PTGLSIDYLN NDRIYWSDFK EDVIETIKYD  4260
GTDRRVIAKE AMNPYSLDIF EDQLYWISKE KGEVWKQNKF GQGKKEKTLV VNPWLTQVRI  4320
FHQLRYNKSV PNLCKQICSH LCLLRPGGYS CACPQGSSFI EGSTTECDAA IELPINLPPP  4380
CRCMHGGNCY FDETDLPKCK CPSGYTGKYC EMAFSKGISP GTTAVAVLLT ILLIVVIGAL  4440
AIAGFFHYRR TGSLLPALPK LPSLSSLVKP SENGNGVTFR SGADLNMDIG VSGFGPETAI  4500
DRSMAMSEDF VMEMGKQPII FENPMYSARD SAVKVVQPIQ VTVSENVDNK NYGSPINPSE  4560
IVPETNPTSP AADGTQVTKW NLFKRKSKQT TNFENPIYAQ MENEQKESVA ATPPPSPSLP  4620
AKPKPPSRRD PTPTYSATED TFKDTANLVK EDSEV                             4655

SEQ ID NO: 16          moltype = AA  length = 323
FEATURE                Location/Qualifiers
source                 1..323
                       mol_type = protein
                       organism = Homo sapiens
SEQUENCE: 16
MAAELSMGPE LPTSPLAMEY VNDFDLLKFD VKKEPLGRAE RPGRPCTRLQ PAGSVSSTPL  60
STPCSSVPSS PSFSPTEQKT HLEDLYWMAS NYQQMNPEAL NLTPEDAVEA LIGSHPVPQP  120
LQSFDSFRGA HHHHHHHHPH PHHAYPGAGV AHDELGPHAH PHHHHHHQAS PPPSSAASPA  180
QQLPTSHPGP GPHATASATA AGGNGSVEDR FSDDQLVSMS VRELNRHLRG FTKDEVIRLK  240
QKRRTLKNRG YAQSCRYKRV QQKHHLENEK TQLIQQVEQL KQEVSRLARE RDAYKVKCEK  300
LANSGFREAG STSDSPSSPE FFL                                         323

SEQ ID NO: 17          moltype = AA  length = 1241
FEATURE                Location/Qualifiers
source                 1..1241
                       mol_type = protein
                       organism = Homo sapiens
SEQUENCE: 17
MALGTTLRAS LLLLGLLTEG LAQLAIPASV PRGFWALPEN LTVVEGASVE LRCGVSTPGS  60
AVQWAKDGLL LGPDPRIPGF PRYRLEGDPA RGEFHLHIEA CDLSDDAEYE CQVGRSEMGP  120
ELVSPRVILS ILVPPKLLLL TPEAGTMVTW VAGQEYVVNC VSGDAKPAPD ITILLSGQTI  180
SDISANVNEG SQQKLFTVEA TARVTPRSSD NRQLLVCEAS SPALEAPIKA SFTVNVLFPP  240
GPPVIEWPGL DEGHVRAGQS LELPCVARGG NPLATLQWLK NGQPVSTAWG TEHTQAVARS  300
VLVMTVRPED HGAQLSCEAH NSVSAGTQEH GITLQVTFPP SAIIILGSAS QTENKNVTLS  360
CVSKSSRPRV LLRWWLGWRQ LLPMEETVMD GLHGGHISMS NLTFLARRED NGLTLTCEAF  420
SEAFTKETFK KSLILNVKYP AQKLWIEGPP EGQKLRAGTR VRLVCLAIGG NPEPSLMWYK  480
DSRTVTESRL PQESRRVHLG SVEKSGSTFS RELVLVTGPS DNQAKFTCKA GQLSASTQLA  540
VQFPPTNVTI LANASALRPG DALNLTCVSV SSNPPVNLSW DKEGERLEGV AAPPRRAPFK  600
GSAAARSVLL QVSSRDHGQR VTCRAHSAEL RETVSSFYRL NVLYRPEFLG EQVLVVTAVE  660
QGEALLPVSV SANPAPEAFN WTFRGYRLSP AGGPRHRILS SGALHLWNVT RADDGLYQLH  720
CQNSEGTAEA RLRLDVHYAP TIRALQDPTE VNVGGSVDIV CTVDANPILP GMFNWERLGE  780
DEEDQSLDDM EKISRGPTGR LRIHHAKLAQ AGAYQCIVDN GVAPPARRLL RLVVRFAPQV  840
EHPTPLTKVA AAGDSTSSAT LHCRARGVPN IVFTWTKNGV PLDLQDPRYT EHTYHQGGVH  900
SSLLTIANVS AAQDYALFTC TATNALGSDQ TNIQLVSISR PDPPSGLKVV SLTPHSVGLE  960
WKPGFDGGLP QRFCIRYEAL GTPGFHYVDV VPPQATTFTL TGLQPSTRYR VWLLASNALG  1020
DSGLADKGTQ LPITTPGLHQ PSGEPEDQLP TEPPSGPSGL PLLPVLFALG GLLLLSNASC  1080
VGGVLWQRRL RRLAEGISEK TEAGSEEDRV RNEYEESQWT GERDTQSSTV STTEAEPYYR  1140
SLRDFSPQLP PTQEEVSYSR GFTGEDEDMA FPGHLYDEVE RTYPPSGAWG PLYDEVQMGP  1200
WDLHWPEDTY QDPRGIYDQV AGDLDTLEPD SLPFELRGHL V                     1241

SEQ ID NO: 18          moltype = AA  length = 3623
FEATURE                Location/Qualifiers
source                 1..3623
                       mol_type = protein
                       organism = Homo sapiens
SEQUENCE: 18
MMNMSLPFLW SLLTLLIFAE VNGEAGELEL QRQKRSINLQ QPRMATERGN LVFLTGSAQN  60
IEFRTGSLGK IKLNDEDLSE CLHQIQKNKE DIIELKGSAI GLPQNISSQI YQLNSKLVDL  120
```

-continued

ERKFQGLQQT VDKKVCSSNP CQNGGTCLNL HDSFFCICPP QWKGPLCSAD VNECEIYSGT 180
PLSCQNGGTC VNTMGSYSCH CPPETYGPQC ASKYDDCEGG SVARCVHGIC EDLMREQAGE 240
PKYSCVCDAG WMFSPNSPAC TLDRDECSFQ PGPCSTLVQC FNTQGSFYCG ACPTGWQGNG 300
YICEDINECE INNGGCSVAP PVECVNTPGS SHCQACPPGY QGDGRVCTLT DICSVSNGGC 360
HPDASCSSTL GSLPLCTCLP GYTGNGYGPN GCVQLSNICL SHPCLNGQCI DTVSGYFCKC 420
DSGWTGVNCT ENINECLSNP CLNGGTCVDG VDSFSCECTR LWTGALCQVP QQVCGESLSG 480
INGSFSYRSP DVGYVHDVNC FWVIKTEMGK VLRITFTFFR LESMDNCPHE FLQVYDGDSS 540
SAFQLGRFCG SSLPHELLSS DNALYFHLYS EHLRNGRGFT VRWETQQPEC GGILTGPYGS 600
IKSPGYPGNY PPGRDCVWIV VTSPDLLVTF TFGTLSLEHH DDCNKDYLEI RDGPLYQDPL 660
LGKFCTTFSV PPLQTTGPFA RIHFHSDSQI SDQGFHITYL TSPSDLRCGG NYTDPEGELF 720
LPELSGPFTH TRQCVYMMKQ PQGEQIQINF THVELQCQSD SSQNYIEVRD GETLLGKVCG 780
NGTISHIKSI TNSVWIRFKI DASVEKASFR AVYQVACGDE LTGEGVIRSP FFPNVYPGER 840
TCRWTIHQPQ SQVILLNFTV FEIGSSAHCE TDYVEIGSSS ILGSPENKKY CGTDIPSFIT 900
SVYNFLYVTF VKSSSTENHG FMAKFSAEDL ACGEILTEST GTIQSPGHPN VYPHGINCTW 960
HILVQPNHLI HLMFETFHLE FHYNCTNDYL EVYDTDSETS LGRYCGKSIP PSLTSSGNSL 1020
MLVFVTDSDL AYEGFLINYE AISAATACLQ DYTDDLGTFT SPNFPNNYPN NWECIYRITV 1080
RTGQLIAVHF TNFSLEEAIG NYYTDFLEIR DGGYEKSPLL GIFYGSNLPP TIISHSNKLW 1140
LKFKSDQIDT RSGFSAYWDG SSTGCGGNLT TSSGTFISPN YPMPYYHSSE CYWWLKSSHG 1200
SAFELEFKDF HLEHHPNCTL DYLAVYDGPS SNSHLLTQLC GDEKPPLIRS SGDSMFIKLR 1260
TDEGQQGRGF KAEYRQTCEN VVIVNQTYGI LESIGYPNPY SENQHCNWTI RATTGNTVNY 1320
TFLAFDLEHH INCSTDYLEL YDGPRQMGRY CGVDLPPPGS TTSSKLQVLL LTDGVGRREK 1380
GFQMQWFVYG CGGELSGATG SFSSPGFPNR YPPNKECIWY IRTDPGSSIQ LTIHDFDVEY 1440
HSRCNFDVLE IYGGPDFHSP RIAQLCTQRS PENPMQVSST GNELAIRFKT DLSINGRGFN 1500
ASWQAVTGGC GGIFQAPSGE IHSPNYPSPY RSNTDCSWVI RVDRNHRVLL NFTDFDLEPQ 1560
DSCIMAYDGL SSTMSRLART CGREQLANPI VSSGNSLFLR FQSGPSRQNR GFRAQFRQAC 1620
GGHILTSSFD TVSSPRFPAN YPNNQNCSWI IQAQPPLNHI TLSFTHFELE RSTTCARDFV 1680
EILDGGHEDA PLRGRYCGTD MPHPITSFSS ALTLRFVSDS SISAGGFHTT VTASVSACGG 1740
TFYMAEGIFN SPGYPDIYPP NVECVWNIVS SPGNRLQLSF ISFQLEDSQD CSRDFVEIRE 1800
GNATGHLVGR YCGNSFPLNY SSIVGHTLWV RFISDGSGSG TGFQATFMKI FGNDNIVGTH 1860
GKVASPFWPE NYPHNSNYQW TVNVNASHVV HGRILEMDIE EIQNCYYDKL RIYDGPSIHA 1920
RLIGAYCGTQ TESFSSTGNS LTFHFYSDSS ISGKGFLLEW FAVDAPDGVL PTIAPGACGG 1980
FLRTGDAPVF LFSPGWPDSY SNRVDCTWLI QAPDSTVELN ILSLDIESHR TCAYDSLVIR 2040
DGDNNLAQQL AVLCGREIPG PIRSTGEYMF IRFTSDSSVT RAGFNASFHK SCGGYLHADR 2100
GIITSPKYPE TYPSNLNCSW HVLVQSGLTI AVHFEQPFQI PNGDSSCNQG DYLVLRNGPD 2160
ICSPPLGPPG GNGHFCGSHA SSTLFTSDNQ MFVQFISDHS NEGQGFKIKY EAKSLACGGN 2220
VYIHDADSAG YVTSPNHPHN YPPHADCIWI LAAPPETRIQ LQFEDRFDIE VTPNCTSNYL 2280
ELRDGVDSDA PILSKFCGTS LPSSQWSSGE VMYLRFRSDN SPTHVGFKAK YSIAQCGGRV 2340
PGQSGVVESI GHPTLPYRDN LFCEWHLQGL SGHYLTISFE DFNLQNSSGC EKDFVEIWDN 2400
HTSGNILGRY CGNTIPDSID TSSNTAVVRF VTDGSVTASG FRLRFESSME ECGGDLQGSI 2460
GTFTSPNYPN PNPHGRICEW RITAPEGRRI TLMFNNLRLA THPSCNNEHV IVFNGIRSNS 2520
PQLEKLCSSV NVSNEIKSSG NTMKVIFFTD GSRPYGGFTA SYTSSEDAVC GGSLPNTPEG 2580
NFTSPGYDGV RNYSRNLNCE WTLSNPNQGN SSISIHFEDF YLESHQDCQF DVLEFRVGDA 2640
DGPLMWRLCG PSKPTLPLVI PYSQVWIHFV TNERVEHIGF HAKYSFTDCG GIQIGDSGVI 2700
TSPNYPNAYD SLTHCSSLLE APQGHTITLT FSDFDIEPHT TCAWDSVTVR NGGSPESPII 2760
GQYCGNSNPR TIQSGSNQLV VTFNSDHSLQ GGGFYATWNT QTLGCGGIFH SDNGTIRSPH 2820
WPQNFPENSR CSWTAITHKS KHLEISFDNN FLIPSGDGQC QNSFVKVWAG TEEVDKALLA 2880
TGCGNVAPGP VITPSNTFTA VFQSQEAPAQ GFSASFVSRC GSNFTGPSGY IISPNYPKQY 2940
DNNMNCTYVI EANPLSVVLL TFVSFHLEAR SAVTGSCVND GVHIIRGYSV MSTPFATVCG 3000
DEMPAPLTIA GPVLLNFYSN EQITDFGFKF SYRIISCGGV FNFSSGIITS PAYSYADYPN 3060
DMHCLYTITV SDDKVIELKF SDFDVVPSTS CSHDYLAIYD GANTSDPLLG KFCGSKRPPN 3120
VKSSNNSMLL VFKTDSFQTA KGWKMSFRQT LGPQQGCGGY LTGSNNTFAS PDSDSNGMYD 3180
KNLNCVWIII APVNKVIHLT FNTFALEAAS TRQRCLYDYV KLYDGDSENA NLAGTFCGST 3240
VPAPFISSGN FLTVQFISDL TLEREGFNAT YTIMDMPCGG TYNATWTPQN ISSPNSSDPD 3300
VPFSICTWVI DSPPHQQVKI TVWALQLTSQ DCTQNYLQLQ DSPQGHGNSR FQFCGRNASA 3360
VPVFYSSMST AMVIFKSGVV NRNSRMSFTY QIADCNRDYH KAFGNLRSPG WPDNYDNDKD 3420
CTVTLTAPQN HTISLFFHSL GIENSVECRN DFLEVRNGSN SNSPLLGKYC GTLLPNPVFS 3480
QNNELYLRFK SDSVTSDRGY EIIWTSSPSG CGGTLYGDRG SFTSPGYPGT YPNNTYCEWV 3540
LVAPAGRLVT INFYFISIDD PGDCVQNYLT LYDGPNASSP SSGPYCGGDT SIAPFVASSN 3600
QVFIKFHADY ARRPSAFRLT WDS 3623

SEQ ID NO: 19 moltype = AA length = 1099
FEATURE Location/Qualifiers
source 1..1099
mol_type = protein
organism = Homo sapiens
SEQUENCE: 19
MSLNNSSNVF LDSVPSNTNR FQVSVINENH ESSAAADDNT DPPHYEETSF GDEAQKRLRI 60
SFRPGNQECY DNFLQSGETA KTDASFHAYD SHTNTYYLQT FGHNTMDAVP KIEYYRNTGS 120
ISGPKVNRPS LLEIHEQLAK NVAVTPSSAD RVANGDGIPG DEQAENKEDD QAGVVKFGWV 180
KGVLVRCMLN IWGVMLFIRL SWIVGEAGIG LGVLIILLST MVTSITGLST SAIATNGFVR 240
GGGAYYLISR SLGPEFGGSI GLIFAFANAV AVAMYVVGFA ETVVDLLKES DSMMVDPTND 300
IRIIGSITVV ILLGISVAGM EWEAKAQVIL LVILLIAIAN FFIGTVIPSN NEKKSRGFFN 360
YQASIFAENF GPRFTKGEGF FSVFAIFFPA ATGILAGANI SGDLEDPQDA IPRGTMLAIF 420
ITTVAYLGVA ICVGACVVRD ATGNMNDTII SGMNCNGSAA CGLGYDFSRC RHEPCQYGLM 480
NNFQVMSMVS GFGPLITAGI FSATLSSALA SLVSAPKVFQ ALCKDNIYKA LQFFAKGYGK 540
NNEPLRGYIL TFLIAMAFIL IAELNTIAPI ISNFFLASYA LINFSCFHAS YAKSPGWRPA 600
YGIYNMWVSL FGAVLCCAVM FVINWWAAVI TYVIEFFLYV YVTCKKPDVN WGSSTQALSY 660
VSALDNALEL TTVEDHVKNF RPQCIVLTGG PMTRPALLDI THAFTKNSGL CICCEVFVGP 720
RKLCVKEMNS GMAKKQAWLI KNKIKAFYAA VAADCFRDGV RSLLQASGLG RMKPNTLVIG 780

-continued

```
YKKNWRKAPL TEIENYVGII HDAFDFEIGV VIVRISQGFD ISQVLQVQEE LERLEQERLA  840
LEATIKDNEC EEESGGIRGL FKKAGKLNIT KTTPKKDGSI NTSQSMHVGE FNQKLVEAST  900
QFKKKQEKGT IDVWWLFDDG GLTLLIPYIL TLRKKWKDCK LRIYVGGKIN RIEEEKIVMA  960
SLLSKFRIKF ADIHIIGDIN IRPNKESWKV FEEMIEPYRL HESCKDLTTA EKLKRETPWK  1020
ITDAELEAVK EKSYRQVRLN ELLQEHSRAA NLIVLSLPVA RKGSISDLLY MAWLEILTKN  1080
LPPVLLVRGN HKNVLTFYS                                              1099

SEQ ID NO: 20          moltype = AA  length = 464
FEATURE                Location/Qualifiers
source                 1..464
                       mol_type = protein
                       organism = Homo sapiens
SEQUENCE: 20
MRLSKTLVDM DMADYSAALD PAYTTLEFEN VQVLTMGNDT SPSEGTNLNA PNSLGVSALC  60
AICGDRATGK HYGASSCDGC KGFFRRSVRK NHMYSCRFSR QCVVDKDKRN QCRYCRLKKC  120
FRAGMKKEAV QNERDRISTR RSSYEDSSLP SINALLQAEV LSRQITSPVS GINGDIRAKK  180
IASIADVCES MKEQLLVLVE WAKYIPAFCE LPLDDQVALL RAHAGEHLLL GATKRSMVFK  240
DVLLLGNDYI VPRHCPELAE MSRVSIRILD ELVLPFQELQ IDDNEYAYLK AIIFFDPDAK  300
GLSDPGKIKR LRSQVQVSLE DYINDRQYDS RGRFGELLLL LPTLQSITWQ MIEQIQFIKL  360
FGMAKIDNLL QEMLLGGSPS DAPHAHHPLH PHLMQEHMGT NVIVANTMPT HLSNGQMSTP  420
ETPQPSPPGG SGSEPYKLLP GAVATIVKPL SAIPQPTITK QEVI                  464

SEQ ID NO: 21          moltype = AA  length = 1063
FEATURE                Location/Qualifiers
source                 1..1063
                       mol_type = protein
                       organism = Homo sapiens
SEQUENCE: 21
MSPGASRGPR GSQAPLIAPL CCAAAALGML LWSPACQAFN LDVEKLTVYS GPKGSYFGYA  60
VDFHIPDART ASVLVGAPKA NTSQPDIVEG GAVYYCPWPA EGSAQCRQIP FDTTNNRKIR  120
VNGTKEPIEF KSNQWFGATV KAHKGKVVAC APLYHWRTLK PTPEKDPVGT CYVAIQNFSA  180
YAEFSPCRNS NADPEGQGYC QAGFSLDFYK NGDLIVGGPG SFYWQGQVIT ASVADIIANY  240
SFKDILRKLA GEKQTEVAPA SYDDSYLGYS VAAGEFTGDS QQELVAGIPR GAQNFGYVSI  300
INSTDMTFIQ NFTGEQMASY FGYTVVVSDV NSDGLDDVLV GAPLFMEREF ESNPREVGQI  360
YLYLQVSSLL FRDPQILTGT ETFGRFGSAM AHLGDLNQDG YNDIAIGVPF AGKDQRGKVL  420
IYNGNKDGLN TKPSQVLQGV WASHAVPSGF GFTLRGDSDI DKNDYPDLIV GAFGTGKVAV  480
YRARPVVTVD AQLLLHPMII NLENKTCQVP DSMTSAACFS LRVCASVTGQ SIANTIVLMA  540
EVQLDSLKQK GAIKRTLFLD NHQAHRVFPL VIKRQKSHQC QDFIVYLRDE TEFRDKLSPI  600
NISLNYSLDE STFKEGLEVK PILNYYRENI VSEQAHILVD CGEDNLCVPD LKLSARPDKH  660
QVIIGDENHL MLIINARNEG EGAYEAELFV MIPEEADYVG IERNNKGFRP LSCEYKMENV  720
TRMVVCDLGN PMVSGTNYSL GLRFAVPRLE KTNMSINFDL QIRSSNKDNP DSNFVSLQIN  780
ITAVAQVEIR GVSHPPQIVL PIHNWEPEEE PHKEEEVGPL VEHIYELHNI GPSTISDTIL  840
EVGWPFSARD EFLLYIFHIQ TLGPLQCQPN PNINPQDIKP AASPEDTPEL SAFLRNSTIP  900
HLVRKRDVHV VEFHRQSPAK ILNCTNIECL QISCAVGRLE GGESAVLKVR SRLWAHTFLQ  960
RKNDPYALAS LVSFEVKKMP YTDQPAKLPE GSIVIKTSVI WATPNVSFSI PLWVIILAIL  1020
LGLLVLAILT LALWKCGFFD RARPPQEDMT DREQLTNDKT PEA                   1063
```

COMPOSITIONS AND PROCESSES FOR ENGINEERING URETERIC BUD KIDNEY TISSUES AND IN-VITRO COMPOSITIONS THEREOF

CROSS-REFERENCE TO RELATED APPLICATIONS

This application claims the benefit of priority to U.S. Provisional Application No. 63/702,872, filed on Oct. 3, 2024, the entire contents of which is incorporated herein by reference.

SEQUENCE LISTING

The instant application contains a Sequence Listing which has been submitted electronically in XML format and is hereby incorporated by reference in its entirety. Said XML copy, created on Aug. 4, 2025, is named 224638-701201_SL.xml and is 38,301 bytes in size.

BACKGROUND

Kidney disease affects approximately 35.5 million Americans and is the 7th leading risk factor for morality globally, with kidney disease rates continuing to rise. The kidney has many functions in the body including maintaining equilibrium of water and minerals, metabolism, excretion, regulating the endocrine system, promoting blood cell and bone formation, and maintaining blood pressure that regulates the cardiovascular system, and others. To improve survival in patients with kidney failure, dialysis is used to filter the patient's blood by removing waste and excess water which temporarily ameliorates severe metabolic acidosis, hyperkalemia, intoxication, and life threatening complications such as cardiac arrhythmias and fluid buildup in the lungs. However, dialysis is not a long-term solution for chronic kidney diseases, placing patients on wait lists for kidney replacement therapy with limited access to kidney transplant and dialysis machines. Therefore, there is a great unmet need for alternative sources for kidney replacement and dialysis therapies.

BRIEF SUMMARY

Provided herein are methods for generating a lumenized kidney tissue having a spatially-controlled 3-dimensional (3D) tubular architecture in vitro, wherein the methods comprise: (a) generating a plurality of ureteric bud (UB) kidney tissues from a population of Wolffian duct progenitor cells that express CXCR4, cKit, or a combination thereof; (b) spatially arranging the plurality of UB kidney tissues in a sequential configuration and in a proximity sufficient to form fused UB kidney tissues that are contiguously fused from at least one connecting point; and (c) culturing the fused UB kidney tissues in a branching medium, thereby forming a lumenized kidney tissue having a spatially-controlled 3D tubular architecture, wherein the lumenized kidney tissue upon contact with a fluid facilitates fluid flow through the spatially-controlled 3D tubular architecture.

In some aspects, the techniques described herein relate to a method, wherein the Wolffian duct progenitor cells are differentiated from human induced pluripotent stem cells.

In some aspects, the techniques described herein relate to a method, wherein the Wolffian duct progenitor cells further express PAX2, EMX2, LHX1, RET1, HOXB7, or a combination thereof.

In some aspects, the techniques described herein relate to a method, wherein the generating includes aggregating the Wolffian duct progenitor cells using centrifugation and differentiating the aggregated Wolffian duct progenitor cells in a suspension culture.

In some aspects, the techniques described herein relate to a method, wherein the generating further includes enriching the Wolffian duct progenitor cells for CXCR4 and cKit expressing Wolffian duct progenitor cells.

In some aspects, the techniques described herein relate to a method, wherein the generating includes contacting the Wolffian duct progenitor cells with a cell culture medium including: retinoic acid, fibroblast growth factor 9 (FGF9), LDN193189, CHIR99021, fibroblast growth factor 1 (FGF1), glial-derived neurotrophic factor 1 (GDNF), Y27632, and a solubilized basement membrane preparation extracted from Engelbreth-Holm-Swarm (EHS) mouse sarcoma.

In some aspects, the techniques described herein relate to a method, wherein the arranging includes bioprinting the plurality of UB kidney tissues.

In some aspects, the techniques described herein relate to a method, further including connecting the plurality of UB kidney tissues to a population of nephron progenitor cells (NPCs) to form a contiguous tubular network between the NPCs and the plurality of UB kidney tissues.

In some aspects, the techniques described herein relate to a method, wherein the branching medium includes retinoic acid, RSPO1, a neurotrophic factor, a fibroblast growth factor, a bone morphogenetic pathway inhibitor, an extracellular matrix, or a combination thereof.

In some aspects, the techniques described herein relate to a method, wherein the at least one connecting point includes: (a) a tip of a UB kidney tissue of the plurality of UB kidney tissues; (b) a stalk a UB kidney tissue of the plurality of UB kidney tissues; (c) a tip of a UB kidney tissue and a stalk of a UB kidney tissue; (d) one or more tips of an adjacent UB kidney tissue of the plurality of UB kidney tissues; (e) one or more stalks of an adjacent UB kidney tissue of the plurality of UB kidney tissues; (f) two or more tips of adjacent UB kidney tissues of the plurality of UB kidney tissues; or (g) two or more stalks of adjacent UB kidney tissues of the plurality of UB kidney tissues; (h) cells isolated from (a)-(c) or a combination thereof; or (i) a combination of any one of (a)-(h).

In some aspects, the techniques described herein relate to an in vitro composition including: an in vitro-differentiated human kidney tissue including a population of human nephron progenitor cells (NPCs) connected to a population of fragmented ureteric bud (UB) kidney tissues, wherein: the in vitro-differentiated human kidney tissue includes a collecting duct, and the in vitro-differentiated human kidney tissue includes two or more markers selected from: LRP2, GATA3, MAFB, and CK8.

In some aspects, the techniques described herein relate to an in vitro-differentiated human kidney tissue including: a population of human nephron progenitor cells (NPCs) connected to a population of fragmented ureteric bud (UB) kidney tissues differentiated from Wolffian duct progenitor cells, wherein the in vitro-differentiated human kidney tissue includes repeating units of nephric-ureteric connections in a sequential configuration.

In some aspects, the techniques described herein relate to an in vitro-differentiated human kidney tissue, wherein each unit is at least about 1 millimeter to about 10 millimeters in size.

In some aspects, the techniques described herein relate to an in vitro-differentiated human kidney tissue, wherein the in vitro-differentiated kidney tissue is 10 mm to about 500 mm in length.

In some aspects, the techniques described herein relate to an in vitro-differentiated human kidney tissue, wherein the in vitro-differentiated kidney tissue includes a lumenized collecting duct.

In some aspects, the techniques described herein relate to an in vitro-differentiated human kidney tissue, wherein the collecting duct expresses a marker selected from: GATA3, EPCAM, and ECAD.

In some aspects, the techniques described herein relate to an in vitro-differentiated human kidney tissue, wherein the in vitro-differentiated kidney tissue includes a proximal tubule.

In some aspects, the techniques described herein relate to an in vitro-differentiated human kidney tissue, wherein the repeating units of nephric-ureteric connections express two or more markers selected from: CK8, MAFB, LRP2, and GATA3.

In some aspects, the techniques described herein relate to an in vitro-differentiated human kidney tissue, wherein the repeating units of nephric-ureteric connections express a nephron marker, wherein the nephron marker includes MAFB or LRP2.

In some aspects, the techniques described herein relate to an in vitro-differentiated human kidney tissue, wherein the repeating units of nephric-ureteric connections express a UB marker, wherein the UB marker is selected from the group consisting of: RET1, SOX9, CK8, and GATA3.

In some aspects, the techniques described herein relate to an in vitro-differentiated human kidney tissue, wherein the in vitro-differentiated kidney tissue includes a glomerular marker, a proximal tubule marker, a tubular epithelium marker, and a connecting segment marker.

In some aspects, the techniques described herein relate to an in vitro-differentiated human kidney tissue, wherein the glomerular marker includes MAFB, WT1, nephrin, or podocin.

In some aspects, the techniques described herein relate to an in vitro-differentiated human kidney tissue, wherein the proximal tubule marker includes LRP2, LTL, CUBN, PTH1R, AQP1, CLDN2, TJP3, or CD13.

In some aspects, the techniques described herein relate to an in vitro-differentiated human kidney tissue, wherein the tubular epithelium marker includes CK8, AQP isoforms, CD34, WGA lectin.

In some aspects, the techniques described herein relate to an in vitro-differentiated human kidney tissue, wherein connecting segment marker includes GATA3 or AQP2.

In some aspects, the techniques described herein relate to an in vitro-differentiated human kidney tissue, wherein the human NPCs are derived from human embryonic stem cells, human induced pluripotent stem cells (iPSCs), or human adult stem cells.

In some aspects, the techniques described herein relate to an in vitro-differentiated human kidney tissue, wherein a portion of a core of the UB kidney tissues include epithelial cells, renal stromal cells, or a combination thereof.

In some aspects, the techniques described herein relate to an in vitro-differentiated human kidney tissue, wherein the Wolffian duct progenitor cells express CXCR4 and cKit; and at least one marker selected from the group consisting of: PAX2, EMX2, LHX1, RET1 and HOXB7.

In some aspects, the techniques described herein relate to a method of generating a lumenized in vitro-differentiated human kidney tissue, the method including: (a) differentiating a population of human induced pluripotent stem cells (iPSCs) to a population of Wolffian duct progenitor cells; (b) isolating Wolffian duct progenitor cells expressing a marker selected from CXCR4, cKit, or a combination thereof; (c) contacting the Wolffian duct progenitor cells isolated from (b) with a first cell culture medium and culturing the Wolffian duct progenitor cells for at least 48 hours in static cell culture conditions, wherein the first cell medium includes: retinoic acid, fibroblast growth factor 9 (FGF9), LDN193189, CHIR99021, fibroblast growth factor 1 (FGF1), glial-derived neurotrophic factor 1 (GDNF), Y27632, a solubilized basement membrane preparation extracted from Engelbreth-Holm-Swarm (EHS) mouse sarcoma, or a combination thereof; (d) arranging the Wolffian duct progenitor cells in a sequential configuration and in a proximity sufficient to form fused UB kidney tissues that are contiguously fused from at least one connecting point; and (e) culturing the fused UB kidney tissues in a branching culture medium for at least 48 hours to form a lumenized in vitro-differentiated human kidney tissue, wherein the branching culture medium includes retinoic acid, RSPO1, a neurotrophic factor, a fibroblast growth factor, a bone morphogenetic pathway inhibitor, an extracellular matrix, or a combination thereof.

In some aspects, the techniques described herein relate to a method, wherein the method further includes combining the lumenized in vitro-differentiated human kidney tissue with a population of in vitro-differentiated human nephron progenitor cells (NPCs) and allowing the combination of the lumenized in vitro-differentiated human kidney tissue and the population of in vitro-differentiated human NPCs to form a contiguous tubular network. 31. 32. 33. 34. 35. 36. 37. 38. 39. 40. 41. 42. 43. 44. 45. 46. 47. 48. 49. 50. 51. 52. 53. 54. 55. 56. 57. 58. 59. 60. 61. 62. (d) (e) (f) 63. 64. 65. 66. 67. 68. 69. 70. 71. 72. 73. 74. 75. 76. 77. 78. 79. 80. 81. 82. 83. 84. 85. 86. 87. 88. 89. 90. 91. 92. 93. 94. 95. 96. 97. 98. 99. 100. 101. 102. 103. 104. 105. 106. 107. 108. 109. 110. 111. 112. 113. 114. 115. 116. 117. 118. 119. 120. 121. 122. 123. 124. 125. 126. 127. 128. 129. 130. 131. 132. 133. 134. 135. 136. 137. 138. 139. 140. 141. 142. 143. 144. 145. 146. 147. 148. (a) (b) (c) (d) (e) 149. 150. 151. 152. 153. 154. 155. 156. 157. 158. 159. 160. 161. 162. 163. 164. 165. 166. 167. 168. 169. 170. 171. 172. 173. 174. 175. 176. 177. 178. 179. 180. 181. 182. 183. 184. 185. 186. 187. 188. 189. 190. 191. 192.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 1A shows a schematic representation of the method of making ureteric bud kidney tissues made by the methods outline in Example 1. FIG. 1B shows a schematic of the media composition and steps for each stage of lumenized kidney tissue generation described in Example 1. PSC: Pluripotent stem cells; PS: primitive streak; AIM: anterior intermediate mesoderm cells; WDP: Wolffian Duct progenitor cells; UB: ureteric bud cells; RA: retinoic acid. FIG. 1C shows a schematic representation of the method of making nephron progenitor cells and tissues described herein. PSC: Pluripotent stem cell; PS: primitive streak; PIM: posterior intermediate mesoderm cells; MM: Metanephric Mesenchymal cells; NPC: nephron progenitor cells.

FIG. 4A shows cells on the day of aggregation. D6.5 cells from the protocol outlined in FIG. 1A and FIG. 1B. FIG. 4B shows cells 24 hours following aggregation, day 7.5 (D7.5) cells from the protocol outlined in FIG. 1A and FIG. 1B. FIG. 4C shows cells 48 hours following aggregation, D8.5 cells from the protocol outlined in FIG. 1A and FIG. 1B.

FIG. 6A shows images over the course of UB fusion from day D10.5 to D18.5 of the UB protocol shown in FIG. 1A and FIG. 1B. FIG. 6B shows a magnified view of UB tissue fusions. FIG. 6C shows images of large UB kidney tissues from D10.5 to D23.5. Fused tissues remodel over time to form putative contiguous epithelium (arrow). Example dot array shows one tissue connected to five adjacent tissues. Asterisk marks single tissue that did not connect, likely due to distance between other UB tissues. FIG. 6D shows expression of UB marker genes enriched in tip (SOX9, RET1) and stalk (CK8). FIG. 6E shows a ureteric bud kidney tissue (top image) and a cross section of the tubular epithelium (bottom image) at positions a-b.

FIG. 11A shows a merged image of markers for the proximal tubule (LRP2), the glomerulus (MAFB-GFP), tubular epithelium (CK8), and ureteric epithelium (GATA3). FIG. 11B shows images of the individual channels for each marker as indicated.

FIG. 12A shows images of regions with (1) connected UB kidney tissues and nephrons, (2) not connected tissues; and (3) aberrant tubule connections (for example, PT-PT) within tissues. FIG. 12B shows a graph quantifying the nephron and UB connections by 3D mapping. Y-axis: nephron disposition %; X-axis: 1: connected tissues; 2: not connected tissues; and 3: aberrant connections.

FIG. 14A shows exemplary patterns for bioprinting cellular bioinks in Matrigel. FIG. 14B shows tissue formation and ureteric-nephron connections following bioprinting.

DETAILED DESCRIPTION

Figure 1A:
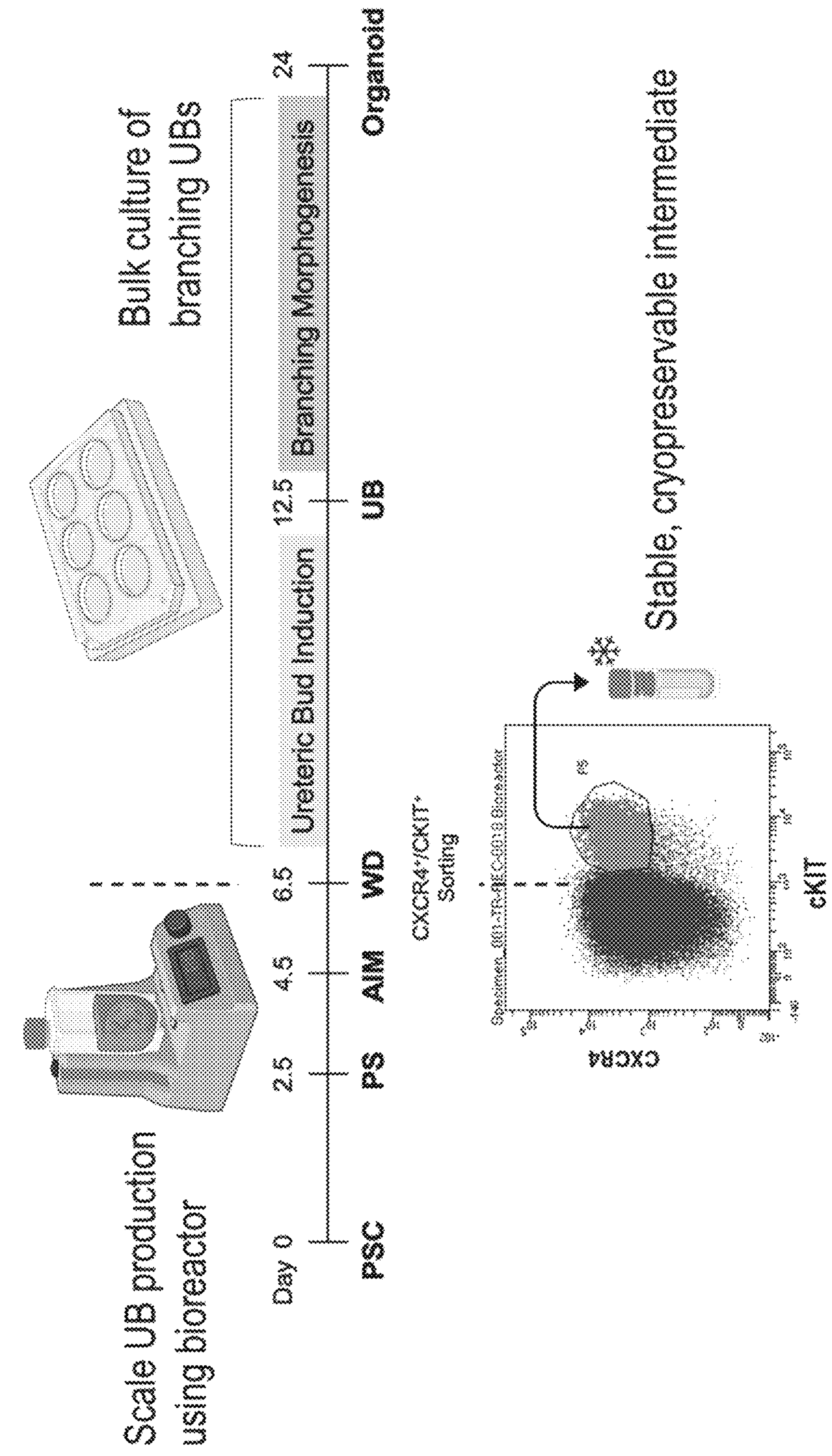
FIGS. 1A-1C show exemplary protocols for generating ureteric bud kidney tissues, nephron tissues, and nephron-ureteric bud tissues.

Provided herein are in vitro kidney tissues and in vitro kidneys for use in the treatment of a disease or condition in a subject. Further provided herein are compositions and methods of making, engineering, and using an in vitro kidney tissue, an in vitro kidney, compositions, systems, and kits. The in vitro kidneys and kidney tissues described herein are the first demonstration of nephron and ureteric kidney tissue connections between stem cell-derived nephron progenitor cells and ureteric bud cells. The in vitro kidneys and kidney tissues have several advantages over primary kidney tissues, including reproducibility, scalability, safety, and can be made using human-derived kidney cells without being limited by donors.

Briefly, described herein are (1) ureteric bud kidney tissues and methods of making the same; (2) nephron kidney tissues and methods of making the same; (3) methods of making in vitro kidneys and lumenized in vitro kidneys; (4) transplant compositions; (5) systems; (6) kits and reagents; and (7) methods of treatment, dosing, and administration.

Definitions

Unless defined otherwise, all technical and scientific terms used herein have the same meaning as is commonly understood by one of ordinary skill in the art.

The terminology used herein is for the purpose of describing particular embodiments only and is not intended to be limiting. As used herein, the singular forms “a”, “an” and “the” are intended to include the plural forms as well, unless the context clearly indicates otherwise. Furthermore, to the extent that the terms “including”, “includes”, “having”, “has”, “with”, or variants thereof as used herein mean “comprising”.

The term “about” and its grammatical equivalents in relation to a reference numerical value and its grammatical equivalents as used herein may include a range of values plus or minus 10% from that value. For example, the amount "about 10" includes amounts from 9 to 11. The term "about" in relation to a reference numerical value may also include a range of values plus or minus: 10%, 9%, 8%, 7%, 6%, 5%, 4%, 3%, 2%, or 1% from that value.

The term "substantially" as used herein may refer to a value approaching 100% of a given value. In some embodiments, the term may refer to an amount that can be at least about 90%, 91%, 92%, 93%, 94%, 95%, 96%, 97%, 98%, 99%, 99.9%, or 99.99% of a total amount. In some embodiments, the term may refer to an amount that can be about 100% of a total amount.

The term "effective amount" or "therapeutically effective amount" may refer to a quantity of a composition, for example a composition comprising cells such as cells, that can be sufficient to result in a desired activity upon introduction into an isolated organ or portion thereof provided herein.

The term "function" and its grammatical equivalents as used herein may refer to a capability of operating, having, or serving an intended purpose. Functional may comprise any percent from baseline to 100% of an intended purpose. For example, functional may comprise or comprise about 5%, 10%, 15%, 20%, 25%, 30%, 35%, 40%, 45%, 50%, 55%, 60%, 65%, 70%, 75%, 80%, 85%, 90%, 95%, or up to about 100% of an intended purpose. In some embodiments, the term functional may mean over or over about 100% of normal function, for example, 125%, 150%, 175%, 200%, 250%, 300%, 400%, 500%, 600%, 700% or up to about 1000% of an intended purpose.

The terms "treatment" or "treating" and their grammatical equivalents may refer to the medical management of a subject with an intent to cure, ameliorate, stabilize, or prevent a disease, condition, or disorder. Treatment may include active treatment, that is, treatment directed specifically toward the improvement of a disease, condition, or disorder. Treatment may include causal treatment, that is, treatment directed toward removal of the cause of the associated disease, condition, or disorder. In addition, this treatment may include palliative treatment, that is, treatment designed for the relief of symptoms rather than the curing of the disease, condition, or disorder. Treatment may include preventative treatment, that is, treatment directed to minimizing or partially or completely inhibiting the development of a disease, condition, or disorder. Treatment may include supportive treatment, that is, treatment employed to supplement another specific therapy directed toward the improvement of the disease, condition, or disorder. In some embodiments, a condition can be pathological. In some embodiments, a treatment may not completely cure, ameliorate, stabilize, or prevent a disease, condition, or disorder.

(1) Ureteric Bud Kidney Tissues and Methods of Making the Same.

A ureteric bud as described herein is a functional element of kidney tissues provided herein that is composed of ureteric bud cells, epithelial cells, renal stromal cells, mesenchymal stem cells, and/or Wolffian duct cells. During fetal and neonatal development in mammals, the ureteric bud is the portion of the developing nephron of the kidney that branches out to form the collecting duct, the ureter, the renal pelvis, calyces. The collecting duct (also called the renal collecting tubule) has multiple functions in the kidney such as reabsorbing water and electrolytes, concentrating urine with urea, and maintaining fluid electrolyte balance.

Ureteric bud (UB) outgrowth from the Wolffian duct depends on a number of pathways, and its perturbation can cause diseases such as renal agenesis, vesicoureteral reflux, obstructive uropathy, and congenital anomalies of the kidney and urinary tract, which can result in chronic kidney disease. The UB forms in response to external cues provided by surrounding metanephric mesenchyme. Ureteric bud formation is initiated at week 5 of human fetal gestation and at embryonic day 10.5 (E10.5) in mice. Signals from the metanephric mesenchyme induce the ureteric bud to form, elongate, and invade the mesenchyme. The branching process is initiated by the binding of glial-derived neurotrophic factor (GDNF), a soluble growth factor elaborated by the metanephric mesenchyme, to its co-receptors (RET and GFRA1) found on cells of the nephric/Wolffian duct. After penetration into the metanephric mesenchyme, reciprocal induction between these progenitor tissues leads to iterative UB growth and branching to develop into the renal collecting system. Meanwhile the metanephric mesenchyme aggregates, condenses, and epithelializes around branched UB tips to form comma- and S-shaped bodies that differentiate into various parts of the nephron, including the proximal and distal tubules and epithelial components of the glomeruli. Together, these mutually inductive morphogenetic processes will give rise to the fully functional metanephric kidney, producing urine at about E16.5 in mice and around 9-10 weeks of gestation in humans. Meanwhile, the part of the UB outside the metanephric mesenchyme has a different fate because it elongates to form the ureter, a tubular structure that is the conduit for the flow of urine between the kidney and the bladder. While UB cells have been differentiated from human induced pluripotent stem cells, they do not have the ability to form a collecting duct that is lumenized (has a sequential configuration and/or tubular structure that permits the flow of fluids). The inventors have recognized and appreciated a method of producing an in vitro-lumenized kidney tissue that has lumenized collecting duct from in vitro-differentiated UB cells recapitulating the structural morphology of the mammalian collecting duct and expresses markers of the ureteric bud consistent with markers expressed by the collecting duct in mammalian kidneys in vivo.

Provided herein are compositions comprising a population of ureteric bud kidney cells, also abbreviated herein as UBs. Ureteric bud cells can be from any source or species, including but not limited to: primary mammalian kidney ureteric bud cells, ureteric bud progenitor cells (UBPCs) and differentiated progeny, Wolffian duct cells, UB cell lines, differentiated UBs from stem cells, and combinations thereof. In some embodiments, the UBs are derived from stem cells, wherein the stem cells are induced pluripotent stem cells (iPSCs), embryonic stem cells, and adult stem cells. In some embodiments, the UB are derived from human iPSCs.

Methods of differentiating UBs are described, for example, in Taguchi and Nishinakamura, *Cell Stem Cell,* 2017, the contents of which is incorporated herein by reference in its entirety.

Provided herein are methods of generating UB kidney tissues, wherein the methods comprise contacting a population of human induced pluripotent stem cells (iPSCs) with a first cell culture medium for a period of time to form to cell aggregates comprising in vitro-differentiated human UB progenitor cells. In some embodiments, human pluripotent stem cells are aggregated in a suspension culture. In some embodiments, the human iPSCs are cultured in a first cell culture medium to form human iPSC aggregates.

A cell culture medium provided herein can comprise a basal medium supplemented with one or more growth factors, metabolites, antioxidants, antigens, small molecules, and/or proteins that permit differentiation of a stem cell to a ureteric bud (UB) progenitor cell or a UB cell. In some embodiments, the cell culture medium comprises a basal differentiation medium (DM). In some embodiments, the cell culture medium comprises serum. In some embodiments, the serum is fetal bovine serum (FBS). In some embodiments, the cell culture medium is serum-free cell culture medium. In some embodiments, the cell culture medium comprises a basal medium, wherein the basal medium comprises Dulbecco's Modified Eagle Medium/Nutrient Mixture F-12 (DMEM/F12). In some embodiments, the cell culture medium comprises an antigen. In some embodiments, the cell culture medium comprises a B27 supplement. In some embodiments, the cell culture medium comprises a retinoic acid receptor agonist. In some embodiments, the cell culture medium comprises retinoic acid. In some embodiments, the cell culture medium does not comprise retinoic acid. In some embodiments, the cell culture medium comprises insulin-transferrin-selenium (ITS). In some embodiments, the cell culture medium comprises non-essential amino acids (NEAA). In some embodiments, the cell culture medium comprises L-glutamine. In some embodiments, the cell culture medium comprises an antibiotic. In some embodiments, the cell culture medium comprises penicillin and/or streptomycin. In some embodiments, the cell culture medium comprises an antioxidant. In some embodiments, the cell culture medium comprises 2-mercaptoethanol. In some embodiments, the cell culture medium comprises: a Rho kinase (ROCK) inhibitor. In some embodiments, the Rho kinase (ROCK) inhibitor comprises: Y27632 (CAS No. 129830-38-2), Y30141 (CAS No. 199433-55-1), Y33075 (CAS No. 471843-75-1), Y39983 (CAS No. 203911-26-6), or any combination thereof. In some embodiments, the cell culture medium comprises an activin receptor ligand (e.g., Activin A). In some embodiments, the cell culture medium does not comprise an activin receptor ligand (e.g., Activin A). In some embodiments, the cell culture medium comprises: a transforming growth factor β receptor family ligand. In some embodiments, the growth factor comprises BMP1, BMP2, BMP3, BMP4, BMP5, BMP6, BMP7, BMP8, BMP9, BMP10, fibroblast growth factor (FGF), epidermal growth factor (EGF), hedgehog molecules, insulin-like growth factor (IGF), platelet-derived growth factor (PDGF), VEGF, or a WNT molecule. In some embodiments, the cell culture medium comprises an ALK inhibitor. In some embodiments, the ALK inhibitor comprises LDN193189 (4-[6-[4-(1-Piperazinyl)phenyl]pyrazolo[1,5-a]pyrimidin-3-yl]quinoline dihydrochloride, CAS No. 1435934-00-1). In some embodiments, the cell culture medium comprises a WNT pathway activator. In some embodiments, the WNT pathway activator comprises a glycogen synthase kinase 3 inhibitor. In some embodiments, the cell culture medium does not comprise a glycogen synthase kinase 3 inhibitor. In some embodiments, the glycogen synthase kinase 3 inhibitor comprises a small molecule selected from the group consisting of: CHIR98014 (CAS No. 252935-94-7), CHIR98024 (CAS No. 556813-39-9), CHIR99021 (CAS No. 252917-06-9), 2,4'-dibromoacetophenone, and dihydronarwedine. In some embodiments, the cell culture medium comprises A-77-01 (CAS No. 607737-87-1), EW-7197 (CAS No. 1352608-82-2), GW 788388 (CAS No. 452342-67-5), LDN-193189, LDN-214117 (CAS No. 1627503-67-6), SB-431542 (CAS No. 301836-41-9), SB-202190 (CAS No. 152121-30-7), SB-505124 (CAS No. 694433-59-5), or SM-16 (CAS No. 614749-78-9). In some embodiments, the cell culture medium comprises a fibroblast growth factor (FGF). In some embodiments, the FGF comprises FGF1, FGF2, FGF3, FGF4, FGF5, FGF6, FGF7, FGF8, FGF9, FGF10, FGF16, FGF17, FGF18, FGF19, FGF20, FGF21, FGF22, FGF23, or any combination thereof. In some embodiments, a cell culture medium comprises a glial cell line-derived neurotrophic factor (GDNF) or a tumor growth factor (e.g., TGF-beta 2).

The cells provided herein, for example, human iPSCs, human iPSC aggregates, UB progenitor cells, 3D aggregates, and/or UB kidney cells provided herein, can be cultured under conditions that permit growth, maintenance, survival, and/or differentiation of the cells for use in generating an in vitro-differentiated kidney or in vitro kidney tissue provided herein. Cells can be cultured in an incubator or a bioreactor that maintains temperature, $CO_2$ levels, oxygen levels, and humidity. In general, cells are cultured at between about 35 degrees Celsius to about 38 degrees Celsius, at approximately 5% $CO_2$ level, and approximately 95% humidity, unless otherwise indicated. The cells provided herein can be cultured for a period of time that permits differentiation of one progenitor cell type to another cell type. Exemplary protocols and timelines are provided in FIG. 1A, FIG. 1B, and FIG. 1C.

The cells provided herein can be in contact with an extracellular matrix that supports cellular structure, differentiation, growth, and survival. In some embodiments, the extracellular matrix is on a solid support, such as a cell culture dish or a tube. In some embodiments, the extracellular matrix is in suspension with the cells provided herein. In some embodiments, the extracellular matrix comprises: extracellular matrix comprises a solubilized basement membrane preparation extracted from Engelbreth-Holm-Swarm (EHS) mouse sarcoma, laminin, collagen IV, heparan sulfate proteoglycans, entactin, fibronectin, vitronectin, retronectin, elastin, hyaluronic acid, methylcellulose, a gelatin, or any combination thereof.

In some embodiments, the human iPSCs or human iPSC aggregates are cultured in suspension culture at about 37 degrees C. with about 5% $CO_2$ and about 95% relative humidity for at least 8 hours, at least 12 hours, at least 20 hours, at least 24 hours, at least 36 hours, or at least 48 hours. In some embodiments, the human iPSCs or human iPSC aggregates are cultured at 38 degrees C. with 5% $CO_2$ and 95% relative humidity for at least 8 hours, at least 12 hours, at least 20 hours, at least 24 hours, at least 36 hours, or at least 48 hours.

In some embodiments, the human iPSC aggregates are cultured in a second cell culture medium to form in vitro-differentiated UB progenitor cells. In some embodiments, the cell culture medium comprises basal DM. In some embodiments, the cell culture medium comprises CHIR99021. In some embodiments, the cell culture medium comprises CHIR99021 and BMP4. In some embodiments, the cell culture medium comprises retinoic acid. In some embodiments, the cell culture medium comprises FGF9. In some embodiments, the cell culture medium comprises LDN193189. In some embodiments, the cell culture medium comprises SB431542. In some embodiments, the cell culture medium comprises retinoic acid, FGF9, LDN193189, and/or CHIR99021.

In some embodiments, the human iPSC aggregates or in vitro-differentiated UB progenitor cells are cultured at 35° C. with 5% $CO_2$ and 95% relative humidity for at least 8 hours, at least 12 hours, at least 20 hours, at least 24 hours, at least 36 hours, at least 48 hours, at least 60 hours, at least 72 hours, at least 84 hours, at least 96 hours, at least 108 hours, at least 120 hours, at least 132 hours, at least 144 hours, at least 156 hours, or at least 168 hours. In some embodiments, the human iPSC aggregates or in vitro-differentiated UB progenitor cells are cultured at 36° C. with 5% $CO_2$ and 95% relative humidity for at least 8 hours, at least 12 hours, at least 20 hours, at least 24 hours, at least 36 hours, at least 48 hours, at least 60 hours, at least 72 hours, at least 84 hours, at least 96 hours, at least 108 hours, at least 120 hours, at least 132 hours, at least 144 hours, at least 156 hours, or at least 168 hours. In some embodiments, the human iPSC aggregates or in vitro-differentiated UB progenitor cells are cultured at 37° C. with 5% $CO_2$ and 95% relative humidity for at least 8 hours, at least 12 hours, at least 20 hours, at least 24 hours, at least 36 hours, at least 48 hours, at least 60 hours, at least 72 hours, at least 84 hours, at least 96 hours, at least 108 hours, at least 120 hours, at least 132 hours, at least 144 hours, at least 156 hours, or at least 168 hours. In some embodiments, the human iPSC aggregates or in vitro-differentiated UB progenitor cells are cultured at 38° C. with 5% CO2 and 95% relative humidity for at least 8 hours, at least 12 hours, at least 20 hours, at least 24 hours, at least 36 hours, at least 48 hours, at least 60 hours, at least 72 hours, at least 84 hours, at least 96 hours, at least 108 hours, at least 120 hours, at least 132 hours, at least 144 hours, at least 156 hours, or at least 168 hours.

In some embodiments, cell aggregates comprising the in vitro-differentiated UB progenitor cells are collected from suspension culture and centrifuged. In some embodiments, the cell aggregates are centrifuged for at least 1 minute, at least 2 minutes, at least 3 minutes, at least 4 minutes, or at least 5 minutes. In some embodiments, the cell aggregates are centrifuged at a relative centrifugal force of at least about 50 g, at least about 60 g, at least about 70 g, at least about 80 g, at least about 90 g, at least about 100 g, at least about 110 g, at least about 120 g, at least about 130 g, at least about 140 g, at least about 150 g, at least about 200 g, at least about 300 g, at least about 400 g, or at least about 500 g.

In some embodiments, the cell aggregates are contacted with a proteolytic enzyme or a cell dissociation reagent to break up the cell aggregates into dispersed cells. In some embodiments, the proteolytic enzyme is trypsin, accutase, collagenase, prolinase, or a high purity recombinant fungal serine protease (e.g., TrypLE). In some embodiments, the cell aggregates are contacted with a proteolytic enzyme or a cell dissociation reagent for at least about 30 seconds, at least about 1 minute, at least about 2 minutes, at least about 3 minutes, at least about 4 minutes, at least about 5 minutes, at least about 6 minutes, at least about 7 minutes, at least about 8 minutes, at least about 9 minutes, at least about 10 minutes, or at least about 15 minutes. In some embodiments, a cell culture medium is added to the dispersed cells in contact with the proteolytic enzyme or cell dissociation reagent to stop single cell dissociation.

In some embodiments, the dissociated cells are enriched for or sorted for double-positive CXCR4/CKIT cell surface markers to obtain CXCR4+/CKIT+ cells. In some embodiments, the CXCR4 and cKit double positive cells are Wolffian duct progenitor cells. Methods of sorting and enriching for cells with specific marker include, for example, flow cytometry. In some embodiments, the CXCR4+/CKIT+ cells are isolated and aggregated in a cell culture medium. In some embodiments the cell culture medium comprises retinoic acid, FGF9, LDN193189, CHIR99021, FGF1, Y27632, and/or Matrigel® (e.g., a solubilized basement membrane preparation extracted from Engelbreth-Holm-Swarm (EHS) mouse sarcoma, laminin, and collagen IV). In some embodiments, the CXCR4+/CKIT+ cells are incubated at 37 degrees Celsius at 5% $CO_2$ for at least 8 hours, at least 12 hours, at least 20 hours, at least 24 hours, at least 36 hours, at least 48 hours, at least 60 hours, at least 72 hours, at least 84 hours, at least 96 hours, at least 108 hours, at least 120 hours, at least 132 hours, at least 144 hours, at least 156 hours, or at least 168 hours.

In some embodiments, the CXCR4+/CKIT+ cells form CXCR4+/CKIT+ cell aggregates. In some embodiments, the CXCR4+/CKIT+ cell aggregates are contacted with in a cell culture medium comprising retinoic acid, FGF9, LDN193189, CHIR99021, FGF1, GDNF (e.g., GDNF1), Y27632, and/or Matrigel® (e.g., a solubilized basement membrane preparation extracted from Engelbreth-Holm-Swarm (EHS) mouse sarcoma, laminin, and collagen IV). In some embodiments, the CXCR4+/CKIT+ cell aggregates facilitate fusion of the cells into 3-dimensional (3D) aggregates. In some embodiments, the 3D aggregates are spatially-controlled by methods provided herein to form a tubular architecture. In some embodiments, the 3D aggregates are arranged into the tubular architecture by bioprinting a mixture of 3D aggregates and a solubilized basement membrane onto a scaffold. In some embodiments, the 3D aggregates are arranged into the tubular architecture by bioprinting the 3D aggregates directly onto a scaffold, a solid support, an extracellular matrix, or any combination thereof. In some embodiments, the 3D aggregates are arranged in a contiguous linear pattern. In some embodiments, the 3D aggregates are arranged in a sequential linear pattern or a sequential circular pattern.

In some embodiments, the 3D aggregates are contacted with a cell culture medium comprising: retinoic acid, CHIR99021, LDN193189, GDNF1, FGF1, and/or Y27632. In some embodiments, the 3D aggregates are incubated at 37 degrees Celsius at 5% $CO_2$ for at least 8 hours, at least 12 hours, at least 20 hours, at least 24 hours, at least 36 hours, at least 48 hours, at least 60 hours, at least 72 hours, at least 84 hours, at least 96 hours, at least 108 hours, at least 120 hours, at least 132 hours, at least 144 hours, at least 156 hours, or at least 168 hours.

To promote the outgrowth from the 3D aggregates and development of branching lumenized, ureteric structures, the 3D aggregates can be moved from a suspension culture to a transwell-based cell culture. In some embodiments, the 3D aggregates are contacted with a cell culture medium and form lumenized ureteric bud (UB) kidney tissues. In some embodiments, the cell culture medium comprises a UB branching medium. In some embodiments, the UB branching medium comprises: DMEM/F12, fetal bovine serum, penicillin, streptomycin, retinoic acid, R-spondin-1 (RSPO1), GDNF1, FGF1, FGF7, LDN193189, and/or Matrigel. In some embodiments, the 3D aggregates are incubated in the branching medium at 37 degrees Celsius at 5% $CO_2$ for at least 8 hours, at least 12 hours, at least 20 hours, at least 24 hours, at least 36 hours, at least 48 hours, at least 60 hours, at least 72 hours, at least 84 hours, at least 96 hours, at least 108 hours, at least 120 hours, at least 132 hours, at least 144 hours, at least 156 hours, or at least 168 hours.

Provided herein are ureteric bud kidney tissues comprising or expressing one or more UB markers. A marker can comprise a surface marker, a genomic marker, a protein, an RNA, a DNA, or a cDNA that is present in, expressed by, or presented by a UB kidney tissue provided herein. In some embodiments, the UB marker comprises a marker selected from the group consisting of a RET gene or protein (also called rearranged during transfection or RET receptor tyrosine kinase), a cytokeratin gene or protein, and a SOX (also called SRY-box transcription factor) gene or protein, a C-X-C chemokine receptor gene or protein, a c-Kit gene or protein (also called KIT proto-oncogene receptor tyrosine kinase), a GATA gene or protein, and any combination thereof. In some embodiments, the UB marker is a marker provided in Table 1, an ortholog, a homolog, or a variant thereof (e.g., an alternative splice variant or a mutant).

TABLE 1

UB Markers

| Marker Name | Exemplary Protein Sequences | NCBI Gene ID |
|---|---|---|
| RET1 (rearranged during transfection, RET receptor tyrosine kinase) | >NP_001393672.1 proto-oncogene tyrosine-protein kinase receptor Ret isoform a precursor [*Homo sapiens*] MAKATSGAAGLRLLLLLLLPLLGKVALGLYFSRDAYW EKLYVDQAAGTPLLYVHALRDAPEEVPSFRLGQHLYG TYRTRLHENNWICIQEDTGLLYLNRSLDHSSWEKLSV RNRGFPLLTVYLKVFLSPTSLREGECQWPGCARVYFS FFNTSFPACSSLKPRELCFPETRPSFRIRENRPPGTF HQFRLLPVQFLCPNISVAYRLLEGEGLPFRCAPDSLE VSTRWALDREQREKYELVAVCTVHAGAREEVVMVPFP VTVYDEDDSAPTFPAGVDTASAVVEFKRKEDTVVATL RVFDADVVPASGELVRRYTSTLLPGDTWAQQTFRVEH WPNETSVQANGSFVRATVHDYRLVLNRNLSISENRTM QLAVLVNDSDFQGPGAGVLLLHFNVSVLPVSLHLPST YSLSVSRRARRFAQIGKVCVENCQAFSGINVQYKLHS SGANCSTLGVVTSAEDTSGILFVNDTKALRRPKCAEL HYMVVATDQQTSRQAQAQLLVTVEGSYVAEEAGCPLS CAVSKRRLECEECGGLGSPTGRCEWRQGDGKGITRNF STCSPSTKTCPDGHCDVVETQDINICPQDCLRGSIVG GHEPGEPRGIKAGYGTCNCFPEEEKCFCEPEDIQDPL CDELCRTVIAAAVLFSFIVSVLLSAFCIHCYHKFAHK PPISSAEMTFRRPAQAFPVSYSSSGARRPSLDSMENQ VSVDAFKILEDPKWEFPRKNLVLGKTLGEGEFGKVVK ATAFHLKGRAGYTTVAVKMLKENASPSELRDLLSEFN VLKQVNHPHVIKLYGACSQDGPLLLIVEYAKYGSLRG FLRESRKVGPGYLGSGGSRNSSSLDHPDERALTMGDL ISFAWQISQGMQYLAEMKLVHRDLAARNILVAEGRKM KISDFGLSRDVYEEDSYVKRSQGRIPVKWMAIESLFD HIYTTQSDVWSFGVLLWEIVTLGGNPYPGIPPERLEN LLKTGHRMERPDNCSEEMYRLMLQCWKQEPDKRPVFA DISKDLEKMMVKRRDYLDLAASTPSDSLIYDDGLSEE ETPLVDCNNAPLPRALPSTWIENKLYGMSDPNWPGES PVPLTRADGTNTGFPRYPNDSVYANWMLSPSAAKLMD TFDS (SEQ ID NO: 1) | Gene ID: 5979 |
| CK8 (cytokeratin 8) | >NP_001243211.1 keratin, type II cytoskeletal 8 isoform 1 [*Homo sapiens*] MNGVSWSQDLQEGISAWFGPPASTPASTMSIRVTQKS YKVSTSGPRAFSSRSYTSGPGSRISSSSFSRVGSSNF RGGLGGGYGGASGMGGITAVTVNQSLLSPLVLEVDPN IQAVRTQEKEQIKTLNNKFASFIDKVRFLEQQNKMLE TKWSLLQQQKTARSNMDNMFESYINNLRRQLETLGQE KLKLEAELGNMQGLVEDFKNKYEDEINKRTEMENEFV LIKKDVDEAYMNKVELESRLEGLTDEINFLRQLYEEE IRELQSQISDTSVVLSMDNSRSLDMDSIIAEVKAQYE DIANRSRAEAESMYQIKYEELQSLAGKHGDDLRRTKT EISEMNRNISRLQAEIEGLKGQRASLEAAIADAEQRG ELAIKDANAKLSELEAALQRAKQDMARQLREYQELMN VKLALDIEIATYRKLLEGEESRLESGMQNMSIHTKTT SGYAGGLSSAYGGLTSPGLSYSLGSSFGSGAGSSSFS RTSSSRAVVVKKIETRDGKLVSESSDVLPK (SEQ ID NO: 2) | Gene ID: 3856 |
| SOX9 (SRY-box transcription factor 9) | >NP_000337.1 transcription factor SOX-9 [*Homo sapiens*] MNLLDPFMKMTDEQEKGLSGAPSPTMSEDSAGSPCPS GSGSDTENTRPQENTFPKGEPDLKKESEEDKFPVCIR EAVSQVLKGYDWTLVPMPVRVNGSSKNKPHVKRPMNA FMVWAQAARRKLADQYPHLHNAELSKTLGKLWRLLNE SEKRPFVEEAERLRVQHKKDHPDYKYQPRRRKSVKNG QAEAEEATEQTHISPNAIFKALQADSPHSSSGMSEVH SPGEHSGQSQGPPTPPTTPKTDVQPGKADLKREGRPL PEGGRQPPIDFRDVDIGELSSDVISNIETFDVNEFDQ YLPPNGHPGVPATHGQVTYTGSYGISSTAATPASAGH VWMSKQQAPPPPPQQPPQAPPAPQAPPQPQAAPPQQP AAPPQQPQAHTLTTLSSEPGQSQRTHIKTEQLSPSHY SEQQQHSPQQIAYSPFNLPHYSPSYPPITRSQYDYTD HQNSSSYYSHAAGQGTGLYSTFTYMNPAQRPMYTPIA DTSGVPSIPQTHSPQHWEQPVYTQLTRP ( SEQ ID NO: 3) | Gene ID: 6662 |

TABLE 1-continued

| UB Markers | | |
|---|---|---|
| Marker Name | Exemplary Protein Sequences | NCBI Gene ID |
| CXCR4 (C-X-C chemokine receptor type 4) | >NP_001008540.1 C-X-C chemokine receptor type 4 isoform a [*Homo sapiens*] MSIPLPLLQIYTSDNYTEEMGSGDYDSMKEPCFREEN ANFNKIFLPTIYSIIFLTGIVGNGLVILVMGYQ KKLRSMTDKYRLHLSVADLLFVITLPFWAVDAVANWY FGNFLCKAVHVIYTVNLYSSVLILAFISLDRYL AIVHATNSQRPRKLLAEKVVYVGVWIPALLLTIPDFI FANVSEADDRYICDRFYPNDLWVVVFQFQHIMV GLILPGIVILSCYCIIISKLSHSKGHQKRKALKTTVI LILAFFACWLPYYIGISIDSFILLEIIKQGCEF ENTVHKWISITEALAFFHCCLNPILYAFLGAKFKTSA QHALTSVSRGSSLKILSKGKRGGHSSVSTESES SSFHSS (SEQ ID NO: 4) | Gene ID: 7852 |
| C-Kit or KIT (KIT proto-oncogene, receptor tyrosine kinase) | >NP_000213.1 mast/stem cell growth factor receptor Kit isoform 1 precursor [*Homo sapiens*] MRGARGAWDFLCVLLLLLRVQTGSSQPSVSPGEPSPP SIHPGKSDLIVRVGDEIRLLCTDPGFVKWTFEI LDETNENKQNEWITEKAEATNTGKYTCTNKHGLSNSI YVFVRDPAKLFLVDRSLYGKEDNDTLVRCPLTD PEVTNYSLKGCQGKPLPKDLRFIPDPKAGIMIKSVKR AYHRLCLHCSVDQEGKSVLSEKFILKVRPAFKA VPVVSVSKASYLLREGEEFTVTCTIKDVSSSVYSTWK RENSQTKLQEKYNSWHHGDFNYERQATLTISSA RVNDSGVFMCYANNTFGSANVTTTLEVVDKGFINIFP MINTTVFVNDGENVDLIVEYEAFPKPEHQQWIY MNRTFTDKWEDYPKSENESNIRYVSELHLTRLKGTEG GTYTFLVSNSDVNAAIAFNVYVNTKPEILTYDR LVNGMLQCVAAGFPEPTIDWYFCPGTEQRCSASVLPV DVQTLNSSGPPFGKLVVQSSIDSSAFKHNGTVE CKAYNDVGKTSAYFNFAFKGNNKEQIHPHTLFTPLLI GFVIVAGMMCIIVMILTYKYLQKPMYEVQWKVV EEINGNNYVYIDPTQLPYDHKWEFPRNRLSFGKTLGA GAFGKVVEATAYGLIKSDAAMTVAVKMLKPSAH LTEREALMSELKVLSYLGNHMNIVNLLGACTIGGPTL VITEYCCYGDLLNFLRRKRDSFICSKQEDHAEA ALYKNLLHSKESSCSDSTNEYMDMKPGVSYVVPTKAD KRRSVRIGSYIERDVTPAIMEDDELALDLEDLL SFSYQVAKGMAFLASKNCIHRDLAARNILLTHGRITK ICDFGLARDIKNDSNYVVKGNARLPVKWMAPES IFNCVYTFESDVWSYGIFLWELFSLGSSPYPGMPVDS KFYKMIKEGFRMLSPEHAPAEMYDIMKTCWDAD PLKRPTFKQIVQLIEKQISESTNHIYSNLANCSPNRQ KPVVDHSVRINSVGSTASSSQPLLVHDDV (SEQ ID NO: 5) | Gene ID: 3815 |
| GATA3 (GATA binding protein 3) | >NP_001002295.1 trans-acting T-cell-specific transcription factor GATA-3 isoform 1 [*Homo sapiens*] MEVTADQPRWVSHHHPAVLNGQHPDTHHPGLSHSYMD AAQYPLPEEVDVLFNIDGQGNHVPPYYGNSVRATVQR YPPTHHGSQVCRPPLLHGSLPWLDGGKALGSHHTASP WNLSPFSKTSIHHGSPGPLSVYPPASSSSLSGGHASP HLFTFPPTPPKDVSPDPSLSTPGSAGSARQDEKECLK YQVPLPDSMKLESSHSRGSMTALGGASSSTHHPITTY PPYVPEYSSGLFPPSSLLGGSPTGFGCKSRPKARSST EGRECVNCGATSTPLWRRDGTGHYLCNACGLYHKMNG QNRPLIKPKRRLSAARRAGTSCANCQTTTTTLWRRNA NGDPVCNACGLYYKLHNINRPLTMKKEGIQTRNRKMS SKSKKCKKVHDSLEDFPKNSSFNPAALSRHMSSLSHI SPFSHSSHMLTTPTPMHPPSSLSFGPHHPSSMVTAMG (SEQ ID NO: 6) | Gene ID: 2625 |
| HOXB7 (Homeobox B7) | >NP_004493.3 homeobox protein Hox-B7 [*Homo sapiens*] MSSLYYANTLFSKYPASSSVFATGAFPEQTSCAFASN PQRPGYGAGSGASFAASMQGLYPGGGGMAGQSA AGVYAAGYGLEPSSFNMHCAPFEQNLSGVCPGDSAKA AGAKEQRDSDLAAESNFRIYPWMRSSGTDRKRG RQTYTRYQTLELEKEFHYNRYLTRRRRIEIAHTLCLT ERQIKIWFQNRRMKWKKENKTAGPGTTGQDRAE AEEEEEE (SEQ ID NO: 7) | Gene ID: 3217 |

TABLE 1-continued

| UB Markers | | |
|---|---|---|
| Marker Name | Exemplary Protein Sequences | NCBI Gene ID |
| EMX2 (Empty Spiracles Homeobox 2) | >NP_001159396.1 homeobox protein EMX2 isoform 2 [*Homo sapiens*] MFQPAPKRCFTIESLVAKDSPLPASRSEDPIRPAALS YANSSPINPFLNGFHSAAAAAAGRGVYSNPDLV FAEAVSHPPNPAVPVHPVPPPHALAAHPLPSSHSPHP LFASQQRDPSTFYPWLIHRYRYLGHRFQGKSMV SEPKNKVQKAEAGGRRLRFATKEKRDAPY (SEQ ID NO: 8) | Gene ID: 2018 |
| PAX2 (Paired box 2) | >NP_003978.3 paired box protein Pax-2 isoform a [*Homo sapiens*] MDMHCKADPFSAMHPGHGGVNQLGGVFVNGRPLPDVV RQRIVELAHQGVRPCDISRQLRVSHGCVSKILGRYYE TGSIKPGVIGGSKPKVATPKVVDKIAEYKRQNPTMFA WEIRDRLLAEGICDNDTVPSVSSINRIIRTKVQQPFH PTPDGAGTGVTAPGHTIVPSTASPPVSSASNDPVGSY SINGILGIPRSNGEKRKRDEVEVYTDPAHIRGGGGLH LVWTLRDVSEGSVPNGDSQSGVDSLRKHLRADTFTQQ QLEALDRVFERPSYPDVFQASEHIKSEQGNEYSLPAL TPGLDEVKSSLSASTNPELGSNVSGTQTYPVVTGRDM ASTTLPGYPPHVPPTGQGSYPTSTLAGMVPGSEFSGN PYSHPQYTAYNEAWRFSNPALLSSPYYYSAAPRGSAP AAAAAAYDRH (SEQ ID NO: 9) | Gene ID: 5076 |
| WNT11 (Wnt family member 11) | >NP_004617.2 protein Wnt-11 precursor [*Homo sapiens*] MRARPQVCEALLFALALQTGVCYGIKWLALSKTPSAL ALNQTQHCKQLEGLVSAQVQLCRSNLELMHTVV HAAREVMKACRRAFADMRWNCSSIELAPNYLLDLERG TRESAFVYALSAAAISHAIARACTSGDLPGCSC GPVPGEPPGPGNRWGGCADNLSYGLLMGAKFSDAPMK VKKTGSQANKLMRLHNSEVGRQALRASLEMKCK CHGVSGSCSIRTCWKGLQELQDVAADLKTRYLSATKV VHRPMGTRKHLVPKDLDIRPVKDSELVYLQSSP DFCMKNEKVGSHGTQDRQCNKTSNGSDSCDLMCCGRG YNPYTDRVVERCHCKYHWCCYVTCRRCERTVER YVCK (SEQ ID NO: 10) | Gene ID: 7481 |
| CDH1 (Cadherin 1) | >NP_004351.1 cadherin-1 isoform 1 preproprotein [*Homo sapiens*] MGPWSRSLSALLLLLQVSSWLCQEPEPCHPGFDAESY TFTVPRRHLERGRVLGRVNFEDCTGRQRTAYFS LDTRFKVGTDGVITVKRPLRFHNPQIHFLVYAWDSTY RKFSTKVTLNTVGHHHRPPPHQASVSGIQAELL TFPNSSPGLRRQKRDWVIPPISCPENEKGPFPKNLVQ IKSNKDKEGKVFYSITGQGADTPPVGVFIIERE TGWLKVTEPLDRERIATYTLFSHAVSSNGNAVEDPME ILITVTDQNDNKPEFTQEVFKGSVMEGALPGTS VMEVTATDADDDVNTYNAAIAYTILSQDPELPDKNMF TINRNTGVISVVTTGLDRESFPTYTLVVQAADL QGEGLSTTATAVITVTDTNDNPPIFNPTTYKGQVPEN EANVVITTLKVTDADAPNTPAWEAVYTILNDDG GQFVVTTNPVNNDGILKTAKGLDFEAKQQYILHVAVT NVVPFEVSLTTSTATVTVDVLDVNEAPIFVPPE KRVEVSEDFGVGQEITSYTAQEPDTFMEQKITYRIWR DTANWLEINPDTGAISTRAELDREDFEHVKNST YTALIIATDNGSPVATGTGTLLLILSDVNDNAPIPEP RTIFFCERNPKPQVINIIDADLPPNTSPFTAEL THGASANWTIQYNDPTQESIILKPKMALEVGDYKINL KLMDNQNKDQVTTLEVSVCDCEGAAGVCRKAQP VEAGLQIPAILGILGGILALLILILLLLLFLRRRAVV KEPLLPPEDDTRDNVYYYDEEGGGEEDQDFDLS QLHRGLDARPEVTRNDVAPTLMSVPRYLPRPANPDEI GNFIDENLKAADTDPTAPPYDSLLVFDYEGSGS EAASLSSLNSSESDKDQDYDYLNEWGNRFKKLADMYG GGEDD (SEQ ID NO: 11) | Gene ID: 999 |
| HNF1B (HNF1 Homeobox B) | >KAI4049074. 1 HNF1 homeobox B [*Homo sapiens*] MVSKLTSLQQELLSALLSSGVTKEVLVQALEELLPSP NFGVKLETLPLSPGSGAEPDTKPVFHTLTNGHA KGRLSGDEGSEDGDDYDTPPILKELQALNTEEAAEQR AEVDRMLSEDPWRAAKMIKGYMQQHNIPQREVV DVTGLNQSHLSQHLNKGTPMKTQKRAALYTWYVRKQR EILRQFNQTVQSSGNMTDKSSQDQLLFLFPEFS QQSHGPGQSDDACSEPTNKKMRRNRFKWGPASQQILY | Gene ID: 6928 |

TABLE 1-continued

| UB Markers | | |
|---|---|---|
| Marker Name | Exemplary Protein Sequences | NCBI Gene ID |
| | QAYDRQKNPSKEEREALVEECNRAECLQRGVSP SKAHGLGSNLVTEVRVYNWFANRRKEEAFRQKLAMDA YSSNQTHSLNPLLSHGSPHHQPSSSPPNKLSGV RYSQQGNNEITSSSTISHHGNSAMVTSQSVLQQVSPA SLDPGHNLLSPDGKMDLSLRRRFAPSQHLDEYP QPLPP (SEQ ID NO: 12) | |

During the step-wise differentiation of pluripotent stem cells to Wolffian Duct progenitors, upregulation of PAX2, FMX2, LHX1, RET1, CXCR4, cKit, and HOXB7 are expressed. As the Wolffian Duct matures and transitions to the UB, notable upregulation of WNT11, HNF1b, ECAD, and CALB1 expression orchestrates UB bud formation.

Provided herein are methods of arranging UB kidney tissues in a sequential configuration and in a proximity sufficient to form fused UB kidney tissues that are contiguously fused from at least one connecting point. In some embodiments, the sequential configuration comprises a linear pattern or a circular pattern. In some embodiments, the UB kidney tissues are arranged in the branching medium provided herein. In some embodiments, the UB kidney tissues are cultured in static conditions without shaking or stirring. In some embodiments, the UB kidney tissues are cultured under shaking conditions. In some embodiments, the UB kidney tissues are cultured under stirring conditions.

The at least one connecting point between UB kidney tissues can comprise a tip of a UB kidney tissue of the plurality of UB kidney tissues. In some embodiments, a tip is about 0.1 micrometer (μm) in size or more, 1 μm or more, 2 μm or more, 3 μm or more, 4 μm or more, 5 μm or more, 6 μm or more, 7 μm or more, 8 μm or more, 9 μm or more, 10 μm or more, 15 μm or more, up to 20 μm in size. In some embodiments, a connecting point between UB kidney tissues comprises one or more tips of an adjacent UB kidney tissue of the plurality of UB kidney tissues. In some embodiments, a connecting point between UB kidney tissues comprises two or more tips of adjacent UB kidney tissues of the plurality of UB kidney tissues. In some embodiments, a tip provided herein comprises a RET1 marker or a SOX9 marker.

The at least one connecting point between UB kidney tissues can comprise a stalk of a UB kidney tissue of the plurality of UB kidney tissues. In some embodiments, a stalk is about 1 micrometer (μm) in size or more, 5 μm or more, 10 μm or more, 11 μm or more, 12 μm or more, 13 μm or more, 14 μm or more, 15 μm or more, 20 μm or more, 25 μm or more, 30 μm or more, 35 μm or more, 40 μm or more, 45 μm or more, 50 μm or more, 55 μm or more, 60 μm or more, 65 μm or more, 70 μm or more, 75 μm or more, 80 μm or more, 85 μm or more, 90 μm or more, 95 μm or more, 100 μm or more, 125 μm or more, 150 μm or more, up to 200 μm in size. In some embodiments, a connecting point between UB kidney tissues comprises one or more stalks of an adjacent UB kidney tissue of the plurality of UB kidney tissues. In some embodiments, a connecting point between UB kidney tissues comprises two or more stalks of adjacent UB kidney tissues of the plurality of UB kidney tissues. In some embodiments, a stalk provided herein comprises a CK8 marker.

In some embodiments, the UB kidney tissues have a core. In some embodiments, a portion of a core comprises epithelial cells. In some embodiments, a portion of a core comprises renal stromal cells. In some embodiments, a portion of a core of the UB kidney tissues comprises epithelial cells and renal stromal cells.

In some embodiments, the UB kidney tissues are sequentially configured in a linear pattern. In some embodiments, the UB kidney tissues are lumenized. In some embodiments, the UB kidney tissues are cylindrical or tubular in architecture. In some embodiments, the lumenized UB kidney tissue is hollow in the center. In some embodiments, the UB kidney tissues comprise an architecture that facilitates fluid flow. In some embodiments, the architecture that facilitates fluid flow comprises a tubular shape that is hollow in the center. In some embodiments, a portion of a core of the lumen of the UB kidney tissues comprise epithelial cells. In some embodiments, a portion of the lumen of the UB kidney tissues comprise renal stromal cells. In some embodiments, a portion of the lumen of the UB kidney tissues comprise epithelial cells and renal stromal cells.

In some embodiments, the lumenized kidney tissues provided herein are at least about 1 millimeter (mm) in diameter. In some embodiments, the lumenized kidney tissues provided herein are at least about 5 mm in diameter. In some embodiments, the lumenized kidney tissues provided herein are at least about 10 mm in diameter. In some embodiments, the lumenized kidney tissues provided herein are at least about 15 mm in diameter. In some embodiments, the lumenized kidney tissues provided herein are at least about 20 millimeters mm in diameter. In some embodiments, the lumenized kidney tissues provided herein are at least about 25 millimeters mm in diameter.

In some embodiments, the lumenized kidney tissues provided herein are at least about 10 mm long. In some embodiments, the lumenized kidney tissues provided herein are at least about 15 mm long. In some embodiments, the lumenized kidney tissues provided herein are at least about 20 mm long. In some embodiments, the lumenized kidney tissues provided herein are at least about 25 mm long. In some embodiments, the lumenized kidney tissues provided herein are at least about 50 mm long. In some embodiments, the lumenized kidney tissues provided herein are at least about 75 mm long. In some embodiments, the lumenized kidney tissues provided herein are at least about 100 mm long. In some embodiments, the lumenized kidney tissues provided herein are at least about 125 mm long. In some embodiments, the lumenized kidney tissues provided herein are at least about 150 mm long. In some embodiments, the lumenized kidney tissues provided herein are at least about 175 mm long. In some embodiments, the lumenized kidney tissues provided herein are at least about 200 mm long. In some embodiments, the lumenized kidney tissues provided herein are at least about 250 mm long. In some embodiments, the lumenized kidney tissues provided herein are at least about 300 mm long. In some embodiments, the lumenized kidney tissues provided herein are at least about 350 mm long. In some embodiments, the lumenized kidney tissues provided herein are at least about 400 mm long. In some embodiments, the lumenized kidney tissues provided herein are at least about 450 mm long. In some embodiments, the lumenized kidney tissues provided herein are at least about 500 mm long.

In some embodiments, the UB kidney tissues are exposed to flow conditions that generate shear stress on the cells in the UB kidney tissues. In some embodiments, flow conditions can be implemented by applying fluid perfusion to the UB kidney tissues. In some embodiments, fluid perfusion is applied in closed-loop or open-loop flow systems.

In some embodiments, the fluid perfusion comprises a flow rate that is selected to create a desired shear stress. For a rectangular channel with a width w and height h, and a fluid with a viscosity $\eta$, the wall shear stress $\tau$ and flow rate Q have the following relationship: $\tau=6\eta Q/h^2w$. For a cylindrical channel with a radial distance r, and a fluid with a viscosity $\eta$, the wall shear stress $\tau$ and flow rate Q have the following relationship: $\tau=4\eta Q/r^3\pi$. In some embodiments, the flow rate is controlled to vary over time. In some embodiments, the flow rate is controlled to vary at different locations along the UB kidney tissues.

In some embodiments, the selected flow rate may generate shear stress anywhere from about 0.000001 dyn/cm$^2$ to about 100 dyn/cm$^2$, from about 0.01 dyn/cm$^2$ to about 50 dyn/cm$^2$, from about 0.01 dyn/cm$^2$ to about 10 dyn/cm$^2$, from about 0.01 dyn/cm$^2$ to about 5 dyn/cm$^2$, or from about 0.01 dyn/cm$^2$ to about 1 dyn/cm$^2$. In some embodiments, the selected flow rate may generate shear stress is about 0.1 up to 10 dyn/cm$^2$. In some embodiments, the selected flow rate may generate shear stress is about 10 up to 20 dyn/cm$^2$. The exposure to shear stress can be constant, continuous, or intermittent and can be for anywhere from 1 day to 200 days. In some embodiments, shear stress may also be pulsed to mimic blood pressure changes during regular heartbeats. The terms "constant" and "continuous" and "laminar" can be used interchangeably and refer to an uninterrupted and/or steady exposure to shear stress for a specified and extended period of time (e.g., from 1 to 200 days). The term "intermittent" refers to an interrupted or unsteady exposure to shear stress. In reference to the intermittent exposure, the UB kidney tissues can be exposed to shear stress in regular intervals, e.g., every 5 seconds, every 10 seconds, or every 15 seconds, etc., for a specified amount of time of exposure, e.g., for 1 second, for 2 seconds, for 3 seconds, for 4 seconds, for 5 seconds, etc., for a specified time period (e.g., from 1 to 200 days). In some embodiments, the UB kidney tissues can be exposed to shear stress in irregular intervals. The type of exposure to the shear stress can be pre-programmed.

(2) Nephron Kidney Tissues and Methods of Making the Same.

Provided herein are nephron kidney tissues. In some embodiments, the nephron kidney tissues provided herein comprise primary nephron cells. In some embodiments, the nephron kidney tissues comprise nephron progenitor cells (NPCs). Nephron progenitor cells (NPCs) self-renew and differentiate into nephrons, the functional units of the kidney. In mammals, each kidney contains about a million nephrons, which are each made up of a glomerulus and a renal tubule. The glomerulus filters waste and excess fluid from the blood, creating primary urine. The renal tubule returns some electrolytes back to the blood via reabsorption and removes waste. Reabsorption is either passive, due to diffusion, or active, due to pumping against a concentration gradient. Substances reabsorbed include: water, sodium chloride, glucose, amino acids, lactate, magnesium, calcium phosphate, uric acid, and bicarbonate. Secretion also occurs in the tubules and collecting duct. Substances secreted in the renal tubules and collecting duct include urea, creatinine, potassium, hydrogen, and uric acid. A countercurrent system in the renal medulla provides the mechanism for generating a hypertonic interstitium, which allows the recovery of solute-free water from within the nephron and returning it to the venous vasculature when appropriate. While nephron progenitor cells have been differentiated from stem cells, current protocols and assays have not shown whether these cells can be recombined with ureteric bud cells or lumenized kidney tissues to form a fully functioning nephron comprising a complete nephron, with markers of the glomerulus and each primary portion of the renal tubule (the proximal convoluted tubule, the loop of Henle, the distal convoluted tubule), connected to the distal nephron and collecting duct. The inventors have recognized and appreciated that nephron progenitor cells when recombined with UB stalks and tips produced by the methods described herein form a kidney tissue comprising markers of each portion of a nephron and ureteric epithelium and have the structural morphology characteristic of developing and mature nephrons. The kidney tissues also form repeating units of nephric-ureteric bud connections that have not previously been achieved by other methods.

Figure 1B:
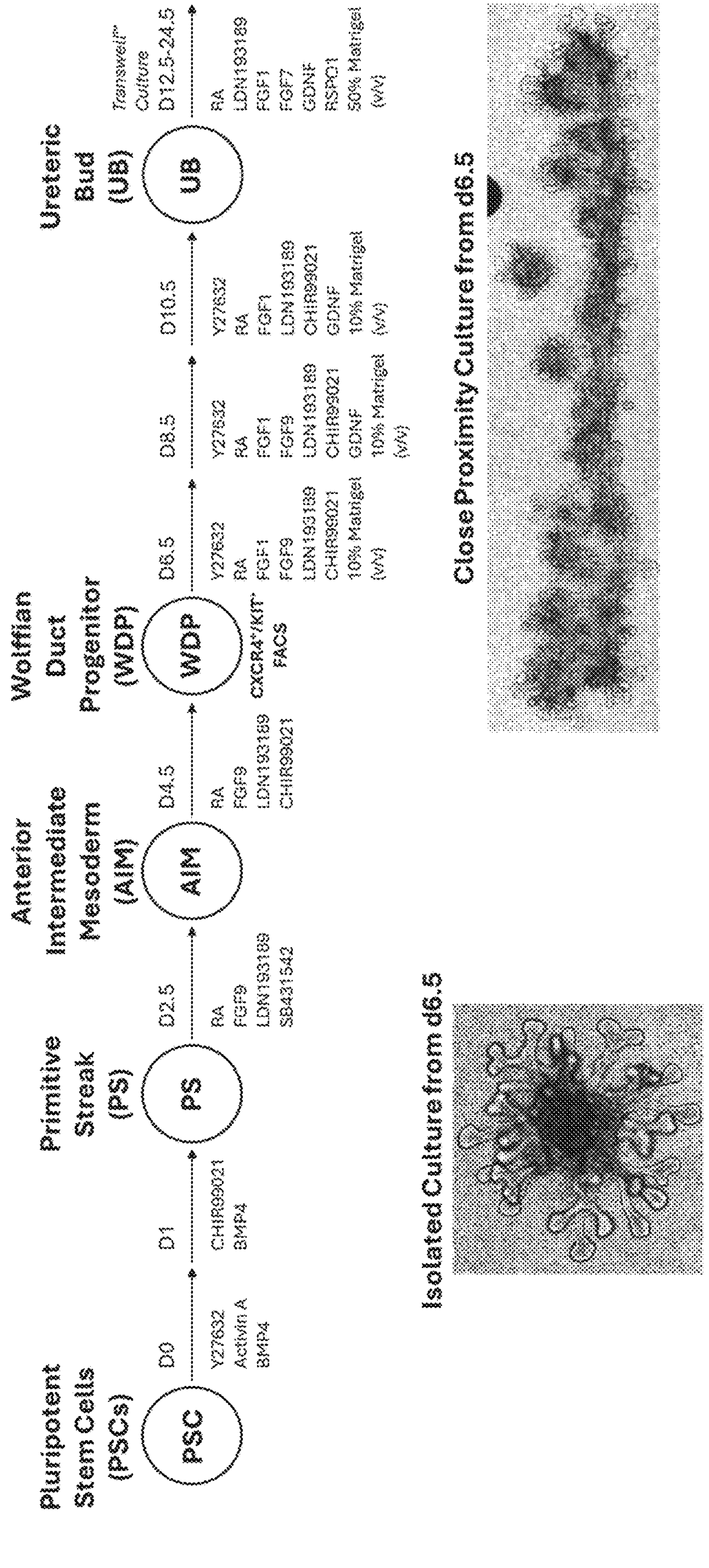
Figure 1C:
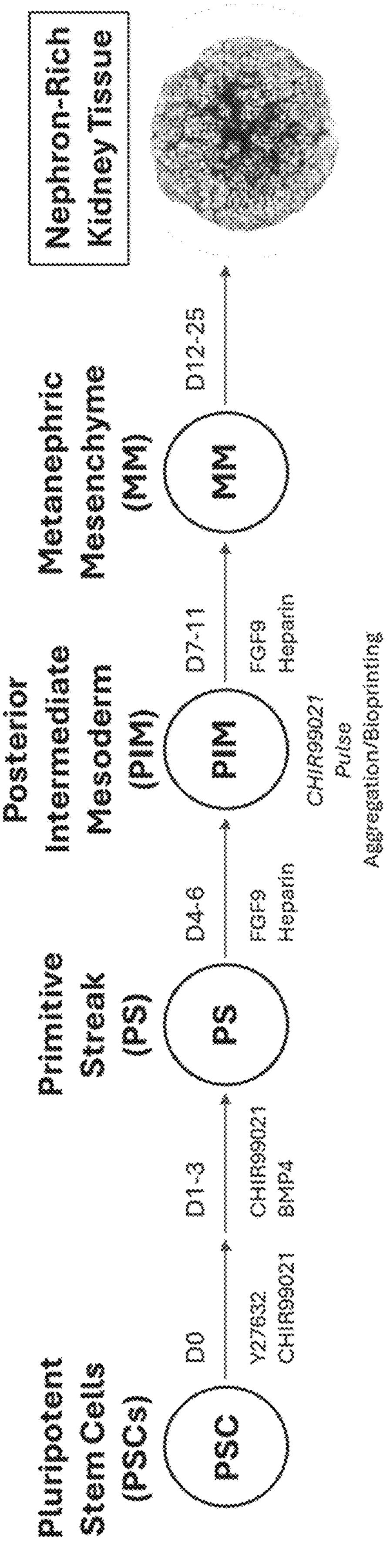

Provided herein are methods of generating nephron kidney tissues, wherein the methods comprise contacting a population of human induced pluripotent stem cells (iPSCs) with a first cell culture medium for a period of time to form nephron progenitor cells (NPCs). FIG. 1C provides an exemplary timeline for nephron progenitor cell differentiation and maturation. Stem cells, nephron progenitor cells, or posterior intermediate mesoderm cells can be from any source or species. In some embodiments, the nephron kidney tissues comprise posterior intermediate mesoderm cells or differentiated progeny thereof. In some embodiments, the NPCs are derived from a population of stem cells. In some embodiments, the NPCs are derived from human induced pluripotent stem cells (iPSCs), embryonic stem cells, or adult stem cells. Methods of differentiating NPCs are described, for example, in Huang et al., *Cell Stem Cell,* 2024, the contents of which is incorporated herein by reference in its entirety.

A cell culture medium provided herein can comprise a basal medium supplemented with one or more growth factors, metabolites, antioxidants, antigens, small molecules, and/or proteins that permit differentiation of a stem cell to a nephron progenitor cell or an NPC. In some embodiments, the cell culture medium comprises a basal differentiation medium (DM). In some embodiments, the cell culture medium comprises serum. In some embodiments, the serum is fetal bovine serum (FBS). In some embodiments, the cell culture medium is serum-free cell culture medium. In some embodiments, the cell culture medium comprises a basal medium, wherein the basal medium comprises Dulbecco's Modified Eagle Medium/Nutrient Mixture F-12 (DMEM/F21). In some embodiments, the cell culture medium comprises an antigen. In some embodiments, the cell culture medium comprises a B27 supplement. In some embodiments, the cell culture medium comprises a retinoic acid receptor agonist. In some embodiments, the cell culture medium comprises retinoic acid. In some embodiments, the cell culture medium does not comprise retinoic acid. In some embodiments, the cell culture medium comprises insulin-transferrin-selenium (ITS). In some embodiments, the cell culture medium comprises non-essential amino acids (NEAA). In some embodiments, the cell culture medium comprises L-glutamine. In some embodiments, the cell culture medium comprises an antibiotic. In some embodiments, the cell culture medium comprises penicillin and/or streptomycin. In some embodiments, the cell culture medium comprises an antioxidant. In some embodiments, the cell culture medium comprises 2-mercaptoethanol. In some embodiments, the cell culture medium comprises: a Rho kinase (ROCK) inhibitor. In some embodiments, the Rho kinase (ROCK) inhibitor comprises: Y27632 Y30141, Y33075, Y39983, or any combination thereof. In some embodiments, the cell culture medium comprises an activin receptor ligand (e.g., Activin A). In some embodiments, the cell culture medium does not comprise an activin receptor ligand (e.g., Activin A). In some embodiments, the cell culture medium comprises: a transforming growth factor β receptor family ligand. In some embodiments, the growth factor comprises BMP1, BMP2, BMP3, BMP4, BMP5, BMP6, BMP7, BMP8, BMP9, BMP10, fibroblast growth factor (FGF), epidermal growth factor (EGF), hedgehog molecules, insulin-like growth factor (IGF), platelet-derived growth factor (PDGF), VEGF, or a WNT molecule. In some embodiments, the cell culture medium comprises: BMP4. In some embodiments, the cell culture medium comprises an ALK inhibitor. In some embodiments, the ALK inhibitor comprises LDN193189 and/or A 83-01 (3-(6-Methyl-2-pyridinyl)-N-phenyl-4-(4-quinolinyl)-1H-pyrazole-1-carbothioamide, CAS No. 909910-43-6). In some embodiments, the cell culture medium comprises a WNT pathway activator. In some embodiments, the WNT pathway activator comprises a glycogen synthase kinase 3 inhibitor. In some embodiments, the cell culture medium does not comprise a glycogen synthase kinase 3 inhibitor. In some embodiments, the glycogen synthase kinase 3 inhibitor comprises a small molecule selected from the group consisting of: CHIR98014, CHIR98024, CHIR99021, 2,4'-dibromoacetophenone, and dihydronarwedine. In some embodiments, the cell culture medium comprises A-77-01, EW-7197, GW 788388, LDN-193189, LDN-214117, SB-431542, SB-505124, SB-202190, or SM-16. In some embodiments, the cell culture medium comprises a fibroblast growth factor (FGF). In some embodiments, the FGF comprises FGF1, FGF2, FGF3, FGF4, FGF5, FGF6, FGF7, FGF8, FGF9, FGF10, FGF16, FGF17, FGF18, FGF19, FGF20, FGF21, FGF22, FGF23, or any combination thereof. In some embodiments, the cell culture medium comprises FGF2. In some embodiments, a cell culture medium comprises a glial cell line-derived neurotrophic factor (GDNF) or a tumor growth factor (e.g., TGF-beta 2). In some embodiments, the cell culture medium comprises a gamma-secretase inhibitor. In some embodiments, the gamma-secretase inhibitor comprises (2S)—N-[(3,5-Difluorophenyl)acetyl]-L-alanyl-2-phenyl]glycine 1,1-dimethylethyl ester (DAPT, Cas 208255-80-5), N—[N-(3,5-difluorophenacetyl)-L-alanyl]-S-phenylglycine t-butyl ester (Mk 0752, CAS No.: 471905-41-6), or N1-[(7S)-6,7-dihydro-6-oxo-5H-dibenz[b,d]azepin-7-yl]-2,2-dimethyl-N3-(2,2,3,3,3-pentafluoropropyl)-propanediamide (Ro4929097, CAS No. 847925-91-1). In some embodiments, a cell culture medium provided herein comprises a large tumor suppressor kinase (LATS) inhibitor. In some embodiments, the LATS inhibitor comprises N-[3-(phenylmethyl)-2(3H)-thiazolylidene]-1H-pyrrolo[2,3-b]pyridine-3-carboxamide (TRULI, Cas No. 1424635-83-5).

The human induced pluripotent stem cells, posterior intermediate mesoderm cells, and/or NPCs provided herein can be cultured under conditions that permit growth, maintenance, survival, and/or differentiation of the cells for use in generating an in vitro-differentiated kidney or kidney tissue provided herein. Cells can be cultured in an incubator or a bioreactor that maintains temperature, $CO_2$ levels, oxygen levels, and humidity. In general, cells are cultured at between about 35 degrees Celsius to about 38 degrees Celsius, at approximately 5% CO2 level, and approximately 95% humidity, unless otherwise indicated. The cells provided herein can be cultured for a period of time that permits differentiation of one progenitor cell type to another cell type.

The human induced pluripotent stem cells, posterior intermediate mesoderm cells, and/or NPCs provided herein can be in contact with an extracellular matrix that supports cellular structure, differentiation, growth, and survival. In some embodiments, the extracellular matrix is on a solid support, such as a cell culture dish or a tube. In some embodiments, the extracellular matrix is in suspension with the cells provided herein. In some embodiments, the extracellular matrix comprises: extracellular matrix comprises a solubilized basement membrane preparation extracted from Engelbreth-Holm-Swarm (EHS) mouse sarcoma, laminin, collagen IV, heparan sulfate proteoglycans, entactin, fibronectin, vitronectin, retronectin, elastin, hyaluronic acid, methylcellulose, a gelatin, or any combination thereof.

In some embodiments, the human induced pluripotent stem cells, posterior intermediate mesoderm cells, or NPCs are cultured in suspension culture at about 37 degrees C. with about 5% $CO_2$ and about 95% relative humidity for at least 8 hours, at least 12 hours, at least 20 hours, at least 24 hours, at least 36 hours, or at least 48 hours. In some embodiments, the human iPSCs or human iPSC aggregates are cultured at 38 degrees C. with 5% $CO_2$ and 95% relative humidity for at least 8 hours, at least 12 hours, at least 20 hours, at least 24 hours, at least 36 hours, or at least 48 hours.

In some embodiments, the human induced pluripotent stem cells, posterior intermediate mesoderm cells, Wolffian duct progenitor cells, and/or NPCs provided herein are enriched for or sorted for SIX2, Integrin alpha-8 (ITGA8), CITED1, PAX2, CXCR4, cKit, or any combination thereof. In some embodiments, the cells are isolated using flow cytometry techniques.

Provided herein are nephron kidney tissues comprising one or more nephron markers. A nephron marker can comprise a surface marker, a genomic marker, a protein, an RNA, a DNA, or a cDNA that is present in, expressed by, or presented by a nephron or NPC kidney tissue provided herein. In some embodiments, the nephron marker comprises or expresses a marker selected from the group consisting of: a homeobox gene or protein, a paired box gene or protein, an integrin gene or protein, a Cbp/p300 interacting transactivator gene or protein, a low-density lipoprotein receptor-related protein gene or protein, a MAF bZIP transcription factor B gene or protein, and any combination thereof. In some embodiments, the nephron marker is a marker provided in Table 2, an ortholog, a homolog, or a variant thereof (e.g., an alternative splice variant or a mutant).

TABLE 2

Nephron Markers.

| Marker Name | Exemplary Protein Sequences | NCBI Gene ID |
|---|---|---|
| SIX2 (SIX homeobox 2) | >NP_058628.3 homeobox protein SIX2 [*Homo sapiens*]<br>MSMLPTFGFTQEQVACVCEVLQQGGNIERLGRFLWSL<br>PACEHLHKNESVLKAKAVVAFHRGNFRELYKILESHQ<br>FSPHNHAKLQQLWLKAHYIEAEKLRGRPLGAVGKYRV<br>RRKFPLPRSIWDGEETSYCFKEKSRSVLREWYAHNPY<br>PSPREKRELAEATGLTTTQVSNWFKNRRQRDRAAEAK<br>ERENNENSNSNSHNPLNGSGKSVLGSSEDEKTPSGTP<br>DHSSSSPALLLSPPPPGLPSLHSLGHPPGPSAVPVPV<br>PGGGGADPLQHHHGLQDSILNPMSANLVDLGS (SEQ ID NO: 13) | Gene ID: 10736 |
| PAX2 (Paired box 2) | >NP_003978.3 paired box protein Pax-2 isoform a [*Homo sapiens*]<br>MDMHCKADPFSAMHPGHGGVNQLGGVFVNGRPLPDVV<br>RQRIVELAHQGVRPCDISRQLRVSHGCVSKILGRYYE<br>TGSIKPGVIGGSKPKVATPKVVDKIAEYKRQNPTMFA<br>WEIRDRLLAEGICDNDTVPSVSSINRIIRTKVQQPFH<br>PTPDGAGTGVTAPGHTIVPSTASPPVSSASNDPVGSY<br>SINGILGIPRSNGEKRKRDEVEVYTDPAHIRGGGGLH<br>LVWTLRDVSEGSVPNGDSQSGVDSLRKHLRADTFTQQ<br>QLEALDRVFERPSYPDVFQASEHIKSEQGNEYSLPAL<br>TPGLDEVKSSLSASTNPELGSNVSGTQTYPVVTGRDM<br>ASTTLPGYPPHVPPTGQGSYPTSTLAGMVPGSEFSGN<br>PYSHPQYTAYNEAWRFSNPALLSSPYYYSAAPRGSAP<br>AAAAAAYDRH (SEQ ID NO: 9) | Gene ID: 5076 |
| ITGA8 (integrin alpha 8) | >NP_003629.2 integrin alpha-8 isoform 1 preproprotein [*Homo sapiens*]<br>MSPGASRGPRGSQAPLIAPLCCAAAALGMLLWSPACQ<br>AFNLDVEKLTVYSGPKGSYFGYAVDFHIPDARTASVL<br>VGAPKANTSQPDIVEGGAVYYCPWPAEGSAQCRQIPF<br>DTTNNRKIRVNGTKEPIEFKSNQWFGATVKAHKGKVV<br>ACAPLYHWRTLKPTPEKDPVGTCYVAIQNFSAYAEFS<br>PCRNSNADPEGQGYCQAGFSLDFYKNGDLIVGGPGSF<br>YWQGQVITASVADIIANYSFKDILRKLAGEKQTEVAP<br>ASYDDSYLGYSVAAGEFTGDSQQELVAGIPRGAQNFG<br>YVSIINSTDMTFIQNFTGEQMASYFGYTVVVSDVNSD<br>GLDDVLVGAPLFMEREFESNPREVGQIYLYLQVSSLL<br>FRDPQILTGTETFGRFGSAMAHLGDLNQDGYNDIAIG<br>VPFAGKDQRGKVLIYNGNKDGLNTKPSQVLQGVWASH<br>AVPSGFGFTLRGDSDIDKNDYPDLIVGAFGTGKVAVY<br>RARPVVTVDAQLLLHPMIINLENKTCQVPDSMTSAAC<br>FSLRVCASVTGQSIANTIVLMAEVQLDSLKQKGAIKR<br>TLFLDNHQAHRVFPLVIKRQKSHQCQDFIVYLRDETE<br>FRDKLSPINISLNYSLDESTFKEGLEVKPILNYYREN<br>IVSEQAHILVDCGEDNLCVPDLKLSARPDKHQVIIGD<br>ENHLMLIINARNEGEGAYEAELFVMIPEEADYVGIER<br>NNKGFRPLSCEYKMENVTRMVVCDLGNPMVSGTNYSL<br>GLRFAVPRLEKTNMSINFDLQIRSSNKDNPDSNFVSL<br>QINITAVAQVEIRGVSHPPQIVLPIHNWEPEEEPHKE<br>EEVGPLVEHIYELHNIGPSTISDTILEVGWPFSARDE<br>FLLYIFHIQTLGPLQCQPNPNINPQDIKPAASPEDTP<br>ELSAFLRNSTIPHLVRKRDVHVVEFHRQSPAKILNCT<br>NIECLQISCAVGRLEGGESAVLKVRSRLWAHTFLQRK<br>NDPYALASLVSFEVKKMPYTDQPAKLPEGSIVIKTSV<br>IWATPNVSFSIPLWVIILAILLGLLVLAILTLALWKC<br>GFFDRARPPQEDMTDREQLTNDKTPEA (SEQ ID NO: 21) | Gene ID: 8516 |
| CITED 1 (Cbp/p300 interacting transactivator with Glu/Asp rich carboxy-terminal domain 1) | >NP_001138358.1 cbp/p300-interacting transactivator 1 isoform 1 [*Homo sapiens*]<br>MPTTSRPALDVKGGTSPAKEDANQEMSSVAYSNLAVK<br>DRKAVAILHYPGVASNGTKASGAPTSSSGSPIGSPTT<br>TPPTKPPSFNLHPAPHLLASMHLQKLNSQYQGMAAAT<br>PGQPGEAGPLQNWDFGAQAGGAESLSPSAGAQSPAII<br>DSDPVDEEVLMSLVVELGLDRANELPELWLGQNEFDF<br>TADFPSSC (SEQ ID NO: 14) | Gene ID: 4435 |
| LRP2 (low density lipoprotein receptor-related protein 2) | >NP_004516.2 low-density lipoprotein receptor-related protein 2 precursor [*Homo sapiens*]<br>MDRGPAAVACTLLLALVACLAPASGQECDSAHFRCGS<br>GHCIPADWRCDGTKDCSDDADEIGCAVVTCQQGYFKC<br>QSEGQCIPNSWVCDQDQDCDDGSDERQDCSQSTCSSH | Gene ID: 4036 |

TABLE 2-continued

Nephron Markers.

| Marker Name | Exemplary Protein Sequences | NCBI Gene ID |
|---|---|---|
| | QITCSNGQCIPSEYRCDHVRDCPDGADENDCQYPTCE | |
| | QLTCDNGACYNTSQKCDWKVDCRDSSDEINCTEICLH | |
| | NEFSCGNGECIPRAYVCDHDNDCQDGSDEHACNYPTC | |
| | GGYQFTCPSGRCIYQNWVCDGEDDCKDNGDEDGCESG | |
| | PHDVHKCSPREWSCPESGRCISIYKVCDGILDCPGRE | |
| | DENNTSTGKYCSMTLCSALNCQYQCHETPYGGACFCP | |
| | PGYIINHNDSRTCVEFDDCQIWGICDQKCESRPGRHL | |
| | CHCEEGYILERGQYCKANDSFGEASIIFSNGRDLLIG | |
| | DIHGRSFRILVESQNRGVAVGVAFHYHLQRVFWTDTV | |
| | QNKVFSVDINGLNIQEVLNVSVETPENLAVDWVNNKI | |
| | YLVETKVNRIDMVNLDGSYRVTLITENLGHPRGIAVD | |
| | PTVGYLFFSDWESLSGEPKLERAFMDGSNRKDLVKTK | |
| | LGWPAGVTLDMISKRVYWVDSRFDYIETVTYDGIQRK | |
| | TVVHGGSLIPHPFGVSLFEGQVFFTDWTKMAVLKANK | |
| | FTETNPQVYYQASLRPYGVTVYHSLRQPYATNPCKDN | |
| | NGGCEQVCVLSHRTDNDGLGFRCKCTFGFQLDTDERH | |
| | CIAVQNFLIFSSQVAIRGIPFTLSTQEDVMVPVSGNP | |
| | SFFVGIDFDAQDSTIFFSDMSKHMIFKQKIDGTGREI | |
| | LAANRVENVESLAFDWISKNLYWTDSHYKSISVMRLA | |
| | DKTRRTVVQYLNNPRSVVVHPFAGYLFFTDWFRPAKI | |
| | MRAWSDGSHLLPVINTTLGWPNGLAIDWAASRLYWVD | |
| | AYFDKIEHSTFDGLDRRRLGHIEQMTHPFGLAIFGEH | |
| | LFFTDWRLGAIIRVRKADGGEMTVIRSGIAYILHLKS | |
| | YDVNIQTGSNACNQPTHPNGDCSHFCFPVPNFQRVCG | |
| | CPYGMRLASNHLTCEGDPTNEPPTEQCGLFSFPCKNG | |
| | RCVPNYYLCDGVDDCHDNSDEQLCGTLNNTCSSSAFT | |
| | CGHGECIPAHWRCDKRNDCVDGSDEHNCPTHAPASCL | |
| | DTQYTCDNHQCISKNWVCDTDNDCGDGSDEKNCNSTE | |
| | TCQPSQFNCPNHRCIDLSFVCDGDKDCVDGSDEVGCV | |
| | LNCTASQFKCASGDKCIGVTNRCDGVFDCSDNSDEAG | |
| | CPTRPPGMCHSDEFQCQEDGICIPNFWECDGHPDCLY | |
| | GSDEHNACVPKTCPSSYFHCDNGNCIHRAWLCDRDND | |
| | CGDMSDEKDCPTQPFRCPSWQWQCLGHNICVNLSVVC | |
| | DGIFDCPNGTDESPLCNGNSCSDFNGGCTHECVQEPF | |
| | GAKCLCPLGFLLANDSKTCEDIDECDILGSCSQHCYN | |
| | MRGSFRCSCDTGYMLESDGRTCKVTASESLLLLVASQ | |
| | NKIIADSVTSQVHNIYSLVENGSYIVAVDFDSISGRI | |
| | FWSDATQGKTWSAFQNGTDRRVVFDSSIILTETIAID | |
| | WVGRNLYWTDYALETIEVSKIDGSHRTVLISKNLTNP | |
| | RGLALDPRMNEHLLFWSDWGHHPRIERASMDGSMRTV | |
| | IVQDKIFWPCGLTIDYPNRLLYFMDSYLDYMDFCDYN | |
| | GHHRRQVIASDLIIRHPYALTLFEDSVYWTDRATRRV | |
| | MRANKWHGGNQSVVMYNIQWPLGIVAVHPSKQPNSVN | |
| | PCAFSRCSHLCLLSSQGPHFYSCVCPSGWSLSPDLLN | |
| | CLRDDQPFLITVRQHIIFGISLNPEVKSNDAMVPIAG | |
| | IQNGLDVEFDDAEQYIYWVENPGEIHRVKTDGTNRTV | |
| | FASISMVGPSMNLALDWISRNLYSTNPRTQSIEVLTL | |
| | HGDIRYRKTLIANDGTALGVGFPIGITVDPARGKLYW | |
| | SDQGTDSGVPAKIASANMDGTSVKTLFTGNLEHLECV | |
| | TLDIEEQKLYWAVTGRGVIERGNVDGTDRMILVHQLS | |
| | HPWGIAVHDSFLYYTDEQYEVIERVDKATGANKIVLR | |
| | DNVPNLRGLQVYHRRNAAESSNGCSNNMNACQQICLP | |
| | VPGGLFSCACATGFKLNPDNRSCSPYNSFIVVSMLSA | |
| | IRGFSLELSDHSETMVPVAGQGRNALHVDVDVSSGFI | |
| | YWCDFSSSVASDNAIRRIKPDGSSLMNIVTHGIGENG | |
| | VRGIAVDWVAGNLYFTNAFVSETLIEVLRINTTYRRV | |
| | LLKVTVDMPRHIVVDPKNRYLFWADYGQRPKIERSFL | |
| | DCTNRTVLVSEGIVTPRGLAVDRSDGYVYWVDDSLDI | |
| | IARIRINGENSEVIRYGSRYPTPYGITVFENSIIWVD | |
| | RNLKKIFQASKEPENTEPPTVIRDNINWLRDVTIFDK | |
| | QVQPRSPAEVNNNPCLENNGGCSHLCFALPGLHTPKC | |
| | DCAFGTLQSDGKNCAISTENFLIFALSNSLRSLHLDP | |
| | ENHSPPFQTINVERTVMSLDYDSVSDRIYFTQNLASG | |
| | VGQISYATLSSGIHTPTVIASGIGTADGIAFDWITRR | |
| | IYYSDYLNQMINSMAEDGSNRTVIARVPKPRAIVLDP | |
| | CQGYLYWADWDTHAKIERATLGGNFRVPIVNSSLVMP | |
| | SGLTLDYEEDLLYWVDASLQRIERSTLTGVDREVIVN | |
| | AAVHAFGLTLYGQYIYWTDLYTQRIYRANKYDGSGQI | |
| | AMTTNLLSQPRGINTVVKNQKQQCNNPCEQFNGGCSH | |
| | ICAPGPNGAECQCPHEGNWYLANNRKHCIVDNGERCG | |
| | ASSFTCSNGRCISEEWKCDNDNDCGDGSDEMESVCAL | |
| | HTCSPTAFTCANGRCVQYSYRCDYYNDCGDGSDEAGC | |
| | LFRDCNATTEFMCNNRRCIPREFICNGVDNCHDNNTS | |
| | DEKNCPDRTCQSGYTKCHNSNICIPRVYLCDGDNDCG | |
| | DNSDENPTYCTTHTCSSSEFQCASGRCIPQHWYCDQE | |
| | TDCFDASDEPASCGHSERTCLADEFKCDGGRCIPSEW | |

TABLE 2-continued

Nephron Markers.

| Marker Name | Exemplary Protein Sequences | NCBI Gene ID |
| --- | --- | --- |
| | ICDGDNDCGDMSDEDKRHQCQNQNCSDSEFLCVNDRP<br>PDRRCIPQSWVCDGDVDCTDGYDENQNCTRRTCSENE<br>FTCGYGLCIPKIFRCDRHNDCGDYSDERGCLYQTCQQ<br>NQFTCQNGRCISKTFVCDEDNDCGDGSDELMHLCHTP<br>EPTCPPHEFKCDNGRCIEMMKLCNHLDDCLDNSDEKG<br>CGINECHDPSISGCDHNCTDTLTSFYCSCRPGYKLMS<br>DKRTCVDIDECTEMPFVCSQKCENVIGSYICKCAPGY<br>LREPDGKTCRQNSNIEPYLIFSNRYYLRNLTIDGYFY<br>SLILEGLDNVVALDFDRVEKRLYWIDTQRQVIERMFL<br>NKTNKETIINHRLPAAESLAVDWVSRKLYWLDARLDG<br>LFVSDLNGGHRRMLAQHCVDANNTFCFDNPRGLALHP<br>QYGYLYWADWGHRAYIGRVGMDGTNKSVIISTKLEWP<br>NGITIDYTNDLLYWADAHLGYIEYSDLEGHHRHTVYD<br>GALPHPFAITIFEDTIYWTDWNTRTVEKGNKYDGSNR<br>QTLVNTTHRPFDIHVYHPYRQPIVSNPCGTNNGGCSH<br>LCLIKPGGKGFTCECPDDFRTLQLSGSTYCMPMCSST<br>QFLCANNEKCIPIWWKCDGQKDCSDGSDELALCPQRF<br>CRLGQFQCSDGNCTSPQTLCNAHQNCPDGSDEDRLLC<br>ENHHCDSNEWQCANKRCIPESWQCDTFNDCEDNSDED<br>SSHCASRTCRPGQFRCANGRCIPQAWKCDVDNDCGDH<br>SDEPIEECMSSAHLCDNFTEFSCKTNYRCIPKWAVCN<br>GVDDCRDNSDEQGCEERTCHPVGDFRCKNHHCIPLRW<br>QCDGQNDCGDNSDEENCAPRECTESEFRCVNQQCIPS<br>RWICDHYNDCGDNSDERDCEMRTCHPEYFQCTSGHCV<br>HSELKCDGSADCLDASDEADCPTRFPDGAYCQATMFE<br>CKNHVCIPPYWKCDGDDDCGDGSDEELHLCLDVPCNS<br>PNRFRCDNNRCIYSHEVCNGVDDCGDGTDETEEHCRK<br>PTPKPCTEYEYKCGNGHCIPHDNVCDDADDCGDWSDE<br>LGCNKGKERTCAENICEQNCTQLNEGGFICSCTAGFE<br>TNVFDRTSCLDINECEQFGTCPQHCRNTKGSYECVCA<br>DGFTSMSDRPGKRCAAEGSSPLLLLPDNVRIRKYNLS<br>SERFSEYLQDEEYIQAVDYDWDPKDIGLSVVYYTVRG<br>EGSRFGAIKRAYIPNFESGRNNLVQEVDLKLKYVMQP<br>DGIAVDWVGRHIYWSDVKNKRIEVAKLDGRYRKWLIS<br>TDLDQPAAIAVNPKLGLMFWTDWGKEPKIESAWMNGE<br>DRNILVFEDLGWPTGLSIDYLNNDRIYWSDFKEDVIE<br>TIKYDGTDRRVIAKEAMNPYSLDIFEDQLYWISKEKG<br>EVWKQNKFGQGKKEKTLVVNPWLTQVRIFHQLRYNKS<br>VPNLCKQICSHLCLLRPGGYSCACPQGSSFIEGSTTE<br>CDAAIELPINLPPPCRCMHGGNCYFDETDLPKCKCPS<br>GYTGKYCEMAFSKGISPGTTAVAVLLTILLIVVIGAL<br>AIAGFFHYRRTGSLLPALPKLPSLSSLVKPSENGNGV<br>TFRSGADLNMDIGVSGFGPETAIDRSMAMSEDFVMEM<br>GKQPIIFENPMYSARDSAVKVVQPIQVTVSENVDNKN<br>YGSPINPSEIVPETNPTSPAADGTQVTKWNLFKRKSK<br>QTTNFENPIYAQMENEQKESVAATPPPSPSLPAKPKP<br>PSRRDPTPTYSATEDTFKDTANLVKEDSEV (SEQ<br>ID NO: 15) | |
| MAFB (MAF bZIP transcription factor B) | >NP_005452.2 transcription factor<br>MafB [*Homo sapiens*]<br>MAAELSMGPELPTSPLAMEYVNDFDLLKFDVKKEPLG<br>RAERPGRPCTRLQPAGSVSSTPLSTPCSSVPSSPSFS<br>PTEQKTHLEDLYWMASNYQQMNPEALNLTPEDAVEAL<br>IGSHPVPQPLQSFDSFRGAHHHHHHHHPHPHHAYPGA<br>GVAHDELGPHAHPHHHHHHQASPPPSSAASPAQQLPT<br>SHPGPGPHATASATAAGGNGSVEDRFSDDQLVSMSVR<br>ELNRHLRGFTKDEVIRLKQKRRTLKNRGYAQSCRYKR<br>VQQKHHLENEKTQLIQQVEQLKQEVSRLARERDAYKV<br>KCEKLANSGFREAGSTSDSPSSPEFFL (SEQ ID<br>NO: 16) | Gene ID: 9935 |
| NPHS1 (Adhesion molecule, nehprin) | >NP_004637.1 nephrin precursor [*Homo sapiens*]<br>MALGTTLRASLLLLGLLTEGLAQLAIPASVPRGFWAL<br>PENLTVVEGASVELRCGVSTPGSAVQWAKDGLL<br>LGPDPRIPGFPRYRLEGDPARGEFHLHIEACDLSDDA<br>EYECQVGRSEMGPELVSPRVILSILVPPKLLLL<br>TPEAGTMVTWVAGQEYVVNCVSGDAKPAPDITILLSG<br>QTISDISANVNEGSQQKLFTVEATARVTPRSSD<br>NRQLLVCEASSPALEAPIKASFTVNVLFPPGPPVIEW<br>PGLDEGHVRAGQSLELPCVARGGNPLATLQWLK<br>NGQPVSTAWGTEHTQAVARSVLVMTVRPEDHGAQLSC<br>EAHNSVSAGTQEHGITLQVTFPPSAIIILGSAS<br>QTENKNVTLSCVSKSSRPRVLLRWWLGWRQLLPMEET<br>VMDGLHGGHISMSNLTFLARREDNGLTLTCEAF | Gene ID: 4868 |

TABLE 2-continued

Nephron Markers.

| Marker Name | Exemplary Protein Sequences | NCBI Gene ID |
|---|---|---|
| | SEAFTKETFKKSLILNVKYPAQKLWIEGPPEGQKLRA<br>GTRVRLVCLAIGGNPEPSLMWYKDSRTVTESRL<br>PQESRRVHLGSVEKSGSTFSRELVLVTGPSDNQAKFT<br>CKAGQLSASTQLAVQFPPTNVTILANASALRPG<br>DALNLTCVSVSSNPPVNLSWDKEGERLEGVAAPPRRA<br>PFKGSAAARSVLLQVSSRDHGQRVTCRAHSAEL<br>RETVSSFYRLNVLYRPEFLGEQVLVVTAVEQGEALLP<br>VSVSANPAPEAFNWTFRGYRLSPAGGPRHRILS<br>SGALHLWNVTRADDGLYQLHCQNSEGTAEARLRLDVH<br>YAPTIRALQDPTEVNVGGSVDIVCTVDANPILP<br>GMFNWERLGEDEEDQSLDDMEKISRGPTGRLRIHHAK<br>LAQAGAYQCIVDNGVAPPARRLLRLVVRFAPQV<br>EHPTPLTKVAAAGDSTSSATLHCRARGVPNIVFTWTK<br>NGVPLDLQDPRYTEHTYHQGGVHSSLLTIANVS<br>AAQDYALFTCTATNALGSDQTNIQLVSISRPDPPSGL<br>KVVSLTPHSVGLEWKPGFDGGLPQRFCIRYEAL<br>GTPGFHYVDVVPPQATTFTLTGLQPSTRYRVWLLASN<br>ALGDSGLADKGTQLPITTPGLHQPSGEPEDQLP<br>TEPPSGPSGLPLLPVLFALGGLLLLSNASCVGGVLWQ<br>RRLRRLAEGISEKTEAGSEEDRVRNEYEESQWT<br>GERDTQSSTVSTTEAEPYYRSLRDFSPQLPPTQEEVS<br>YSRGFTGEDEDMAFPGHLYDEVERTYPPSGAWG<br>PLYDEVQMGPWDLHWPEDTYQDPRGIYDQVAGDLDTL<br>EPDSLPFELRGHLV (SEQ ID NO: 17) | |
| CUBN (Cubulin) | >NP_001072.2 cubilin precursor [*Homo sapiens*]<br>MMNMSLPFLWSLLTLLIFAEVNGEAGELELQRQKRSI<br>NLQQPRMATERGNLVFLTGSAQNIEFRTGSLGK<br>IKLNDEDLSECLHQIQKNKEDIIELKGSAIGLPQNIS<br>SQIYQLNSKLVDLERKFQGLQQTVDKKVCSSNP<br>CQNGGTCLNLHDSFFCICPPQWKGPLCSADVNECEIY<br>SGTPLSCQNGGTCVNTMGSYSCHCPPETYGPQC<br>ASKYDDCEGGSVARCVHGICEDLMREQAGEPKYSCVC<br>DAGWMFSPNSPACTLDRDECSFQPGPCSTLVQC<br>FNTQGSFYCGACPTGWQGNGYICEDINECEINNGGCS<br>VAPPVECVNTPGSSHCQACPPGYQGDGRVCTLT<br>DICSVSNGGCHPDASCSSTLGSLPLCTCLPGYTGNGY<br>GPNGCVQLSNICLSHPCLNGQCIDTVSGYFCKC<br>DSGWTGVNCTENINECLSNPCLNGGTCVDGVDSFSCE<br>CTRLWTGALCQVPQQVCGESLSGINGSFSYRSP<br>DVGYVHDVNCFWVIKTEMGKVLRITFTFFRLESMDNC<br>PHEFLQVYDGDSSSAFQLGRFCGSSLPHELLSS<br>DNALYFHLYSEHLRNGRGFTVRWETQQPECGGILTGP<br>YGSIKSPGYPGNYPPGRDCVWIVVTSPDLLVTF<br>TFGTLSLEHHDDCNKDYLEIRDGPLYQDPLLGKFCTT<br>FSVPPLQTTGPFARIHFHSDSQISDQGFHITYL<br>TSPSDLRCGGNYTDPEGELFLPELSGPFTHTRQCVYM<br>MKQPQGEQIQINFTHVELQCQSDSSQNYIEVRD<br>GETLLGKVCGNGTISHIKSITNSVWIRFKIDASVEKA<br>SFRAVYQVACGDELTGEGVIRSPFFPNVYPGER<br>TCRWTIHQPQSQVILLNFTVFEIGSSAHCETDYVEIG<br>SSSILGSPENKKYCGTDIPSFITSVYNFLYVTF<br>VKSSSTENHGFMAKFSAEDLACGEILTESTGTIQSPG<br>HPNVYPHGINCTWHILVQPNHLIHLMFETFHLE<br>FHYNCTNDYLEVYDTDSETSLGRYCGKSIPPSLTSSG<br>NSLMLVFVTDSDLAYEGFLINYEAISAATACLQ<br>DYTDDLGTFTSPNFPNNYPNNWECIYRITVRTGQLIA<br>VHFTNFSLEEAIGNYYTDFLEIRDGGYEKSPLL<br>GIFYGSNLPPTIISHSNKLWLKFKSDQIDTRSGFSAY<br>WDGSSTGCGGNLTTSSGTFISPNYPMPYYHSSE<br>CYWWLKSSHGSAFELEFKDFHLEHHPNCTLDYLAVYD<br>GPSSNSHLLTQLCGDEKPPLIRSSGDSMFIKLR<br>TDEGQQGRGFKAEYRQTCENVVIVNQTYGILESIGYP<br>NPYSENQHCNWTIRATTGNTVNYTFLAFDLEHH<br>INCSTDYLELYDGPRQMGRYCGVDLPPPGSTTSSKLQ<br>VLLLTDGVGRREKGFQMQWFVYGCGGELSGATG<br>SFSSPGFPNRYPPNKECIWYIRTDPGSSIQLTIHDFD<br>VEYHSRCNFDVLEIYGGPDFHSPRIAQLCTQRS<br>PENPMQVSSTGNELAIRFKTDLSINGRGFNASWQAVT<br>GGCGGIFQAPSGEIHSPNYPSPYRSNTDCSWVI<br>RVDRNHRVLLNFTDFDLEPQDSCIMAYDGLSSTMSRL<br>ARTCGREQLANPIVSSGNSLFLRFQSGPSRQNR<br>GFRAQFRQACGGHILTSSFDTVSSPRFPANYPNNQNC<br>SWIIQAQPPLNHITLSFTHFELERSTTCARDFV<br>EILDGGHEDAPLRGRYCGTDMPHPITSFSSALTLRFV | Gene ID: 8029 |

TABLE 2-continued

Nephron Markers.

| Marker Name | Exemplary Protein Sequences | NCBI Gene ID |
|---|---|---|
| | SDSSISAGGFHTTVTASVSACGGTFYMAEGIFN<br>SPGYPDIYPPNVECVWNIVSSPGNRLQLSFISFQLED<br>SQDCSRDFVEIREGNATGHLVGRYCGNSFPLNY<br>SSIVGHTLWVRFISDGSGSGTGFQATFMKIFGNDNIV<br>GTHGKVASPFWPENYPHNSNYQWTVNVNASHVV<br>HGRILEMDIEEIQNCYYDKLRIYDGPSIHARLIGAYC<br>GTQTESFSSTGNSLTFHFYSDSSISGKGFLLEW<br>FAVDAPDGVLPTIAPGACGGFLRTGDAPVFLFSPGWP<br>DSYSNRVDCTWLIQAPDSTVELNILSLDIESHR<br>TCAYDSLVIRDGDNNLAQQLAVLCGREIPGPIRSTGE<br>YMFIRFTSDSSVTRAGFNASFHKSCGGYLHADR<br>GIITSPKYPETYPSNLNCSWHVLVQSGLTIAVHFEQP<br>FQIPNGDSSCNQGDYLVLRNGPDICSPPLGPPG<br>GNGHFCGSHASSTLFTSDNQMFVQFISDHSNEGQGFK<br>IKYEAKSLACGGNVYIHDADSAGYVTSPNHPHN<br>YPPHADCIWILAAPPETRIQLQFEDRFDIEVTPNCTS<br>NYLELRDGVDSDAPILSKFCGTSLPSSQWSSGE<br>VMYLRFRSDNSPTHVGFKAKYSIAQCGGRVPGQSGVV<br>ESIGHPTLPYRDNLFCEWHLQGLSGHYLTISFE<br>DFNLQNSSGCEKDFVEIWDNHTSGNILGRYCGNTIPD<br>SIDTSSNTAVVRFVTDGSVTASGFRLRFESSME<br>ECGGDLQGSIGTFTSPNYPNPNPHGRICEWRITAPEG<br>RRITLMFNNLRLATHPSCNNEHVIVENGIRSNS<br>PQLEKLCSSVNVSNEIKSSGNTMKVIFFTDGSRPYGG<br>FTASYTSSEDAVCGGSLPNTPEGNFTSPGYDGV<br>RNYSRNLNCEWTLSNPNQGNSSISIHFEDFYLESHQD<br>CQFDVLEFRVGDADGPLMWRLCGPSKPTLPLVI<br>PYSQVWIHFVTNERVEHIGFHAKYSFTDCGGIQIGDS<br>GVITSPNYPNAYDSLTHCSSLLEAPQGHTITLT<br>FSDFDIEPHTTCAWDSVTVRNGGSPESPIIGQYCGNS<br>NPRTIQSGSNQLVVTFNSDHSLQGGGFYATWNT<br>QTLGCGGIFHSDNGTIRSPHWPQNFPENSRCSWTAIT<br>HKSKHLEISFDNNFLIPSGDGQCQNSFVKVWAG<br>TEEVDKALLATGCGNVAPGPVITPSNTFTAVFQSQEA<br>PAQGFSASFVSRCGSNFTGPSGYIISPNYPKQY<br>DNNMNCTYVIEANPLSVVLLTFVSFHLEARSAVTGSC<br>VNDGVHIIRGYSVMSTPFATVCGDEMPAPLTIA<br>GPVLLNFYSNEQITDFGFKFSYRIISCGGVFNFSSGI<br>ITSPAYSYADYPNDMHCLYTITVSDDKVIELKF<br>SDFDVVPSTSCSHDYLAIYDGANTSDPLLGKFCGSKR<br>PPNVKSSNNSMLLVFKTDSFQTAKGWKMSFRQT<br>LGPQQGCGGYLTGSNNTFASPDSDSNGMYDKNLNCVW<br>IIIAPVNKVIHLTFNTFALEAASTRQRCLYDYV<br>KLYDGDSENANLAGTFCGSTVPAPFISSGNFLTVQFI<br>SDLTLEREGFNATYTIMDMPCGGTYNATWTPQN<br>ISSPNSSDPDVPFSICTWVIDSPPHQQVKITVWALQL<br>TSQDCTQNYLQLQDSPQGHGNSRFQFCGRNASA<br>VPVFYSSMSTAMVIFKSGVVNRNSRMSFTYQIADCNR<br>DYHKAFGNLRSPGWPDNYDNDKDCTVTLTAPQN<br>HTISLFFHSLGIENSVECRNDFLEVRNGSNSNSPLLG<br>KYCGTLLPNPVFSQNNELYLRFKSDSVTSDRGY<br>EIIWTSSPSGCGGTLYGDRGSFTSPGYPGTYPNNTYC<br>EWVLVAPAGRLVTINFYFISIDDPGDCVQNYLT<br>LYDGPNASSPSSGPYCGGDTSIAPFVASSNQVFIKFH<br>ADYARRPSAFRLTWDS (SEQ ID NO: 18) | |
| SLC12A1 (Solute carrier family 12 member 1) | >NP_000329.2 solute carrier family 12 member 1 isoform A [*Homo sapiens*]<br>MSLNNSSNVFLDSVPSNTNRFQVSVINENHESSAAAD<br>DNTDPPHYEETSFGDEAQKRLRISFRPGNQECY<br>DNFLQSGETAKTDASFHAYDSHTNTYYLQTFGHNTMD<br>AVPKIEYYRNTGSISGPKVNRPSLLEIHEQLAK<br>NVAVTPSSADRVANGDGIPGDEQAENKEDDQAGVVKF<br>GWVKGVLVRCMLNIWGVMLFIRLSWIVGEAGIG<br>LGVLIILLSTMVTSITGLSTSAIATNGFVRGGGAYYL<br>ISRSLGPEFGGSIGLIFAFANAVAVAMYVVGFA<br>ETVVDLLKESDSMMVDPTNDIRIIGSITVVILLGISV<br>AGMEWEAKAQVILLVILLIAIANFFIGTVIPSN<br>NEKKSRGFFNYQASIFAENFGPRFTKGEGFFSVFAIF<br>FPAATGILAGANISGDLEDPQDAIPRGTMLAIF<br>ITTVAYLGVAICVGACVVRDATGNMNDTIISGMNCNG<br>SAACGLGYDFSRCRHEPCQYGLMNNFQVMSMVS<br>GFGPLITAGIFSATLSSALASLVSAPKVFQALCKDNI<br>YKALQFFAKGYGKNNEPLRGYILTFLIAMAFIL<br>IAELNTIAPIISNFFLASYALINFSCFHASYAKSPGW<br>RPAYGIYNMWVSLFGAVLCCAVMFVINWWAAVI | Gene ID: 6557 |

TABLE 2-continued

| Nephron Markers. | | |
|---|---|---|
| Marker Name | Exemplary Protein Sequences | NCBI Gene ID |
| | TYVIEFFLYVYVTCKKPDVNWGSSTQALSYVSALDNA<br>LELTTVEDHVKNFRPQCIVLTGGPMTRPALLDI<br>THAFTKNSGLCICCEVFVGPRKLCVKEMNSGMAKKQA<br>WLIKNKIKAFYAAVAADCFRDGVRSLLQASGLG<br>RMKPNTLVIGYKKNWRKAPLTEIENYVGIIHDAFDFE<br>IGVVIVRISQGFDISQVLQVQEELERLEQERLA<br>LEATIKDNECEEESGGIRGLFKKAGKLNITKTTPKKD<br>GSINTSQSMHVGEFNQKLVEASTQFKKKQEKGT<br>IDVWWLFDDGGLTLLIPYILTLRKKWKDCKLRIYVGG<br>KINRIEEEKIVMASLLSKFRIKFADIHIIGDIN<br>IRPNKESWKVFEEMIEPYRLHESCKDLTTAEKLKRET<br>PWKITDAELEAVKEKSYRQVRLNELLQEHSRAA<br>NLIVLSLPVARKGSISDLLYMAWLEILTKNLPPVLLV<br>RGNHKNVLTFYS (SEQ ID NO: 19) | |
| HNF4A (Hepatocyte nuclear factor 4 alpha) | >NP_849180.1 hepatocyte nuclear factor 4-alpha isoform 1 [*Homo sapiens*]<br>MRLSKTLVDMDMADYSAALDPAYTTLEFENVQVLTMG<br>NDTSPSEGTNLNAPNSLGVSALCAICGDRATGK<br>HYGASSCDGCKGFFRRSVRKNHMYSCRFSRQCVVDKD<br>KRNQCRYCRLKKCFRAGMKKEAVQNERDRISTR<br>RSSYEDSSLPSINALLQAEVLSRQITSPVSGINGDIR<br>AKKIASIADVCESMKEQLLVLVEWAKYIPAFCE<br>LPLDDQVALLRAHAGEHLLLGATKRSMVFKDVLLLGN<br>DYIVPRHCPELAEMSRVSIRILDELVLPFQELQ<br>IDDNEYAYLKAIIFFDPDAKGLSDPGKIKRLRSQVQV<br>SLEDYINDRQYDSRGRFGELLLLLPTLQSITWQ<br>MIEQIQFIKLFGMAKIDNLLQEMLLGGSPSDAPHAHH<br>PLHPHLMQEHMGTNVIVANTMPTHLSNGQMSTP<br>ETPQPSPPGGSGSEPYKLLPGAVATIVKPLSAIPQPT<br>ITKQEVI (SEQ ID NO: 20) | Gene ID: 3072 |

SIX2 and CITED1 are expression markers for a population of self-renewing nephron progenitor cells in the developing human kidney. PAX2, is a transcription factor that orchestrates the development of both the nephron and the collecting duct and is expressed by Wolffian duct progenitor cells. Wolffian duct progenitor cells can express PAX2, CXCR4, cKit, and any combination thereof. MAFB, NPHS1, and ITGA are expression markers expressed in the glomerulus. HNF4A, LRP2, and CUBN expression is a signature profile indicative of a proximal tubule population within the nephron. The loop of Henle is identified by SLC12A1 expression.

The human induced pluripotent stem cells, posterior intermediate mesoderm cells, or NPCs provided herein can be cultured in monolayer culture, 3-dimensional culture, or in suspension culture for a period of time prior to admixing the cells with a population of ureteric bud cells, ureteric bud progenitor cells, ureteric tips, and/or ureteric stalks provided herein.

(3) Methods of Making and Characterizing In Vitro Kidneys and Lumenized In Vitro Kidneys.

Provided herein are methods of connecting NPCs with the UB kidney tissues or UB cells provided herein. Exemplary protocols and timelines are provided in FIG. 1B and FIG. 1C. In some embodiments, the posterior intermediate mesoderm cells or NPCs provided herein are contacted with CHIR99021 for at least about 10 minutes, at least about 20 minutes, at least about 30 minutes, at least about 1 hour, at least about 2 hours, at least about 3 hours, at least about 4 hours, or at least about 5 hours prior to admixing the posterior intermediate mesoderm cells with a population of ureteric bud cells or ureteric bud progenitor cells provided herein. In some embodiments, the posterior intermediate mesoderm cells or NPCS provided herein are combined in suspension culture with UB fragments (e.g., tips and/or stalks), core masses. In some embodiments, the UB kidney tissues are fragmented into tips and/or stalks. In some embodiments, the UB kidney tissue fragments are recombined with a population of nephron cells, NPCs, or posterior intermediate mesoderm cells to form an in vitro kidney provided herein. The combined cell populations can be centrifuged, resuspended, and loaded into a syringe for deposition and bioprinting. Methods of cellular deposition and bioprinting cellular populations provided herein are discussed further below.

Methods of Bioprinting and Arranging Kidney Tissues.

Provided herein are methods of bioprinting a kidney or a kidney tissue provided herein. Bioprinting is a method of using cellular bioinks comprising either cells or a combination of cells with hydrogels deposited by a bioprinting system that spatially controls deposition of living cells in defined geometric patterns. Bioprinting can be used to establish the architecture of the nephron and kidney tissues provided herein.

In some embodiments, the bioprinting system comprises a two-dimensional (2D) or three-dimensional (3D) prototype device for providing non-limiting examples of suitable bioprinting techniques. Such a device may include at least one or more controller(s) and one or more mechanical dispense tool(s). The mechanical dispense tool(s) is operably coupled with the controller(s) so as to allow for bioprinting in accordance with one or more instructions.

In some embodiments, each of the controller(s) comprise at least one processor and at least one non-transitory computer-readable medium. Data and/or instructions can be stored on the at least one non-transitory computer-readable medium. In some embodiments, the instructions comprise receiving one or more instructions for printing one or more 3D objects. In some embodiments, the one or more instructions comprise a file or a set of files that can be loaded into the controller(s). The file or set of files may correspond to one or more object(s) in 2D or 3D to be manufactured by the bioprinting system. The file or set of files may correspond to a plurality of slices for each of the one or more object(s). In some embodiments, the instructions can be determined by one or more computer model, such as, for example, a machine learning model.

In some embodiments, bioprinting system is configured to print 2D or 3D structures according to computer-executable instructions from the computer device. In some embodiments, the instructions are predetermined based on one or more criteria. Such criteria may comprise, for example, one or more threshold(s) corresponding to signals obtained from sensor(s). In some embodiments, the one or more instructions are based on a user input.

The bioprinting system may further include a plurality of independently addressable printheads mounted on a 3-axis, motion-controlled gantry. In some embodiments, the mechanical dispense tool(s) comprise one or more syringe barrels in fluid communication with one or more outlet(s). In some embodiments, a diameter of the outlet comprises an inner diameter of about, 20, 50, 100, 150, 200, 250, 300, 350, 400, 450, 500, 550, 600, 650, 700, 750, 800, 850, 900, 950, or 1000 μm.

In some embodiments, the outlet(s) comprise syringe or dispense tip(s), capillary tube(s), or nozzle(s). Cellular bioinks, used interchangeably herein with cellular gels, can be stored in the syringe barrels, and can be extruded from the mechanical dispense tool(s) via the nozzle(s). The nozzle(s) can be of varying sizes, and may extrude the bioinks my applying air pressures corresponding to varying print speeds. In some embodiments, the applied air pressure ranges from 1-90 psi. In some embodiments, the print speeds range from 0.1-10 mm/sec. In some embodiments, the print speed comprises 0.6 mm/sec.

In some embodiments, the instructions comprise translating the one or more mechanical dispense tool(s) to print the structures. To generate structures, such 3D kidney tissues, the printing is performed in a sequence or plurality of layers and/or functional units. In some embodiments, the functional units comprise any suitable geometry, such as, for example, circles, squares, rectangles, triangles, polygons, and irregular geometries. In some embodiments, the printing is performed so as to generate a repeating pattern of bioprinted functional units to form kidney tissues.

In some embodiments, the bioprinting system is designed to maintain cell viability throughout the printing process. In some embodiments, the bioprinting system comprises a printing chamber for maintaining culture conditions. In some embodiments, such conditions include temperature, humidity, gas partial pressures, or other conditions. In some embodiments, the temperature is maintained between about 4 degrees Celsius (° C.) to about 45° C. In some embodiments, such conditions are monitored using sensors at different locations in the printing chamber.

In some embodiments, the syringe barrels are sized to hold between about 1 milliLiter (mL) and about 200 mL. In some embodiments, the nozzle is sized to provide a minimum resolution between about 0.5 microLiters (μL) to about 10 μL. In some embodiments, the mechanical dispense tool comprises one or more sensor(s) for detecting and/or calibrating a location of the nozzle.

In some embodiments, the printing is performed on a variety of surfaces. The surface may comprise a membrane, such as, for example, a polyester membrane. The surfaces may comprise one or more well plate(s). In some embodiments, the well plate is a 96, 384, 1536-well plate or the like. In some embodiments, the surface comprises a membrane within each well of a well plate. In some embodiments, the well plate(s) comprise Transwell permeable supports.

In some embodiments, bioprinting comprises dispensing the one or more bioink(s) via the mechanical dispense tool(s). In some embodiments, the one or more bioink(s) comprise cells. Non-limiting examples of bioinks with cells include cell solutions, cell suspensions, cell-comprising gels or pastes, cell concentrations, multicellular bodies (e.g., pre-formed cellular aggregates, spheroids, embryoid bodies, or the like), or combinations thereof. In some embodiments, the cells are of different types or combinations thereof. In some embodiments, the cells in the bioinks are based on the type of tissue to be printed. In some embodiments, the cells comprise pluripotent stem cells. In some embodiments, the cells comprise UB progenitor cells. In some embodiments, the one or more bioink(s) comprise UB tissues.

In some embodiments, hydrogels in the bioinks comprise extracellular matrix. In some embodiments, the extracellular matrix comprises a solubilized basement membrane preparation extracted from Engelbreth-Holm-Swarm (EHS) mouse sarcoma, laminin, collagen IV, heparan sulfate proteoglycans, entactin, fibronectin, vitronectin, retronectin, elastin, hyaluronic acid, methylcellulose, a gelatin, chitosan, alginate, fibrin, or any combination thereof. In some embodiments, the extracellular matrix comprises a solubilized basement membrane preparation extracted from any of the above.

In some embodiments, the bioink(s) comprise media. In some embodiments, media is added to the printed structure after the bioprinting. In some embodiments, the printed structures are maintained in culture conditions upon being printed. In some embodiments, the media is dispensed from the mechanical dispense tool(s). In some embodiments, the media comprises basal Differentiation Medium (DM). In some embodiments, the media comprises any of the cell culture agents or supplements described herein.

In some embodiments, the printed structures are maintained at an air-liquid interface with media. In some embodiments, the media is refreshed at the air-liquid interface as designated time periods, such as, for example, every day, every other day, every two days, etc.

In some embodiments, a composition or system provided herein comprises a population of NPCs. In some embodiments, the NPCs are in contact while at least partially immersed in a culture medium, thereby forming a tubular network that is capable of providing flow therein or facilitates fluid flow through the tubular network, the composition, or the system.

In some embodiments, the printing is performed at spatially defined locations. In some embodiments, the spatially defined locations are sufficiently spaced to contiguously fuse the kidney tissues from at least one connecting point. In some embodiments, the spatially defined locations are sufficiently spaced to form repeating units of kidney tissue connections, e.g., nephric-ureteric connections, ureteric/UB connections, etc.

In some embodiments, bioprinting with the bioprinting system can be combined with microfluidics to construct or culture the kidney tissues.

Structural Characterization of In Vitro Kidneys and Tissues.

Provided herein are compositions comprising in vitro-engineered kidneys and kidney tissues and methods of making the same. In some embodiments, the compositions provided herein comprise a UB kidney tissue, a nephron kidney tissues, or combinations thereof. In some embodiments, the compositions provided herein comprise a lumenized kidney or lumenized kidney tissue. In some embodiments, the lumenized kidney or lumenized kidney tissue comprises a plurality of ureteric bud (UB) kidney tissues that have been fused while arranged in a sequential configuration. In some embodiments, the lumenized kidney or lumenized kidney tissue comprises a plurality of ureteric bud (UB) kidney tissues that have been fused while arranged in a tubular structure.

Provided herein are in vitro compositions comprising: an in vitro-differentiated kidney tissue comprising a population of nephron progenitor cells (NPCs) connected to a population of fragmented ureteric bud (UB) kidney tissues, wherein the in vitro-differentiated kidney tissue comprises repeating units of nephric-ureteric connections. In some embodiments, each unit is at least about 1 millimeter to about 10 millimeters in size. In some embodiments, the repeating units of nephric-ureteric connections comprise a nephron marker and a ureteric bud (UB) marker. In some embodiments, the repeating units of nephric-ureteric connections comprise two or more markers selected from: CK8, MAFB, LRP2, and GATA3. In some embodiments, the repeating units of nephric-ureteric connections comprise a nephron marker, wherein the nephron marker comprises MAFB or LRP2. In some embodiments, the repeating units of nephric-ureteric connections comprise or express a UB marker, wherein the UB marker is selected from the group consisting of RET1, SOX9, CK8, and GATA3.

Provided herein are in vitro kidneys and kidney tissues comprising or expressing a marker selected from the group consisting of: aquaporin 1 (AQP1), aquaporin 2 (AQP2), calbindin 1 (CALB1), cluster of differentiation 13 (CD13), cadherin 1 (CDH1), CK8, cKit, cubulin (CUBN), cystatin C, CXCR4, death associated protein like 1 (DAPL1), E-cadherin (ECAD), empty spiracles homeobox 2 (EMX2), engrailed homeobox 2 (EN2), GATA3, hepatocyte nuclear factor 4 alpha (HNF4A), hepatocyte nuclear factor 1 beta (HNF1B), leucine rich repeat containing G protein-coupled receptor 5 (LGR5), leucine rich repeat containing G protein-coupled receptor 6 (LGR6), LIM homeobox 1 (LHX1), Lotus Tetragonolobus Lectin (LTL), LDL receptor related protein 2 (LRP2), LY6/PLAUR domain containing 1 (LYPD1), MAFB, PAX2, paired box 8 (PAX8), platelet and endothelial cell adhesion molecule 1 (PECAM1), podocalyxin like (PODXL), RET1, serum creatinine (SCr), Six homeobox 1 (SIX1), SIX2, Special AT-rich sequence-binding protein (SATB2), SOX9, SRY-box transcription factor 17 (SOX17), parathyroid hormone 1 receptor (PTH1R), claudin 2 (CLDN2), tight junction protein 3 (TJP3), transcription factor 21 (TCF21), Wnt family member 4 (WNT4), WNT9, and WNT11. Provided herein are in vitro kidneys and kidney tissues comprising or expressing two or more markers selected from the group consisting of: aquaporin 1 (AQP1), aquaporin 2 (AQP2), calbindin 1 (CALB1), cluster of differentiation 13 (CD13), cadherin 1 (CDH1), CK8, cKit, cubulin (CUBN), cystatin C, CXCR4, death associated protein like 1 (DAPL1), E-cadherin (ECAD), empty spiracles homeobox 2 (EMX2), engrailed homeobox 2 (EN2), GATA3, hepatocyte nuclear factor 4 alpha (HNF4A), hepatocyte nuclear factor 1 beta (HNF1B), leucine rich repeat containing G protein-coupled receptor 5 (LGR5), leucine rich repeat containing G protein-coupled receptor 6 (LGR6), LIM homeobox 1 (LHX1), Lotus Tetragonolobus Lectin (LTL), LDL receptor related protein 2 (LRP2), LY6/PLAUR domain containing 1 (LYPD1), MAFB, PAX2, paired box 8 (PAX8), platelet and endothelial cell adhesion molecule 1 (PECAM1), podocalyxin like (PODXL), RET1, serum creatinine (SCr), Six homeobox 1 (SIX1), SIX2, Special AT-rich sequence-binding protein (SATB2), SOX9, SRY-box transcription factor 17 (SOX17), parathyroid hormone 1 receptor (PTH1R), claudin 2 (CLDN2), tight junction protein 3 (TJP3), transcription factor 21 (TCF21), Wnt family member 4 (WNT4), WNT9, and WNT11.

Provided herein are in vitro compositions comprising: an in vitro-differentiated kidney tissue comprising a population of nephron progenitor cells (NPCs) connected to a population of fragmented ureteric bud (UB) kidney tissues, wherein: the in vitro-differentiated kidney tissue comprises a collecting duct, and the in vitro-differentiated kidney tissue comprises a glomerular marker, a proximal tubule marker, a tubular epithelium marker, and a connecting segment marker.

In some embodiments, the in vitro kidneys and kidney tissues provided herein comprise a glomerulus or a glomerular tissue. In some embodiments, the in vitro kidneys and kidney tissues provided herein comprise a glomerular marker comprising MAFB, WT1, nephrin, or podocin.

In some embodiments, the in vitro kidneys and kidney tissues provided herein comprise a proximal tubule or a proximal tubule tissue. In some embodiments, the in vitro kidneys and kidney tissues provided herein comprises a proximal tubule marker comprising LRP2, LTL, CUBN, PTH1R, AQP1, CLDN2, TJP3, or CD13.

In some embodiments, the in vitro kidneys and kidney tissues provided herein comprise a tubular epithelium. In some embodiments, the in vitro kidneys and kidney tissues provided herein comprise a tubular epithelium marker comprising CK8, aquaporins, CD34, or WGA lectin.

In some embodiments, the in vitro kidneys and kidney tissues provided herein comprise a connecting segment. In some embodiments, the in vitro kidneys and kidney tissues provided herein comprise a connecting segment marker comprising GATA3 or AQP2.

In some embodiments, the in vitro kidneys and kidney tissues provided herein comprise a collecting duct. In some embodiments, the vitro kidneys and kidney tissues express aquaporins. The aquaporins are a family of membrane water channels expressed by collecting duct cells. In some embodiments, the in vitro kidneys and kidney tissues express aquaporin 1 (AQP1), aquaporin 2 (AQP2), aquaporin 3 (AQP3), aquaporin 4 (AQP4), or any combination thereof. In some embodiments, the in vitro kidneys and kidney tissues provided herein comprise a collecting duct marker comprising: GATA3, EPCAM, or ECAD.

Provided herein are in vitro compositions comprising: an in vitro-differentiated kidney tissue comprising a population of nephron progenitor cells (NPCs) connected to a population of fragmented ureteric bud (UB) kidneys, wherein: the in vitro-differentiated kidney that comprises a collecting duct, and the in vitro-differentiated kidney tissue comprises two or more markers selected from: LRP2, GATA3, MAFB, and CK8. In some embodiments, the in vitro-differentiated kidney tissue comprises two or more markers, wherein the two or more markers comprise: (i) MAFB and LRP2; (ii) MAFB and CK8; (iii) MAFB and GATA3; (iv) LRP2 and CK8; (v) LRP2 and GATA3; or (vi) CK8 and GATA3. In some embodiments, the in vitro-differentiated kidney tissue comprises three or more markers, wherein the three or more markers comprise: (i) MAFB, LRP2, and CK8; (ii) MAFB, LRP2, and GATA3; (iii) MAFB, CK8, and GATA3; or (iv) LRP2, CK8, and GATA3. In some embodiments, the in vitro-differentiated kidney tissue comprises four or more markers, wherein the four or more markers comprise: MAFB, LRP2, CK8, and GATA3.

Provided herein are in vitro kidneys and kidney tissues that comprise a ureteric bud marker, a nephron marker, a UB-NPC connecting point, and comprise at least one functional parameter of a kidney. Functional parameters of the kidneys and kidney tissues provided herein are discussed in further detail below.

Functional Characterization of In Vitro Kidneys and Kidney Tissues.

The in vitro kidneys and kidney tissues provided herein have functional parameters that can be characterized similar to a human kidney in vivo and are not observed in monolayer cultures of separate kidney cell populations. Functional parameters of the in vitro kidneys and kidney tissues provided herein include filtration of blood or solutions, formation of lumen, flow of fluid within the lumen, kidney metabolic functions, kidney morphological function, and ion exchange. Methods of measuring functional parameters can be performed using in vitro assays or performing urinalysis or blood analysis assays in vivo.

In some embodiments, the in vitro kidneys and kidney tissues provided herein are capable of having flow. Methods of measuring flow within a tissue include but are not limited to: diffuse correlation spectroscopy, ultrasound, Doppler techniques, venous occlusion plethysmography, permeability assays, flowthrough immunoassays, microscopy, and imaging techniques. Flow rates, for example can be measured in animal models that have received a kidney transplant using an optical Doppler velocimeter.

In some embodiments, the in vitro kidneys and kidney tissues provided herein have cilia formation and movement in the core or the exterior portion of the lumen where fluid flows. Cilia movement and formation can be tracked using methods such as microscopy.

In some embodiments, the in vitro kidneys and kidney tissues provided herein are capable of filtering urea. In some embodiments, the in vitro kidneys and kidney tissues provided herein are capable of filtering and/or secreting creatinine. In some embodiments, the in vitro kidneys and kidney tissues provided herein are capable of filtering and excreting uric acid. In some embodiments, the in vitro kidneys and kidney tissues provided herein are capable of transporting and excreting ammonia and/or ammonium phosphate. Ammonia is produced from glutamine (Gln) as a result of proximal tubule ammoniagenesis. Glutamine is transported across both the apical and basolateral plasma membranes and then transported into mitochondria. The enzyme glutaminase (GA) is the first step in ammoniagenesis, and glutamate dehydrogenase (GDH) results in the production of the second $NH4+$ molecule. Metabolism of $\alpha$-ketoglutarate ($\alpha$KG) leads to the production of the first of two $HCO3-$ ions. Further metabolism in the cytoplasm results in the production of a second $HCO3-$. Thus, complete metabolism of each glutamine produces two $NH4+$ and two $HCO3-$ ions. Methods of measuring the level or activity of urea, creatinine, uric acid, ammonium, and other metabolites include but are not limited to: enzymatic assays, immunosorbent assays, absorbance assays, in vivo animal model blood assays and urinalysis.

In some embodiments, the in vitro kidneys and kidney tissues provided herein produce renin. In some embodiments, the in vitro kidneys and kidney tissues provided herein produce erythropoietin. Renin and erythropoietin production can be measured by immunoassays (e.g., enzyme-linked immunosorbent assay, ELISA).

In some embodiments, the in vitro kidneys and kidney tissues provided herein are capable of ion exchange and ion transport. In some embodiments, the in vitro kidneys and kidney tissues provided herein express increased levels of kidney ion channels and ion transporters relative to a population of kidney cells that are not made by the methods provided herein. Non-limiting examples of kidney ion channels and kidney transporters that can be expressed by the in vitro kidneys and kidney tissues provided herein include: TRPC6 (Trpc6), TRPM6 (Trpm6), ClC-5 (CLCN5), ClC-Kb (CLCNKB), ROMK (KCNJ1), Kir4.1 (KCNJ10), ENaC (Scnn1a), ENaC (Scnn1a), Polycystin 2 (PKD2), and the Sodium/phosphate (Na/Pi) cotransporter. Ion channel and ion transport function can be measured by electrophysiological techniques (e.g., voltage clamp), microelectrode arrays, ion exchange chromatography, and ion transport assays.

In some embodiments, the in vitro kidneys and kidney tissues provided herein are capable of metabolic functions. In some embodiments, the in vitro kidneys and kidney tissues provided herein have albumin reabsorption function. Reabsorption of albumin occurs by cellular-mediated endocytosis in the glomerulus and the proximal tubule of the kidney. Albumin reabsorption by the in vitro kidneys and kidney tissues can be measured by immunoassays or labeling albumin with fluorescent tags or radioisotopes to track albumin movement through the kidney.

(4) Transplant Compositions.

Provided herein are transplant compositions comprising the in vitro kidney tissues provided herein. In some embodiments, the kidney tissues and compositions comprising the kidney tissues provided herein further comprise a cell culture medium or diluents that maintain tissue survival and promote kidney tissue function. In some embodiments, the compositions provided herein further comprise growth factors or agents. In some embodiments, the growth factors or agents comprise CHIR99021, Activin A, GDNF1, FGF1, FGF7, FGF9, BMP4, BMP7, Retinoic Acid, RSPO1, or any combination thereof.

In some embodiments, the compositions provided herein comprise one or more metabolites. In some embodiments, the compositions provided herein comprise urea, creatinine, uric acid, ammonium phosphate, or a combination thereof. In some embodiments, the compositions provided herein comprise an extracellular matrix. In some embodiments, the compositions provided herein comprise a cryopreservation agent, a serum, or a suspension.

In some embodiments, the compositions provided herein comprise a diluent or a saline solution. In some embodiments, the saline solution is normal saline solution (NSS), or Hank's Balanced Salt solution (HBSS). In some embodiments, the compositions are formulated for administration of the compositions, kidneys, or kidney tissues to a subject.

Provided herein are transplant compositions comprising UB kidney tissues, nephron kidney tissues, or a combination thereof.

A transplant composition provided herein can further comprise agents that suppress an immune response in a subject. Transplantation can provoke the transplant recipient's immune system to attack the transplant and reject the tissue. This side effect of transplantation can be lethal without pharmaceutical or genetic interventions. For example, immunosuppressants are drugs that are administered to a transplant recipient to reduce the risk of transplant rejection after a transplant by managing the immune system's response to the new transplant composition or graft. In some embodiments, the transplant composition provided herein further comprises one or more immunosuppressants.

In some embodiments, the one or more immunosuppressants comprise a steroid, an anti-interleukin-2 antibody, a calcineurin inhibitor, an antibiotic, an anti-viral, an anti-fungal, an inosine monophosphate dehydrogenase inhibitor, a disease-modifying anti-rheumatic drug, an mTor inhibitor, or any combination thereof. Non-limiting examples of immunosuppressants that can be used in combination with a composition or system provided herein include, for example, prednisone, prednisolone, penicillin, tetracycline, amoxicillin, azithromycin, tacrolimus, cyclosporine, fluconazole, nystatin, ketoconazole, clotrimazole, mycophenolate mofetil, apremilast, cyclophosphamide, hydroxychloroquine, leflunomide, methotrexate, mycophenolate, sulfasalazine, abatacept, belimumab, ixekizumab, rituximab, sailumab, secukinumab, tocilizumab, ustekinumab, azathioprine, rapamycin, ridaforolimus, deforolimus, everolimus, sirolimus, umirolimus, and zotarolimus. In some embodiments, the transplant composition comprises kidney tissues that have been genetically modified to prevent transplant rejection. In some embodiments, the transplant composition comprises kidney tissues that are hypoimmunogenic and evade immune rejection. Methods of generating genetically modified hypoimmunogenic cells and tissues can include CRISPR/Cas-mediated modifications or gene editing systems that reduce or remove major histocompatibility complex (MHC) class I or class II molecules from being expressed by the transplant composition. In some embodiments, the transplant composition further comprises a population of cells that induce transplant tolerance. For example, the transplant composition provided herein can further comprise alloantigen-specific T-regulatory cells.

(5) Systems for Culturing Kidney and Kidney Tissues.

Provided herein are systems comprising a kidney or kidney tissue provided herein that permit filtering of a subject's blood or permit the maintenance and survival of the kidney tissues provided herein. Such systems can be helpful for culturing biological materials such as cells, cellular aggregates, tissues, and organoids provided herein, facilitating the growth and/or differentiation of such biological materials for downstream evaluation or treatment of subjects.

In some embodiments, the systems provided herein comprise producing a blood circuit, wherein the blood circuit comprises blood from the subject in fluid communication with a kidney or kidney tissue provided herein. In some embodiments, the blood circuit comprises a bioreactor. A bioreactor can be utilized as part of a system or an ex-vivo blood circuit provided herein to supply a kidney or kidney tissue with physical stimulation, electrical stimulation, chemical stimulation, gas exchange, or a combination of these. In some embodiments, a bioreactor can comprise means for increasing the level of oxygen in a culture media. In some embodiments, disclosed herein can be a system comprising any of the compositions provided herein.

In some embodiments, a system can comprise at least one of a bioreactor, pump, housing, tubing, oxygen permeable tubing, incubator, motor, computer or controller, storage medium, biological safety cabinet, incubator, or any combination thereof. In some embodiments, cells are stored in an incubator. In some embodiments, an incubator can regulate temperature, gaseous concentration, humidity, and any combination thereof. Fluid pressure, flow characteristics and geometry of the bioreactor can be varied to apply a desired fluid shear stress to the in vitro kidney and kidney tissues provided herein.

In some embodiments, a pump can comprise a peristaltic pump or a vacuum pump. In some cases, a system can further comprise a cannula, a perfusion apparatus, a holding container, a tubing, a pump, a sensor, a thermometer, an electrode, a valve, a balloon, a pacemaker, a thermostat, a user interface, or any combination thereof. In some embodiments, a sensor can comprise a glucose sensor, an ammonia sensor, an oxygen sensor, a fluid sensor, a temperature sensor, a pressure sensor, or any combination thereof.

In some embodiments, a biological safety cabinet can provide laminar airflow to prevent contamination of the biological materials. In some embodiments, sterile techniques are performed to prevent contamination. In some embodiments, sterile techniques can include sterilizing surfaces and equipment with about 70% isopropyl alcohol, use of UV radiation, use of personal protective equipment such as gloves, lab coats, or body suits, or any combination thereof.

In some embodiments, a bioreactor can be utilized as part of a system provided herein. A bioreactor may need to supply the biological materials or portions thereof with physical stimulation, electrical stimulation, chemical stimulation, or a combination thereof, depending on what is needed for growth, maintenance, or differentiation of the biological materials. In some embodiments, the kidney tissues provided herein can be cultured with growth factors described herein. For example, convert growth factor bl and trans-retinoic acid may allow for renal proximal tubule cells grow as a monolayer and produce lumens with polarized epithelial layers, microvilli, and tight junction complexes.

In some embodiments, the bioreactor is adapted for use with the bioprinting systems described herein. In some embodiments, the bioreactor can be upstream and/or downstream from the bioprinting systems.

In some embodiments, a bioreactor performs real time monitoring of certain parameters, such as pH, $pO_2$, $pCO_2$, temperature, electrolyte levels, glucose or lactate concentrations, and perfusion parameters, such as perfusion pressure and flow rates. The bioreactor may maintain conditions stable and adjustable, particularly during long-term culture. This monitoring further allows for calculation of other important parameters, such as vascular resistance. In some embodiments, various assays can be used to investigate cellular viability and proliferation during NPC or UB tissue growth. Monitoring can be performed at any time, for example a measurement can be taken before perfusion, during perfusion, and after perfusion. In some cases, a measurement can be taken from about 1 hour, 1 day, 2 days, 3 days, 4 days, 5 days, 6 days, 7 days, 8 days, 9 days, 10 days, 11 days, 12 days, 13 days, 14 days, 15 days, 17 days, 20 days, 22 days, 24 days, 28 days, 30 days, 2 months, 5 months, 7 months, 8 months, 10 months, or up to 1 year after perfusion of a population of cells into the kidney tissues or portions thereof. In some embodiments, the temperature is maintained between about 4° C. to 45° C.

In some embodiments, the bioreactor can be configured to allow for fluid perfusion at varying or constant flow rates. In some embodiments, fluid perfusion is applied in closed-loop or open-loop flow systems. In some embodiments, the flow rate comprises a range of about 0.01 mm per min to 50 mm per min. In some embodiments, the flow rate comprises a range of about 0.01 mL/min to 0.1 mL/min. In some embodiments, the flow rate comprises a range of about 0.1 mL/min to 1.0 mL/min. In some embodiments, the flow rate comprises a range of about 1.0 mL/min to 2.0 mL/min. In some embodiments, the flow rate comprises a range of about 2.0 mL/min to 3.0 mL/min. In some embodiments, the flow rate comprises a range of about 3.0 mL/min to 4.0 mL/min. In some embodiments, the flow rate comprises a range of about 4.0 mL/min to 5.0 mL/min. In some embodiments, the flow rate comprises a range of about 5.0 mL/min to 10.0 mL/min. In some embodiments, the flow rate comprises a range of about 10 mL/min to 15 mL/min. In some embodiments, the flow rate comprises a range of about 15 mL/min to 20 mL/min. In some embodiments, the flow rate comprises a range of about 20 mL/min to 25 mL/min. In some embodiments, the flow rate comprises a range of about 30 mL/min to 35 mL/min. In some embodiments, the flow rate comprises a range of about 35 mL/min to 40 mL/min. In some embodiments, the flow rate comprises a range of about 40 mL/min to 45 mL/min. In some embodiments, the flow rate comprises a range of about 45 mL/min to 50 mL/min.

In some embodiments, a bioreactor can comprise means for increasing the level of oxygen in a culture media. In some embodiments, elevated oxygen levels can range from about 22% to about 25%, from about 25% to about 30%, from about 30% to about 35%, from about 35% to about 40%, from about 40% to about 45%, from about 45% to about 50%, from about 50% to about 55%, from about 55% to about 60%, from about 60% to about 65%, from about 65% to about 70%, from about 70% to about 75%, from about 75% to about 80%, from about 80% to about 85%, from about 85% to about 90%, from about 90% to about 95%, from about 95% to about 100%. In some embodiments a level of increased oxygen can vary over culture time.

In some embodiments, elevated oxygen levels can be produced by direct oxygenation, in-line oxygenation, gas permeable materials, or any combination thereof. In some embodiments, direct oxygenation can comprise using a membrane oxygenating chamber. In some embodiments, direct oxygenating can comprise using a bubbler. In some embodiments, in-line oxygenation can comprise use of in-line oxygenators. In some embodiments, a media can be pumped by a peristaltic pump. In some embodiments a media can be passed through gas permeable material allowing gaseous exchange through the material. In some embodiments, gaseous exchange may comprise oxygen exchange, nitrogen exchange, carbon dioxide exchange, or any combination thereof. In some embodiments, an at least partly permeable tubing may comprise silicone tubing. In some embodiments, silicone tubing may allow oxygen exchange, creating heightened oxygen levels in a media. In some embodiments oxygen levels in the media can be heightened by a direct injection of a mixture of oxygen and one or more other gases. In some embodiments one or more other gases can comprise nitrogen, carbon dioxide, or a combination of the two. In some embodiments oxygen levels in the media can be heightened by an injection of a gas comprising about 40% oxygen, about 45% oxygen, about 50% oxygen, about 55% oxygen, about 60% oxygen, about 65% oxygen, about 70% oxygen, about 75% oxygen, about 80% oxygen, about 85% oxygen, about 90% oxygen, about 95% oxygen, or about 100% oxygen. In some embodiments oxygen levels in the media can be heightened by an injection of about 100% pure oxygen. In some embodiments heightened oxygen levels in the media can be facilitated by oxygen carrying molecules to increase access to cells within the biological materials. In some embodiments, the biological materials comprise isolated cells, cellular aggregates, tissues, organoids or organs, or portion thereof. In some embodiments, cells may comprise seeded NPCs, UB progenitor cells, pluripotent stem cells, posterior intermediate mesoderm cells, or other cells provided herein. In some embodiments, an isolated organ, organoid, or portion thereof may comprise an extracellular matrix (ECM). In some embodiments, a media can be hyperoxygenated prior to seeding cells into an isolated organ, organoid, or portion thereof. In some embodiments, a media can be hyperoxygenated prior to seeding cells into an ECM graft. In some embodiments, oxygen levels can be adjusted based on metrics. In some embodiments, metrics can be evaluated or adjusted and can comprise media glucose levels, lactate levels, pCO2, pH, ammonia levels, pyruvate levels, other measurable parameters, and any combination thereof.

In some embodiments, a bioreactor comprises a vertical wheel bioreactor, a perfusion bioreactor, an air-lift bioreactor, a continuous stirred-tank bioreactor, a fluidized bed bioreactor, a packed bed bioreactor, or the like. In some embodiments, the cells, cellular aggregates, tissues, and organoids provided herein are maintained in the bioreactor at different stages during development. In some embodiments, the biological materials described herein are cultured in the bioreactor prior to differentiation. In some embodiments, the biological materials described herein are cultured in the bioreactor during differentiation. In some embodiments, the biological materials described herein are cultured in the bioreactor after differentiation. In some embodiments, the biological materials are cultured in the bioreactor such that specific cellular markers are expressed, such as, for example, NPC markers or UB markers described herein. In some embodiments, the biological materials are cultured in the bioreactor such that specific structures are formed, such as, for example, contiguous fusion of kidney tissues from at least one connecting point or repeating units of kidney tissue connections, e.g., nephric-ureteric connections, ureteric/UB connections, etc.

In some embodiments, the bioreactors can be used in a batch mode, fed batch mode, circulation, and perfusion mode, and can be fully controlled in a closed, aseptic environment and can be implemented for a single use (to be disposed after one culturing cycle) as well as for multiple cycle uses.

In some embodiments, the computer or controller of the systems comprise at least one processor and at least one non-transitory computer-readable medium. Data and/or instructions can be stored on the at least one non-transitory computer-readable medium. In some embodiments, the instructions comprise receiving one or more instructions for operating the systems herein. In some embodiments, the one or more instructions comprise a file or a set of files that can be loaded into the controller(s). The file or set of files may correspond to one or more protocols to be managed by the systems herein. The file or set of files may correspond to a plurality of conditions for each of the biological materials culture within the systems. In some embodiments, the instructions can be determined by one or more computer model, such as, for example, a machine learning model.

(6) Kits and Reagents.

The compositions provided herein can be made using a reagent or series of reagents that promote the formation of a collecting duct or connections between UB and nephron kidney tissues. A reagent provided herein can comprise: a basal medium supplemented with one or more growth factors, metabolites, antioxidants, antigens, small molecules, and/or proteins that permit differentiation of a stem cell to a ureteric bud (UB) progenitor cell or a UB cell.

A reagent provided herein can comprise: a basal medium supplemented with one or more growth factors, metabolites, antioxidants, antigens, small molecules, and/or proteins that permit differentiation of a stem cell to nephron progenitor cell (NPC). In some embodiments, the reagent further comprises serum.

Provided herein are reagents comprising one or more agent selected from the group consisting of: fetal bovine serum (FBS), Human leukocyte antigen B27 (B27), L-Glutamine, insulin-transferrin-selenium (ITS), one or more non-essential amino acids (NEAA), 2-mercaptoethanol, Y27632, Activin A, BMP4, CHIR99021, retinoic acid, FGF9, LDN193189, SB431542, GDNF1, FGF1, FGF7, RSPO1, and a solubilized basement membrane preparation extracted from Engelbreth-Holm-Swarm (EHS) mouse sarcoma (MATRIGEL®). In some embodiments, the reagents provided herein comprise at least about 0.1%, at least about 0.25%, at least about 0.5%, at least about 0.75%, at least about 1%, at least about 1.25%, at least about 1.5%, at least about 1.75%, at least about 2%, at least about 3%, at least about 4%, up to 5% B27 percent volume of the total volume of the reagent. In some embodiments, the reagents provided herein comprise at least about 0.1%, at least about 0.25%, at least about 0.5%, at least about 0.75%, at least about 1%, at least about 1.25%, at least about 1.5%, at least about 1.75%, at least about 2%, at least about 3%, at least about 4%, up to 5% L-glutamine percent volume of the total volume of the reagent. In some embodiments, the reagents provided herein comprise at least about 0.1%, at least about 0.25%, at least about 0.5%, at least about 0.75%, at least about 1%, at least about 1.25%, at least about 1.5%, at least about 1.75%, at least about 2%, at least about 3%, at least about 4%, up to 5% ITS percent volume of the total volume of the reagent. In some embodiments, the reagents provided herein comprise at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 55%, at least about 65%, at least about 70%, up to 75% solubilized basement membrane preparation extracted from Engelbreth-Holm-Swarm (EHS) mouse sarcoma (MATRIGEL®) percent volume of the total volume of the reagent (v/v). In some embodiments, the reagents provided herein comprise at least about 0.1%, at least about 0.25%, at least about 0.5%, at least about 0.75%, at least about 1%, at least about 1.25%, at least about 1.5%, at least about 1.75%, at least about 2%, at least about 3%, at least about 4%, up to 5% ITS percent volume of the total volume of the reagent. In some embodiments, the reagents provided herein comprise at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, up to 50% fetal bovine serum percent volume of the total volume of the reagent. In some embodiments, a reagent provided herein comprises at least about a 50 micromolar (μM), at least about a 60 micromolar (μM), at least about a 10 micromolar (μM), at least about a 20 μM, at least about a 30 μM, at least about a 40 μM, at least about a 50 μM, at least about a 60 μM, at least about a 70 μM, at least about a 80 μM, at least about a 90 μM, at least about a 100 μM up to a 500 μM concentration of 2-mercaptoethanol. In some embodiments, a reagent provided herein comprises at least about a 10 micromolar (μM), at least about a 20 μM, at least about a 30 μM, at least about a 40 μM, at least about a 50 μM, at least about a 60 μM, at least about a 70 μM, at least about a 80 μM, at least about a 90 μM, at least about a 100 μM up to a 200 μM concentration of SB431542. In some embodiments, a reagent provided herein comprises at least about a 0.1 micromolar (μM), at least about a 1 μM, at least about a 2 μM, at least about a 3 μM, at least about a 4 μM, at least about a 5 μM, at least about a 6 μM, at least about a 7 μM, at least about a 8 μM, at least about a 9 μM, at least about a 10 μM, at least about a 50 μM, up to a 100 μM concentration of CHIR99021. In some embodiments, the reagent provided herein comprises about 1 μM up to a 10 μM concentration of CHIR99021. In some embodiments, a reagent provided herein comprises at least about a 0.1 micromolar (μM), at least about a 1 μM, at least about a 2 μM, at least about a 3 μM, at least about a 4 μM, at least about a 5 μM, at least about a 6 μM, at least about a 7 μM, at least about a 8 μM, at least about a 9 μM, at least about a 10 μM, at least about a 50 μM, up to a 100 μM concentration of Y27632. In some embodiments, a reagent provided herein comprises at least about a 0.1 nanogram/milliliter (ng/mL), at least about a 1 ng/mL, at least about a 2 ng/mL, at least about a 3 ng/mL, at least about a 4 ng/mL, at least about a 5 ng/mL, at least about a 6 ng/mL, at least about a 7 ng/mL, at least about a 8 ng/mL, at least about a 9 ng/mL, at least about a 10 ng/mL, at least about a 50 ng/mL, up to a 100 ng/mL concentration of Activin A. In some embodiments, a reagent provided herein comprises at least about a 0.01 nanogram/milliliter (ng/mL), at least about a 0.1 ng/mL, at least about a 0.5 ng/mL, at least about a 1 ng/mL, at least about a 1.5 ng/mL, at least about a 2 ng/mL, at least about a 2.5 ng/mL, at least about a 3 ng/mL, at least about a 3.5 ng/mL, at least about a 4 ng/mL, at least about a 4.5 ng/mL, at least about a 5 ng/mL, up to a 10 ng/mL concentration of bone morphogenetic protein 4 (BMP4). In some embodiments, a reagent provided herein comprises at least about a 0.01 nanogram/milliliter (ng/mL), at least about a 0.1 ng/mL, at least about a 0.5 ng/mL, at least about a 1 ng/mL, at least about a 1.5 ng/mL, at least about a 2 ng/mL, at least about a 2.5 ng/mL, at least about a 3 ng/mL, at least about a 3.5 ng/mL, at least about a 4 ng/mL, at least about a 4.5 ng/mL, at least about a 5 ng/mL, up to a 10 ng/mL concentration of glial cell line-derived neurotrophic factor (GDNF). In some embodiments, a reagent provided herein comprises at least about a 1 nanogram/milliliter (ng/mL), at least about a 10 ng/mL, at least about a 20 ng/mL, at least about a 30 ng/mL, at least about a 40 ng/mL, at least about a 50 ng/mL, at least about a 60 ng/mL, at least about a 70 ng/mL, at least about a 80 ng/mL, at least about a 90 ng/mL, at least about a 100 ng/mL, at least about a 500 ng/mL, up to a 1000 ng/mL concentration of fibroblast growth factor 9 (FGF9). In some embodiments, a reagent provided herein comprises at least about a 1 nanogram/milliliter (ng/mL), at least about a 10 ng/mL, at least about a 20 ng/mL, at least about a 30 ng/mL, at least about a 40 ng/mL, at least about a 50 ng/mL, at least about a 60 ng/mL, at least about a 70 ng/mL, at least about a 80 ng/mL, at least about a 90 ng/mL, at least about a 100 ng/mL, at least about a 500 ng/mL, up to a 1000 ng/mL concentration of FGF1. In some embodiments, a reagent provided herein comprises at least about a 1 nanogram/milliliter (ng/mL), at least about a 10 ng/mL, at least about a 20 ng/mL, at least about a 30 ng/mL, at least about a 40 ng/mL, at least about a 50 ng/mL, at least about a 60 ng/mL, at least about a 70 ng/mL, at least about a 80 ng/mL, at least about a 90 ng/mL, at least about a 100 ng/mL, at least about a 500 ng/mL, up to a 1000 ng/mL concentration of FGF7. In some embodiments, a reagent provided herein comprises at least about a 0.1 nanogram/milliliter (ng/mL), at least about a 1 ng/mL, at least about a 10 ng/mL, at least about a 20 ng/mL, at least about a 30 ng/mL, at least about a 40 ng/mL, at least about a 50 ng/mL, at least about a 60 ng/mL, at least about a 70 ng/mL, at least about a 80 ng/mL, at least about a 90 ng/mL, at least about a 100 ng/mL, at least about a 500 ng/mL, up to a 1000 ng/mL concentration of R-spondin 1 (RSPO1). In some embodiments, a reagent provided herein comprises at least about 1 nanoMolar (nM), at least about 5 nM, at least about 10 nM, at least about 15 nM, at least about 20 nM, at least about 25 nM, at least about 30 nM, at least about 35 nM, at least about 40 nM, at least about 45 nM, at least about 50 nM, at least about 75 nM, at least about 100 nM, up to a 500 nM concentration of LDN193189. In some embodiments, a reagent provided herein comprises at least about 1 nanoMolar (nM), at least about 5 nM, at least about 10 nM, at least about 15 nM, at least about 20 nM, at least about 25 nM, at least about 30 nM, at least about 35 nM, at least about 40 nM, at least about 45 nM, at least about 50 nM, at least about 75 nM, at least about 100 nM, at least about 500 nM, up to a 1000 nM concentration of retinoic acid.

Provided herein are reagents comprising: fetal bovine serum (FBS), R-spondin 1 (RSPO1) protein, (GNDF), fibroblast growth factor 1 (FGF1), fibroblast growth factor 7 (FGF7), LDN193189, and solubilized basement membrane preparation extracted from Engelbreth-Holm-Swarm (EHS) mouse sarcoma. In some embodiments, the FBS is present in an amount that is at least about 1% up to 20% volume by total volume of the reagent (v/v). In some embodiments, the retinoic acid is present in an amount that is at least about 10 nanoMolar (nM) concentration up to 200 nM concentration. In some embodiments, the RSPO1 is present in an amount that is at least about 10 nanograms per milliliter (ng/mL) up to 200 ng/mL. In some embodiments, the GDNF (e.g., GDNF1) is present in an amount that is at least about 0.1 nanograms per milliliter (ng/mL) up to 5 ng/mL. In some embodiments, the FGF1 is present in an amount that is at least about 10 nanograms per milliliter (ng/mL) up to 200 ng/mL. In some embodiments, the FGF7 is present in an amount that is at least about 3 nanograms per milliliter (ng/mL) up to 60 ng/mL. In some embodiments, the LDN193189 is present in an amount that is at least about 1 nanoMolar (nM) concentration up to 20 nM concentration. In some embodiments, the solubilized basement membrane preparation extracted from Engelbreth-Holm-Swarm (EHS) mouse sarcoma is present in an amount of at least 5% up to 80% volume by total volume of the reagent (v/v). In some embodiments, the reagents comprise: 10% FBS, 100 nM retinoic acid, 100 ng/mL RSPO1, 2 ng/mL GDNF, 100 ng/mL FGF1, 30 ng/mL FGF7, 10 nM LDN193189, and 50% solubilized basement membrane preparation extracted from Engelbreth-Holm-Swarm (EHS) mouse sarcoma (MATRIGEL®) (volume/total volume or v/v). In some embodiments, the reagents promote ureteric bud formation and branching (e.g., a branching medium provided herein).

Provided herein are kits for making the in vitro kidneys, kidney tissues, and compositions provided herein. In some embodiments, a formulation of a composition described herein is prepared in a single container for administration. In some embodiments, a formulation of a composition described herein is prepared in multiple containers for administration. A container provided herein can include a vessel, a vial, an ampule, a tube, a cup, a box, a bottle, a flask, a jar, a dish, a well of a single-well or a multi-well apparatus, a reservoir, a tank, or the like, or other device in which the compositions and reagents provided herein can be placed, stored and/or transported, and accessed to remove the contents. Examples of such containers include glass and/or plastic sealed or re-sealable tubes and ampules, including those having a rubber septum or other sealing means that is compatible with withdrawal of the contents using a needle and syringe. In some implementations, the containers are RNase free.

Provided herein are kids comprising: a first container comprising: a population of ureteric bud cells and a population of nephron progenitor cells; and a second container comprising media, growth factors, and agents for making an in vitro kidney tissue. Provided herein is a kit comprising: a first container comprising: (a) a population of ureteric bud kidney cells, (b) a population of nephron progenitor cells, or (c) an in vitro kidney tissue provided herein; and a second container comprising: a reagent provided herein. In some embodiments, the kits provided herein comprise a reagent provided herein. In some embodiments, the kits provided herein comprise ureteric bud (UB) cells. In some embodiments, the kits provided herein comprise nephron progenitor cells (NPCs). In some embodiments, the kits provided herein comprise human induced pluripotent stem cells (iPSCs). In some embodiments, the kits provided herein comprise endothelial cells. In some embodiments, the kits provided herein comprise an extracellular matrix.

Provided herein are kits and reagents for screening for nephrotoxicity or screening for a therapeutic drug candidate. Provided herein is a kit comprising: a first container comprising: (a) a population of ureteric bud kidney cells, (b) a population of nephron progenitor cells, or (c) an in vitro kidney tissue provided herein; and a second container comprising: reagents, a positive control for nephrotoxicity, and a test agent. The kits for screening for nephrotoxicity can be used to determine if a test agent is a viable candidate for clinical development or clinical trials in animals or humans. The test agent can be any therapeutic drug of interest for screening, for example, a lead candidate therapeutic agent. The test agent can be a small molecule, protein, cells, antibody, or chemical. In some embodiments, the kits provided herein comprise a reagent provided herein. In some embodiments, the kits provided herein comprise ureteric bud (UB) cells. In some embodiments, the kits provided herein comprise nephron progenitor cells (NPCs). In some embodiments, the kits provided herein comprise human induced pluripotent stem cells (iPSCs). In some embodiments, the kits provided herein comprise endothelial cells. In some embodiments, the kits provided herein comprise an in vitro-lumenized kidney tissue. In some embodiments, the kits provided herein comprise an in vitro-kidney tissue provided herein. In some embodiments, the kits provided herein comprise an extracellular matrix. In some embodiments, the kits provided herein comprise vessel, a vial, a multi-well plate, or a cell culture dish. In some embodiments, the kits provided herein comprise a therapeutic agent. In some embodiments, the therapeutic agent comprises a sodium-glucose cotransporter-2 (SGLT2) inhibitor, an angiotensin-converting enzyme (ACE) inhibitor, an angiotensin receptor blocker (ARB), a beta blocker, a diuretic, a potassium binder, a statin, an erythropoiesis-stimulating agent, an iron supplement, a phosphate binder, a calcium supplement, a vitamin D supplement, a calcimimetic, an aldosterone antagonist, a corticosteroid, metformin, a GLP-1 inhibitor, aspirin, a non-steroidal anti-inflammatory drug (NSAID), or any combination thereof. In some embodiments, the kits provided herein comprise an agent that causes kidney damage that can be used as a positive control in a screening assay. Non-limiting examples of agents that cause kidney damage include aminoglycosides, antifungals (amphotericin B), beta-lactams (e.g., cephalosporins, penicillins), quinolones (e.g., ciprofloxacin), rifampin (Rifadin), and vancomycin (Vancocin).

Provided herein is a method of screening a test agent for nephrotoxicity, the method comprising: contacting a first in vitro kidney tissue with a test agent; immunostaining the first in vitro kidney tissue and a second in vitro kidney tissue for biomarkers indicative of nephrotoxicity, wherein nephrotoxicity is characterized as the first in vitro kidney tissue having an increased level of the biomarker relative to the second in vitro kidney tissue that was not contacted with the test agent. Non-limiting examples of biomarkers indicative of nephrotoxicity can include: kidney injury molecule-1 (KIM-1), cystatin C, neutrophil gelatinase-associated lipocalin (NGAL), clusterin, an interleukin 18.

Provided herein are kits and reagents for treating a subject with a kidney disease. Provided herein is a kit comprising: a first container comprising: (a) a population of ureteric bud kidney cells, (b) a population of nephron progenitor cells, or (c) an in vitro kidney tissue provided herein; and a second container comprising: (a) a therapeutic agent for treating a kidney disease; (b) one or more immunosuppressants; or (c) a therapeutic agent for treating a kidney disease and an immunosuppressant. The one or more immunosuppressants can be administered before kidney tissue transplantation, simultaneously with kidney tissue transplantation, and/or after kidney tissue transplantation. The therapeutic agent for treating a kidney disease can be administered to a subject before, simultaneous, or after treatment with a kidney tissue provided herein or treating a subject with a kidney-tissue filtered blood circuit. Methods of treating a subject are described further below.

(7) Methods of Treatment, Dosing, and Administration.

Provided herein are methods of treating a subject with a disease or a condition. In some embodiments, the methods comprise using a kidney tissue-filtered blood circuit. The kidney tissues provided here can be included as part of a blood circuit that can be used ex-vivo while a subject is waiting for an organ transplantation, to assist with organ transplantation, or to prolong survival of a subject with a lethal kidney disease. In some embodiments, the methods comprise producing a blood circuit, wherein the blood circuit comprises blood from the subject in fluid communication with a kidney or a kidney tissue(s) provided herein, wherein the kidney or the kidney tissue(s) filters blood from the subject, thereby treating a kidney disease in the subject. The kidney tissues can be maintained in a bioreactor receiving the patient's blood for filtration. Following filtration of the patient's blood by the kidney tissues, the filtered blood is returned back to the patient with excess waste chemicals and water removed from the blood.

Provided herein are methods of treating a disease in a subject, wherein the methods comprise: transplanting an in vitro kidney, an in vitro kidney tissue, a composition, or a system provided herein into a subject. In some embodiments, the transplanting comprises surgical removal of a diseased kidney and replacing the diseased kidney with the in vitro kidney, in vitro kidney tissue, composition, or system. In some embodiments, the transplanting comprises engrafting the in vitro kidney, in vitro kidney tissue, composition, or system into an existing kidney or kidney tissue in the subject.

The transplant composition can comprise a given number or dose of cells sufficient to perform blood filtration. In some embodiments, a dose of cells is administered to subjects in accord with the provided methods. In some embodiments, the size or timing of the doses is determined as a function of the particular disease or condition in the subject. It is within the level of a skilled artisan to empirically determine the size or timing of the doses for a particular disease in view of the provided description. In certain embodiments, the cells, or individual populations of sub-types of cells, are administered to the subject at a range of about 0.1 million to about 100 billion cells and/or that amount of cells per kilogram of body weight of the subject, such as, e.g., 0.1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), such as about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), and in some cases about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells) or any value in between these ranges and/or per kilogram of body weight of the subject. Dosages may vary depending on attributes particular to the disease or disorder and/or patient and/or other treatments.

In some embodiments, the methods provided herein comprise administering to a subject a kidney tissue provided herein that comprises at least or at least about $0.1\times10^6$ cells/kg body weight of the subject, $0.2\times10^6$ cells/kg, $0.3\times10^6$ cells/kg, $0.4\times10^6$ cells/kg, $0.5\times10^6$ cells/kg, $1\times10^6$ cell/kg, $2.0\times10^6$ cells/kg, $3\times10^6$ cells/kg or $5\times10^6$ cells/kg. In some embodiments, the methods provided herein comprise administering to a subject a kidney tissue provided herein that comprises a number of cells that is between or between about $0.1\times10^6$ cells/kg body weight of the subject and $1.0\times10^7$ cells/kg, between or between about $0.5\times10^6$ cells/kg and $5\times10^6$ cells/kg, between or between about $0.5\times10^6$ cells/kg and $3\times10^6$ cells/kg, between or between about $0.5\times10^6$ cells/kg and $2\times10^6$ cells/kg, between or between about $0.5\times10^6$ cells/kg and $1\times10^6$ cell/kg, between or between about $1.0\times10^6$ cells/kg body weight of the subject and $5\times10^6$ cells/kg, between or between about $1.0\times10^6$ cells/kg and $3\times10^6$ cells/kg, between or between about $1.0\times10^6$ cells/kg and $2\times10^6$ cells/kg, between or between about $2.0\times10^6$ cells/kg body weight of the subject and $5\times10^6$ cells/kg, between or between about $2.0\times10^6$ cells/kg and $3\times10^6$ cells/kg, or between or between about $3.0\times10^6$ cells/kg body weight of the subject and $5\times10^6$ cells/kg, each inclusive.

In some embodiments, the subject that is to be treated with a kidney tissue, a composition, a blood circuit, or a system provided herein has, is diagnosed with, or is suspected of having a disease or condition. Relevant diseases that may require organ transplantation include but are not limited to: organ failure, kidney failure, diabetes, polycystic kidney disease, cardiovascular disease, edema, birth defects, genetic diseases, autoimmune disease, and any combinations thereof. In some embodiments, the subject to be treated with a kidney tissue, a composition, a blood circuit, or a system provided herein has, is diagnosed with, or is suspected of having a kidney disease or a kidney condition. Non-limiting examples of kidney diseases and conditions include: atypical hemolytic uremic syndrome (aHUS), Alport syndrome, amyloidosis, POL1-mediated kidney disease, cancer, cardiovascular kidney metabolic (CKM) syndrome, complement 3 glomerulopathy (C3G), cystinosis, diabetic kidney disease, end-stage renal failure, Fabry disease, focal segmental glomerulosclerosis (FSGS). Glomerulonephritis (Glomerular Disease) Goodpasture syndrome, granulomatosis with polyangiitis (GPA), hemolytic uremic syndrome (HUS), Henoch-Schonlein purpura (HSP), IgA nephropathy, interstitial nephritis, kidney failure, Lupus nephritis, minimal change disease, polycystic kidney disease, chronic kidney disease (CKD), primary hyperoxaluria and oxalate, thrombotic thrombocytopenic purpura (TTP), and vasculitis of the kidney. In some embodiments, the subject to be treated with a kidney tissue, a composition, a blood circuit, or a system provided herein has, is diagnosed with, or is suspected of having kidney failure. In some embodiments, the kidney failure is caused by one or more conditions selected from the group consisting of: diabetes, high blood pressure, glomerulonephritis, polycystic kidney disease, lupus nephritis, IgA nephropathy, alcoholism, and nephrotoxicity. In some embodiments, the subject to be treated with a kidney tissue, a composition, a blood circuit, or a system provided herein has, or is diagnosed with a kidney injury. In some embodiments, the kidney injury is caused by an infection (e.g., acute pyelonephritis or septicemia), a pregnancy complication (e.g., placental abruption or placenta previa), a urinary tract obstruction, kidney stones, or a physical injury (e.g., an automobile accident). In some embodiments, the subject to be treated with a kidney tissue, a composition, a blood circuit, or a system provided herein has, or is diagnosed with a congenital abnormality. In some embodiments, the subject has or is diagnosed with renal agenesis, renal dysplasia, renal hypoplasia. Renal agenesis is the absence of one or both kidneys at birth. In some embodiments, the subject has or is diagnosed with polycystic kidney disease (PKD). PKD is a genetic condition in which multiple cysts (abnormal sacs containing fluid) grow in the kidneys. If not properly treated and managed, PKD can lead to kidney failure. There are two types of PKD which include Autosomal dominant polycystic kidney disease (ADPKD) and Autosomal recessive polycystic kidney disease (ARPKD). Autosomal dominant PKD is represents about 90 percent of all PKD cases, symptoms of ADPKD typically present between the ages of 30 and 40. However, some patients do develop symptoms as children. Autosomal recessive polycystic kidney disease (ARPKD) is a rare form of PKD and symptoms of this condition begin very early in life, even while still in the womb.

The methods of treating a subject with a disease or condition provided herein can ameliorate at least one symptom of a disease. In some embodiments, the methods can ameliorate at least one symptom of a disease by at least 1%, at least 2%, at least 3%, at least 4%, at least 5%, at least 10%, or at least 20% relative to the symptom prior to treatment. Non-limiting examples of symptoms associated with a disease, such as a kidney disease include: formation of renal cysts, renal insufficiency, urinary tract infections, hematuria (blood in the urine), high blood pressure, kidney stones, aneurysms (bulges in the walls of blood vessels), burning or difficulty during urination, an increase in the frequency of urination, volume retention (e.g. puffiness around the eyes, swelling of the hands and feet), pain in the small of the back just below the ribs, fatigue, pale skin, joint pain, fingernail and toenail abnormalities, bruising, foamy urine, loss of appetite, nausea, vomiting, poor growth, fevers, swollen stomach, a reduction in the glomerular filtration rate (GFR), albuminuria, and proteinuria.

In some embodiments, the methods provided herein increase glomerular filtration rate (GFR) in a subject relative to the GFR of the subject prior to treatment with a composition or system provided herein as determined by a glomerular filtration rate blood test. GFR is a blood test that measures how well kidneys remove waste, toxins, and extra fluid from the blood. GFR is usually measured in milliliters per minute per 1.73 square meters of body surface area (mL/min/1.73 $m^2$). Serum creatinine level, age, and sex are used to calculate GFR. Generally, in humans, a GFR of 60 or higher indicates that the subject has functioning kidneys and is generally healthy. A GFR less than 60 can indicate that the human subject has a kidney disease. A GFR that is less than 15 indicates that a patient has kidney failure. A GFR level of less than 20 over 6 to 12 months indicates that a subject is in need of a kidney transplantation or dialysis to survive. In some embodiments, the methods provided herein increase glomerular filtration rate (GFR) in a subject by at least 5, at least 10, at least 15, at least 20, at least 25, at least 30, at least 35, at least 40, at least 45, at least 50, at least 55, or at least 60 mL/min/1.73 $m^2$.

In some embodiments, the methods provided herein decrease the level of urea in the blood relative to the level of urea in the blood of a subject prior to treatment with a composition or system provided herein as determined by a creatinine test. In some embodiments, the methods provided herein decrease the level of creatinine in the blood relative to the level of creatinine in the subject prior to treatment with a composition or system provided herein as determined by a blood urea nitrogen test.

In some embodiments, the methods provided herein decrease blood pressure in a subject relative to the blood pressure in the subject prior to treatment with a composition or system provided herein.

In some embodiments, the methods provided herein reduce the level of a biomarker indicative of nephrotoxicity in a kidney of a subject relative to the level of the biomarker indicative of nephrotoxicity prior to treatment. The biomarker can be measured by taking a kidney biopsy or a blood sample from a subject prior to treatment and after treatment with a transplant composition or an ex-vivo blood circuit; and performing an assay that measures the level of the biomarker. For example, the assay can include immunohistochemistry and microscopy techniques, RT-PCR, or sequencing.

The methods provided herein can further comprise administering to the subject a therapeutically effective amount of an additional therapeutic agent. The additional therapeutic agent can include, for example, an immunosuppressant, an anti-inflammatory, a therapeutic for treating a kidney disease, an immunotherapy, or an adoptive cell therapy. In some embodiments, the subject is administered a therapeutic for treating a kidney disease before, after, or during transplantation of a transplant composition provided herein. In some embodiments, the subject is administered a therapeutic for treating a kidney disease before, after, or during treatment with an ex-vivo blood circuit provided herein. In some embodiments, the subject is administered an immunosuppressant before, after, or during transplantation of a transplant composition provided herein.

In some embodiments, the therapeutic for treating a kidney disease comprises a sodium-glucose cotransporter-2 (SGLT2) inhibitor, an angiotensin-converting enzyme (ACE) inhibitor, an angiotensin receptor blocker (ARB), a beta blocker, a diuretic, a potassium binder, a statin, an erythropoiesis-stimulating agent, an iron supplement, a phosphate binder, a calcium supplement, a vitamin D supplement, a calcimimetic, an aldosterone antagonist, a corticosteroid, metformin, a GLP-1 inhibitor, aspirin, a non-steroidal anti-inflammatory drug (NSAID), or any combination thereof. In some embodiments, the SGLT2 inhibitor comprises canagliflozin (Invokana), dapagliflozin (Forxiga), empagliflozin (Jardiance), ertugliflozin (Steglatro), analogues, derivatives, salts, or a combination thereof. In some embodiments, the ACE inhibitor comprises: benazepril (Lotensin), captopril (Capoten), enalapril (Vasotec), fosinopril (Monopril), lisinopril (Zestril and Prinivil), moexipril (Univasc), perindopril (Aceon), quinapril (Accupril), ramipril: (Altace), trandolapril (Mavik), analogues, derivatives, salts, or a combination thereof. In some embodiments, the diuretic comprises indapamide, bumetanide, chlorothiazide, furosemide, hydrochlorothiazide, metolazone, spironolactone, thiazide, amiloride, chlorthalidone, eplerenone, ethacrynic acid, torsemide, bendroflumethiazide, dyrenium, edecrin, triamterene analogues, derivatives, salts, or a combination thereof. In some embodiments, the statin comprises atorvastatin (Lipitor), fluvastatin (Lescol XL), lovastatin (Altoprev), pitavastatin (Livalo), pravastatin (Pravachol), rosuvastatin (Crestor), simvastatin (Zocor), analogues, derivatives, salts, or a combination thereof. Acebutolol. In some embodiments, the beta blocker comprises atenolol (Tenormin), bisoprolol, metoprolol (Lopressor, Toprol XL), nadolol (Corgard), nebivolol (Bystolic), propranolol (Inderal LA, InnoPran XL), analogues, derivatives, salts, or a combination thereof.

EXEMPLARY EMBODIMENTS

Provided herein are in vitro-lumenized kidneys or in vitro-lumenized kidney tissues, wherein the in vitro-lumenized kidneys or in vitro-lumenized kidney tissues comprise: a sequential arrangement of a plurality of uretic bud (UB) kidney tissues; wherein the plurality of UB kidney tissues are contiguously fused from at least one connecting point, and wherein the in vitro-lumenized kidney comprises a continuous lumen that is capable of facilitating fluid flow through the lumen. Further provided herein are in vitro-lumenized kidneys or in vitro-lumenized kidney tissues, wherein the sequential arrangement comprises adjacent UB kidney tissues of the plurality of UB kidney tissues in a proximity sufficient to contiguously fuse at the at least one connecting point. Further provided herein are in vitro-lumenized kidneys or in vitro-lumenized kidney tissues, wherein the at least one connecting point comprises: (a) a tip of a UB kidney tissue of the plurality of UB kidney tissues; (b) a stalk a UB kidney tissue of the plurality of UB kidney tissues; (c) a tip of a UB kidney tissue and a stalk of a UB kidney tissue; (d) one or more tips of an adjacent UB kidney tissue of the plurality of UB kidney tissues; (e) one or more stalks of an adjacent UB kidney tissue of the plurality of UB kidney tissues; (f) two or more tips of adjacent UB kidney tissues of the plurality of UB kidney tissues; (g) two or more stalks of adjacent UB kidney tissues of the plurality of UB kidney tissues; (h) cells isolated from (a)-(c) or a combination thereof; or (i) a combination of any one of (a)-(h). Further provided herein are in vitro-lumenized kidneys or in vitro-lumenized kidney tissues, wherein the in vitro-lumenized kidney tissue expresses a marker selected from the group consisting of: PAX2, RET1, SOX9, CK8, cKit, CXCR4, or a combination thereof. Further provided herein are in vitro-lumenized kidneys or in vitro-lumenized kidney tissues, wherein the tip expresses a RET1 marker and a SOX9 marker. Further provided herein are in vitro-lumenized kidneys or in vitro-lumenized kidney tissues, wherein the one or more tips each express a RET1 marker and a SOX9 marker. Further provided herein are in vitro-lumenized kidneys or in vitro-lumenized kidney tissues, wherein the stalk expresses a CK8 marker. Further provided herein are in vitro-lumenized kidneys or in vitro-lumenized kidney tissues, wherein the one or more stalks each express a CK8 marker. Further provided herein are in vitro-lumenized kidneys or in vitro-lumenized kidney tissues, wherein the sequential arrangement comprises a linear pattern or a circular pattern. Further provided herein are in vitro-lumenized kidneys or in vitro-lumenized kidney tissues, wherein a portion of a core and/or the lumen of each of the plurality of UB kidney tissues comprise epithelial cells. Further provided herein are in vitro-lumenized kidneys or in vitro-lumenized kidney tissues, wherein a portion of a core and/or the lumen each of the plurality of UB kidney tissues comprise renal stromal cells. Further provided herein are in vitro-lumenized kidneys or in vitro-lumenized kidney tissues, wherein a portion of a core and/or the lumen of the plurality of UB kidney tissues comprise epithelial cells and renal stromal cells. Further provided herein are in vitro-lumenized kidneys or in vitro-lumenized kidney tissues, wherein the plurality of UB kidney tissues are (i) are generated from Wolffian duct progenitor cells; (ii) are derived from Wolffian duct progenitor cells; (iii) comprise Wolffian duct progenitor cells; (iv) comprise cells expressing a PAX2 marker; (v) comprise cells expressing a CXCR4 marker; or (vi) comprise cell expressing a cKit marker. Further provided herein are in vitro-lumenized kidneys or in vitro-lumenized kidney tissues, wherein the plurality of UB kidney tissues comprise a population of cells enriched for or sorted for a CXCR4 marker. Further provided herein are in vitro-lumenized kidneys or in vitro-lumenized kidney tissues, wherein the plurality of UB kidney tissues express a CXCR4 marker and a cKit marker. Further provided herein are in vitro-lumenized kidneys or in vitro-lumenized kidney tissues, wherein the in vitro-lumenized kidney tissue comprises mammalian cells. Further provided herein are in vitro-lumenized kidneys or in vitro-lumenized kidney tissues, wherein the in vitro-lumenized kidney tissue comprises human cells. Further provided herein are in vitro-lumenized kidneys or in vitro-lumenized kidney tissues, wherein the in vitro-lumenized kidney tissue comprises a population of stem cells or comprises a population of in vitro-differentiated progeny of a population of stem cells. Further provided herein are in vitro-lumenized kidneys or in vitro-lumenized kidney tissues, wherein the stem cells are adult stem cells, induced pluripotent stem cells (iPSCs), or human embryonic cells.

Provided herein are compositions, wherein the compositions comprise the in vitro-lumenized kidney tissue provided herein or the in vitro-lumenized kidney provided herein. Further provided herein are compositions, further comprising a cell culture medium.

Further provided herein are compositions comprising growth factors, wherein the growth factors comprise CHIR99021, Activin A, FGF9, FGF1, BMP4, Retinoic Acid, GDNF1, RSPO1, FGF7, or a combination thereof. Further provided herein are compositions, further comprising one or more metabolites. Further provided herein are compositions, wherein the one or more metabolites comprise: urea, creatinine, uric acid, ammonium phosphate, or a combination thereof. Further provided herein are compositions, further comprising an extracellular matrix. Further provided herein are compositions, wherein the extracellular matrix comprises: extracellular matrix comprises a solubilized basement membrane preparation extracted from Engelbreth-Holm-Swarm (EHS) mouse sarcoma, laminin, collagen IV, heparan sulfate proteoglycans, entactin, fibronectin, vitronectin, retronectin, elastin, hyaluronic acid, methylcellulose, a gelatin, or any combination thereof. Further provided herein are compositions, further comprising a diluent. Further provided herein are compositions, wherein the diluent comprises a cryopreservation agent, a serum, or a suspension. Further provided herein are compositions, further comprising a population of nephron progenitor cells or a differentiated progeny thereof. Further provided herein are compositions, further comprising a population of human blood cells.

Provided herein are methods for generating lumenized kidney tissues in vitro, wherein the methods comprise: generating a plurality of ureteric bud (UB) kidney tissues from ureteric bud progenitor cells (UBPCs); arranging the plurality of UB kidney tissues in a sequential configuration and in a proximity sufficient to form fused UB kidney tissues that are contiguously fused from at least one connecting point; and culturing the fused UB kidney tissues, thereby forming a lumenized kidney that is capable of facilitating fluid flow through the lumenized kidney. Further provided herein are methods, wherein the generating comprises aggregating the UBPCs using centrifugation and differentiating the aggregated UBPCs in a first culture medium. Further provided herein are methods, wherein the generating comprises culturing the UBPCs in a suspension culture. Further provided herein are methods, wherein the arranging further comprises juxtaposing the plurality of UB kidney tissues. Further provided herein are methods, wherein culturing the fused UB kidney tissues comprises embedding the fused UB kidney tissues in a branching culture medium, wherein the branching culture medium comprises retinoic acid, RSPO1, a neurotrophic factor, a fibroblast growth factor, a bone morphogenetic pathway inhibitor, an extracellular matrix, or a combination thereof. Further provided herein are methods, wherein culturing the fused UB kidney tissues comprises culturing the fused UB kidney tissues in a static culture medium. Further provided herein are methods, wherein the at least one connecting point comprises: (a) a tip of a UB kidney tissue of the plurality of UB kidney tissues; (b) a stalk a UB kidney tissue of the plurality of UB kidney tissues; (c) a tip of a UB kidney tissue and a stalk of a UB kidney tissue; (d) one or more tips of an adjacent UB kidney tissue of the plurality of UB kidney tissues; (e) one or more stalks of an adjacent UB kidney tissue of the plurality of UB kidney tissues; (f) two or more tips of adjacent UB kidney tissues of the plurality of UB kidney tissues; (g) two or more stalks of adjacent UB kidney tissues of the plurality of UB kidney tissues; (h) cells isolated from (a)-(c) or a combination thereof; or (i) a combination of any one of (a)-(h). Further provided herein are methods, wherein the tip comprises a RET1 marker, a SOX9 marker, or a combination thereof. Further provided herein are methods, wherein the stalk comprises a CK8 marker. Further provided herein are methods, wherein the sequential configuration comprises a linear pattern or a circular pattern. Further provided herein are methods, wherein a portion of a core of the UB kidney tissues comprise epithelial cells and renal stromal cells. Further provided herein are methods, wherein a portion of a core of the UB kidney tissues comprise renal stromal cells. Further provided herein are methods, wherein a portion of a core of the UB kidney tissues comprise epithelial cells and renal stromal cells. Further provided herein are methods, wherein the UBPCs comprise Wolffian duct progenitor cells or cells that express a PAX2 marker. Further provided herein are methods, wherein the plurality of UB kidney tissues express a CXCR4 marker.

Provided herein are in vitro kidney compositions, wherein the in vitro kidney compositions comprise: a population of nephron progenitor cells (NPCs); and a lumenized kidney tissue comprising a plurality of ureteric bud (UB) kidney tissues that have been fused while arranged in a sequential configuration; wherein the population of NPCs are in contact with the UB kidney tissues while at least partially immersed in a culture medium, thereby forming a tubular network that is capable of facilitating fluid flow through the lumenized kidney tissue. Further provided herein are in vitro kidney compositions, wherein the sequential configuration comprises adjacent UB kidney tissues of the plurality of UB kidney tissues in a proximity sufficient to contiguously fuse from at least one connecting point. Further provided herein are in vitro kidney compositions, wherein the at least one connecting point comprises: (a) a tip of a UB kidney tissue of the plurality of UB kidney tissues; (b) a stalk a UB kidney tissue of the plurality of UB kidney tissues; (c) a tip of a UB kidney tissue and a stalk of a UB kidney tissue; (d) one or more tips of an adjacent UB kidney tissue of the plurality of UB kidney tissues; (e) one or more stalks of an adjacent UB kidney tissue of the plurality of UB kidney tissues; (f) two or more tips of adjacent UB kidney tissues of the plurality of UB kidney tissues; (g) two or more stalks of adjacent UB kidney tissues of the plurality of UB kidney tissues; (h) cells isolated from (a)-(c) or a combination thereof; or (i) a combination of any one of (a)-(h). Further provided herein are in vitro kidney compositions, wherein the tip comprises a RET1 marker, a SOX9 marker, or a combination thereof. Further provided herein are in vitro kidney compositions, wherein the stalk comprises a CK8 marker. Further provided herein are in vitro kidney compositions, wherein the sequential configuration comprises a linear pattern or a circular pattern. Further provided herein are in vitro kidney compositions, wherein a portion of a core of each of the plurality of UB kidney tissues comprise epithelial cells. Further provided herein are in vitro kidney compositions, wherein a portion of a core of each of the plurality of UB kidney tissues comprise renal stromal cells. Further provided herein are in vitro kidney compositions, wherein a portion of a core of each of the plurality of UB kidney tissues comprise epithelial cells and renal stromal cells. Further provided herein are in vitro kidney compositions, wherein the plurality of UB kidney tissues are (i) are generated from Wolffian duct progenitor cells; (ii) are derived from Wolffian duct progenitor cells; (iii) comprise Wolffian duct progenitor cells; (iv) comprise cells expressing a PAX2 marker; (v) comprise cells expressing a CXCR4 marker; or (vi) comprise cell expressing a cKit marker. Further provided herein are in vitro kidney compositions, wherein the plurality of UB kidney tissues express a CXCR4 marker and a cKit marker. Further provided herein are in vitro kidney compositions, further comprising a cell culture medium. Further provided herein are in vitro kidney compositions, further comprising growth factors. Further provided herein are in vitro kidney compositions, wherein the growth factors comprise CHIR99021, Activin A, FGF9, FGF1, BMP4, Retinoic Acid, GDNF1, RSPO1, FGF7, or a combination thereof. Further provided herein are in vitro kidney compositions, further comprising one or more metabolites. Further provided herein are in vitro kidney compositions, wherein the one or more metabolites comprise urea, creatinine, uric acid, ammonium phosphate, or a combination thereof. Further provided herein are in vitro kidney compositions, further comprising an extracellular matrix. Further provided herein are in vitro kidney compositions, wherein the extracellular matrix comprises: extracellular matrix comprises a solubilized basement membrane preparation extracted from Engelbreth-Holm-Swarm (EHS) mouse sarcoma, laminin, collagen IV, heparan sulfate proteoglycans, entactin, fibronectin, vitronectin, retronectin, elastin, hyaluronic acid, methylcellulose, a gelatin, or any combination thereof. Further provided herein are in vitro kidney compositions, further comprising a diluent. Further provided herein are in vitro kidney compositions, wherein the diluent comprises a cryopreservation agent, a serum, or a suspension.

Provided herein are methods for making an in vitro kidney tissue, wherein the methods comprise: generating a plurality of ureteric bud (UB) kidney tissues from ureteric bud progenitor cells (UBPCs); arranging the plurality of UB kidney tissues in a sequential configuration and in a sufficient proximity to form fused UB kidney tissues from at least one connecting point; culturing the fused UB kidney tissues, thereby forming a lumenized kidney that is capable of facilitating flow through the lumenized kidney; combining the lumenized kidney with a population of nephron progenitor cells (NPCs); and allowing the combination of the lumenized kidney and the NPCs to form a contiguous tubular network. Further provided herein are methods, wherein the generating comprises aggregating the UBPCs using centrifugation and differentiating the aggregated UBPCs in a first culture medium. Further provided herein are methods, wherein the generating comprises culturing the UBPCs in a suspension culture. Further provided herein are methods, wherein the arranging further comprises juxtaposing the plurality of UB kidney tissues. Further provided herein are methods, wherein culturing the fused UB kidney tissues comprises embedding the fused UB kidney tissues in a branching culture medium, wherein the branching culture medium comprises retinoic acid, RSPO1, a neurotrophic factor, a fibroblast growth factor, a bone morphogenetic pathway inhibitor, an extracellular matrix, or a combination thereof. Further provided herein are methods, wherein culturing the fused UB kidney tissues comprises culturing the fused UB kidney tissues in a static culture medium. Further provided herein are methods, wherein the at least one connecting point comprises: (a) a tip of a UB kidney tissue of the plurality of UB kidney tissues; (b) a stalk a UB kidney tissue of the plurality of UB kidney tissues; (c) a tip of a UB kidney tissue and a stalk of a UB kidney tissue; (d) one or more tips of an adjacent UB kidney tissue of the plurality of UB kidney tissues; (e) one or more stalks of an adjacent UB kidney tissue of the plurality of UB kidney tissues; (f) two or more tips of adjacent UB kidney tissues of the plurality of UB kidney tissues; (g) two or more stalks of adjacent UB kidney tissues of the plurality of UB kidney tissues; (h) cells isolated from (a)-(c) or a combination thereof; or (i) a combination of any one of (a)-(h). Further provided herein are methods, wherein the tip expresses a RET1 marker and a SOX9 marker. Further provided herein are methods, wherein the stalk expresses a CK8 marker. Further provided herein are methods, wherein the sequential configuration comprises a linear pattern or a circular pattern. Further provided herein are methods, wherein a portion of a core of each of the plurality of UB kidney tissues comprise epithelial cells. Further provided herein are methods, wherein a portion of a core of each of the plurality of UB kidney tissues comprise renal stromal cells. Further provided herein are methods, wherein a portion of a core of each of the plurality of UB kidney tissues comprise epithelial cells and renal stromal cells. Further provided herein are methods, wherein the UBPCs comprise Wolffian duct progenitor cells or cells that express a PAX2 marker. Further provided herein are methods, wherein the plurality of UB kidney tissues express a CXCR4 marker.

Provided herein are in vitro compositions, wherein the in vitro compositions comprise: an in vitro-differentiated kidney tissue comprising a population of nephron progenitor cells (NPCs) connected to a population of fragmented ureteric bud (UB) kidney tissues, wherein the in vitro-differentiated kidney tissue comprises repeating units of nephric-ureteric connections in a sequential configuration. Further provided herein are in vitro compositions, wherein each unit is at least about 1 millimeters (mm) to about 10 mm in size. Further provided herein are in vitro compositions, wherein the repeating units of nephric-ureteric connections express a nephron marker and a ureteric bud (UB) marker. Further provided herein are in vitro compositions, wherein the repeating units of nephric-ureteric connections express two or more markers selected from: CK8, MAFB, LRP, and GATA3. Further provided herein are in vitro compositions, wherein the repeating units of nephric-ureteric connections express a nephron marker, wherein the nephron marker comprises MAFB or LRP2. Further provided herein are in vitro compositions, wherein the repeating units of nephric-ureteric connections express a UB marker, wherein the UB marker is selected from the group consisting of RET1, SOX9, CK8, and GATA3. Further provided herein are in vitro compositions, wherein the repeating units of nephric-ureteric connections comprise two or more markers selected from the group consisting of AQP2, CALB1, CD13, CDH1, CK8, cKit, CUBN, cystatin C, CXCR4, DAPL1, ECAD, EMX2, EN2, GATA3, HNF4A, HNF1B, LGR5, LGR6, LHX1, Lotus Tetragonolobus Lectin (LTL), LRP2, LYPD1, MAFB, PAX2, PAX8, PECAM1, PODXL, RET1, serum creatinine (SCr), SIX1, SIX2, Special AT-rich sequence-binding protein (SATB2), SOX9, SOX17, parathyroid hormone 1 receptor (PTH1R), claudin 2 (CLDN2), tight junction protein 3 (TJP3), TCF21, WNT4, WNT9, and WNT11.

Provided herein are in vitro compositions, wherein the in vitro compositions comprise: an in vitro-differentiated kidney tissue comprising a population of nephron progenitor cells (NPCs) connected to a population of fragmented ureteric bud (UB) kidney tissues, wherein: the in vitro-differentiated kidney tissue comprises a collecting duct, and the in vitro-differentiated kidney tissue comprises a glomerular marker, a proximal tubule marker, a tubular epithelium marker, and a connecting segment marker. Further provided herein are in vitro compositions, wherein the glomerular markers comprises MAFB, WT1, nephrin, or podocin. Further provided herein are in vitro compositions, wherein the proximal tubule marker comprises LRP2, LTL, CUBN, PTH1R, AQP1, CLDN2, TJP3, or CD13. Further provided herein are in vitro compositions, wherein the tubular epithelium marker comprises CK8, AQP isoforms, CD34, WGA lectin. Further provided herein are in vitro compositions, wherein connecting segment marker comprises GATA3 or AQP2. Further provided herein are in vitro compositions, wherein the collecting duct expresses a marker selected from: GATA3, EPCAM, and ECAD. Further provided herein are in vitro compositions, wherein the collecting duct comprises a lumen. Further provided herein are in vitro compositions, wherein the lumen facilitates fluid flow through the lumen when the in vitro composition is in contact with a fluid.

Provided herein are in vitro compositions, wherein the in vitro compositions comprise: an in vitro-differentiated kidney tissue comprising a population of nephron progenitor cells (NPCs) connected to a population of fragmented ureteric bud (UB) kidneys, wherein: the in vitro-differentiated kidney tissue that comprises a collecting duct, and the in vitro-differentiated kidney tissue comprises two or more markers selected from: LRP2, GATA3, MAFB, and CK8. Further provided herein are in vitro compositions, wherein the in vitro-differentiated kidney tissue comprises two or more markers, wherein the two or more markers comprise: (i) MAFB and LRP2; (ii) MAFB and CK8; (iii) MAFB and GATA3; (iv) LRP2 and CK8; (v) LRP2 and GATA3; or (vi) CK8 and GATA3. Further provided herein are in vitro compositions, wherein the in vitro-differentiated kidney tissue comprises three or more markers, wherein the three or more markers comprise: (i) MAFB, LRP2, and CK8; (ii) MAFB, LRP2, and GATA3; (iii) MAFB, CK8, and GATA3; or (iv) LRP2, CK8, and GATA3. Further provided herein are in vitro compositions, wherein the in vitro-differentiated kidney tissue comprises four or more markers, wherein the four or more markers comprise: MAFB, LRP2, CK8, and GATA3. Further provided herein are in vitro compositions, wherein the population of NPCs are derived from human stem cells. Further provided herein are in vitro compositions, wherein the population of fragmented ureteric bud (UB) kidney tissues are derived from human stem cells. Further provided herein are in vitro compositions, wherein the human stem cells are embryonic stem cells, induced pluripotent stem cells (iPSCs), or adult stem cells. Further provided herein are in vitro compositions, wherein a portion of a core of the UB kidney tissues comprise epithelial cells. Further provided herein are in vitro compositions, wherein a portion of a core of the UB kidney tissues comprise renal stromal cells. Further provided herein are in vitro compositions, wherein a portion of a core of the UB kidney tissues comprise epithelial cells and renal stromal cells. Further provided herein are in vitro compositions, wherein the UB kidney tissues are (i) are generated from Wolffian duct progenitor cells; (ii) are derived from Wolffian duct progenitor cells; (iii) comprise Wolffian duct progenitor cells; (iv) comprise cells expressing a PAX2 marker; (v) comprise cells expressing a CXCR4 marker; or (vi) comprise cell expressing a cKit marker. Further provided herein are in vitro compositions, wherein the UB kidney tissues express a CXCR4 marker. Further provided herein are in vitro compositions, further comprising a cell culture medium. Further provided herein are in vitro compositions, further comprising growth factors. Further provided herein are in vitro compositions, wherein the growth factors comprise CHIR99021, Activin A, FGF9, FGF1, BMP4, Retinoic Acid, GDNF1, RSPO1, FGF7, or a combination thereof. Further provided herein are in vitro compositions, further comprising one or more metabolites. Further provided herein are in vitro compositions, wherein the one or more metabolites comprise urea, creatinine, uric acid, ammonium phosphate, or a combination thereof. Further provided herein are in vitro compositions, further comprising an extracellular matrix. Further provided herein are in vitro compositions, wherein the extracellular matrix comprises: extracellular matrix comprises a solubilized basement membrane preparation extracted from Engelbreth-Holm-Swarm (EHS) mouse sarcoma, laminin, collagen IV, heparan sulfate proteoglycans, entactin, fibronectin, vitronectin, retronectin, elastin, hyaluronic acid, methylcellulose, a gelatin, or any combination thereof. Further provided herein are in vitro compositions, further comprising a diluent. Further provided herein are in vitro compositions, wherein the diluent comprises a cryopreservation agent, a serum, or a suspension.

Provided herein are methods for making an in vitro kidney tissue, wherein the methods comprise: generating a plurality of ureteric bud (UB) kidneys from ureteric bud progenitor cells (UBPCs) optionally wherein the UBPCs comprise Wolffian duct progenitor cells; fragmenting the plurality of UB kidney tissues into UB fragments; generating a plurality of nephron progenitor cells (NPCs); combining the UB fragments and NPCs in a first culture medium thereby forming a combined cell population; and arranging the combined cell population in a second culture medium in a spatially defined location sufficient to form repeating units of nephric-ureteric connections. Further provided herein are methods, wherein the generating in (a) comprises aggregating the UBPCs using centrifugation and differentiating the aggregated UBPCs in a first culture medium. Further provided herein are methods, wherein the generating in (a) comprises culturing the UBPCs in a suspension culture. Further provided herein are methods, wherein the arranging further comprises juxtaposing the plurality of UB kidney tissues. Further provided herein are methods, wherein a portion of a core of the UB kidney tissues comprise epithelial cells and renal stromal cells. Further provided herein are methods, wherein a portion of a core of the UB kidney tissues comprise renal stromal cells. Further provided herein are methods, wherein a portion of a core of the UB kidney tissues comprise epithelial cells and renal stromal cells. Further provided herein are methods, wherein the UBPCs comprise Wolffian duct progenitor cells or cells that express PAX2. Further provided herein are methods, wherein the plurality of UB kidney tissues comprise a CXCR4 marker. Further provided herein are methods, wherein the arranging comprises bioprinting the combined cell population.

Provided herein are in vitro kidney compositions, wherein the in vitro kidney compositions comprise: a population of nephron progenitor cells (NPCs); and a lumenized kidney tissue comprising a plurality of ureteric bud (UB) kidney tissues that have been fused while arranged in a sequential configuration; wherein the ureteric bud (UB) kidney tissues are derived from Wolffian duct progenitor cells, wherein the lumenized kidney tissue comprises a lumen that facilitates fluid flow through the lumen when the in vitro kidney composition is in contact with a fluid.

Provided herein are in vitro kidney compositions, wherein the in vitro kidney compositions comprise: a population of nephron progenitor cells (NPCs); and a lumenized kidney tissue comprising a plurality of ureteric bud (UB) kidney tissues that have been fused while arranged in a sequential configuration; wherein the ureteric bud (UB) kidney tissues express PAX2, wherein the lumenized kidney tissue comprises a lumen that facilitates fluid flow through the lumen when the in vitro kidney composition is in contact with a fluid.

Provided herein are methods for treating a kidney disease in a subject, wherein the methods comprise: (a) culturing a plurality of the in vitro composition, the in vitro kidney composition, or the in vitro-lumenized kidney tissue provided herein in a bioreactor; and (b) forming a blood circuit between the subject's blood and the in vitro composition to remove excess waste and fluid, thereby treating the kidney disease. Further provided herein are methods, wherein the kidney disease is a chronic kidney disease. Further provided herein are methods, wherein the kidney disease is selected from the group consisting of: atypical hemolytic uremic syndrome (aHUS), Alport syndrome, amyloidosis, POL1-mediated kidney disease, cancer, cardiovascular kidney metabolic (CKM) syndrome, complement 3 glomerulopathy (C3G), cystinosis, diabetic kidney disease, end-stage renal failure, Fabry disease, focal segmental glomerulosclerosis (FSGS), glomerulonephritis (Glomerular Disease) Goodpasture syndrome, granulomatosis with polyangiitis (GPA), hemolytic uremic syndrome (HUS), Henoch-Schonlein purpura (HSP), IgA nephropathy, interstitial nephritis, kidney failure, Lupus nephritis, minimal change disease, polycystic kidney disease, primary hyperoxaluria and oxalate, thrombotic thrombocytopenic purpura (TTP), and vasculitis of the kidney. Further provided herein are methods, wherein the subject has, is diagnosed with, or is suspected of having kidney failure. Further provided herein are methods, wherein the kidney failure is caused by one or more conditions selected from the group consisting of diabetes, high blood pressure, glomerulonephritis, polycystic kidney disease, lupus nephritis, IgA nephropathy, alcoholism, and nephrotoxicity. Further provided herein are methods, wherein the subject has, or is diagnosed with a kidney injury. Further provided herein are methods, wherein the kidney injury is caused by an infection, a pregnancy complication, a urinary tract obstruction, a kidney stone, or a physical injury. Further provided herein are methods, wherein the subject has, or is diagnosed with a congenital abnormality. Further provided herein are methods, wherein the subject has, or is diagnosed with the congenital abnormality, wherein the congenital abnormality comprises renal agenesis, renal dysplasia, or renal hypoplasia. Further provided herein are methods, wherein the administering comprises surgical transplantation of the in vitro composition in the subject.

Provided herein are methods for treating a disease in a subject, wherein the methods comprise: administering to the subject the plurality of the in vitro composition, the in vitro kidney composition, or the in vitro-lumenized kidney tissue provided herein, thereby treating the disease in the subject. Further provided herein are methods, wherein the disease is a kidney disease. Further provided herein are methods, wherein the kidney disease is a chronic kidney disease. Further provided herein are methods, wherein the kidney disease is selected from the group consisting of: atypical hemolytic uremic syndrome (aHUS), Alport syndrome, amyloidosis, POL1-mediated kidney disease, cancer, cardiovascular kidney metabolic (CKM) syndrome, complement 3 glomerulopathy (C3G), cystinosis, diabetic kidney disease, end-stage renal failure, Fabry disease, focal segmental glomerulosclerosis (FSGS), glomerulonephritis (Glomerular Disease) Goodpasture syndrome, granulomatosis with polyangiitis (GPA), hemolytic uremic syndrome (HUS), Henoch-Schonlein purpura (HSP), IgA nephropathy, interstitial nephritis, kidney failure, Lupus nephritis, minimal change disease, polycystic kidney disease, primary hyperoxaluria and oxalate, thrombotic thrombocytopenic purpura (TTP), and vasculitis of the kidney. Further provided herein are methods, wherein the subject has, is diagnosed with, or is suspected of having kidney failure. Further provided herein are methods, wherein the kidney failure is caused by one or more conditions selected from the group consisting of: diabetes, high blood pressure, glomerulonephritis, polycystic kidney disease, lupus nephritis, IgA nephropathy, alcoholism, and nephrotoxicity. Further provided herein are methods, wherein the subject has, or is diagnosed with a kidney injury. Further provided herein are methods, wherein the kidney injury is caused by an infection, a pregnancy complication, a urinary tract obstruction, a kidney stone, or a physical injury. Further provided herein are methods, wherein the subject has, or is diagnosed with a congenital abnormality. Further provided herein are methods, wherein the subject has, or is diagnosed with the congenital abnormality, wherein the congenital abnormality comprises renal agenesis, renal dysplasia, or renal hypoplasia. Further provided herein are methods, wherein the administering comprises surgical transplantation of the in vitro composition in the subject.

Provided herein are reagents, wherein the reagents comprise: fetal bovine serum (FBS), retinoic acid, R-spondin 1 (RSPO1) protein, glial-derived neurotrophic factor (GDNF), fibroblast growth factor 1 (FGF1), fibroblast growth factor 7 (FGF7), LDN193189, and solubilized basement membrane preparation extracted from Engelbreth-Holm-Swarm (EHS) mouse sarcoma. Further provided herein are reagents, wherein the FBS is present in an amount that is at least about 1% up to 20% volume by total volume of the reagent (v/v). Further provided herein are reagents, wherein the retinoic acid is present in an amount that is at least about 10 nanoMolar (nM) concentration up to 200 nM concentration. Further provided herein are reagents, wherein the RSPO1 is present in an amount that is at least about 10 nanograms per milliliter (ng/mL) up to 200 ng/mL. Further provided herein are reagents, wherein the GDNF is present in an amount that is at least about 0.1 nanograms per milliliter (ng/mL) up to 5 ng/mL. Further provided herein are reagents, wherein the FGF1 is present in an amount that is at least about 10 nanograms per milliliter (ng/mL) up to 200 ng/mL. Further provided herein are reagents, wherein the FGF7 is present in an amount that is at least about 3 nanograms per milliliter (ng/mL) up to 60 ng/mL. Further provided herein are reagents, wherein the LDN193189 is present in an amount that is at least about 1 nanoMolar (nM) concentration up to 20 nM concentration. Further provided herein are reagents, wherein the solubilized basement membrane preparation extracted from Engelbreth-Holm-Swarm (EHS) mouse sarcoma is present in an amount of at least 5% up to 80% volume by total volume of the reagent (v/v).

Provided herein are kits, wherein the kits comprise: a first container comprising: a population of ureteric bud cells and a population of nephron progenitor cells; and a second container comprising media, growth factors, and agents for making an in vitro kidney tissue.

Provided herein are transplant compositions, wherein the transplant compositions comprise: a first container comprising: the in vitro composition or the in vitro kidney composition provided herein, or a plurality of in vitro compositions or the in vitro kidney compositions provided herein; and a second container comprising: (a) an additional therapeutic agent; (b) one or more immunosuppressant; or (c) a combination thereof.

Provided herein are methods for treating a subject with a kidney disease, wherein the methods comprise: administering to the subject a transplant composition provided herein, thereby treating the kidney disease. Further provided herein are methods, wherein the second container of the transplant composition is administered to the subject prior to the first container. Further provided herein are methods, wherein the second container of the transplant composition is administered to the subject at the same time as the first container. Further provided herein are methods, wherein the second container of the transplant composition is administered to the subject after the first container.

Provided herein are methods for transplanting a kidney in a subject, wherein the methods comprise: engrafting a plurality of the in vitro composition, the in vitro kidney composition, the in vitro-lumenized kidney tissue, or the transplant composition provided herein into a kidney of the subject.

Provided herein are methods, wherein the methods comprise: (a) transplanting the in vitro composition provided herein into the subject having a disease; and (b) administering to the subject one or more immunosuppressive agents, wherein the method increases a glomerular filtration rate (GFR) of the subject relative to the GFR of the subject prior to transplantation. Further provided herein are methods, further comprising surgically removing a diseased kidney from the subject. Further provided herein are methods, wherein the subject has a kidney disease. Further provided herein are methods, wherein the subject has a kidney injury.

Provided herein are methods, wherein the methods comprise: (a) transplanting the in vitro composition provided herein into the subject having a disease; and (b) administering to the subject one or more immunosuppressive agents, wherein the method increases reduces a level of a biomarker indicative of nephrotoxicity in the subject relative to the level of the biomarker indicative of nephrotoxicity in the subject prior to transplantation. Further provided herein are methods, further comprising surgically removing a diseased kidney from the subject. Further provided herein are methods, wherein the subject has a kidney disease. Further provided herein are methods, wherein the subject has a kidney injury.

EXAMPLES

Example 1. Methods of Connecting Ureteric Buds (UBs)

Ureteric bud (UB) tissues were produced. In short, pluripotent stem cells were aggregated at 10,000 cells per tissue in Aggrewell™ 800 plates (StemCell Technologies Catalog #34825) via centrifugation. For differentiation from Day 0 until Day 12.5 of the protocol, cells were cultured in basal Differentiation Medium (DM) consisting of DMEM/F21 supplemented with 2% B27 without retinoic acid, 1% L-Glutamine, 1% insulin-transferrin-selenium (ITS), 1× non-essential amino acids (NEAA), 250 units/mL of penicillin and streptomycin (P/S), and 90 μM 2-mercaptoethanol; all percentages performed v/v.

At time of initial aggregation (Day 0), basal Differentiation Medium was supplemented with 10 μM Y27632, 10 ng/mL Activin A, and 1 ng/mL BMP4 and cultured at 37° C. with 5% $CO_2$ and 95% relative humidity.

The following day, Day 1 aggregates were transferred for further culture in suspension utilizing 96-well round-bottom plates, low attachment T-flask, or vertical wheel bioreactors depending on study size. Day 1 culture medium consisted of basal DM supplemented with 10 μM CHIR99021 and 1 ng/mL BMP4.

On Day 2.5, cultured tissues transitioned to basal DM supplemented with 100 nM retinoic acid, 100 ng/mL FGF9, 100 nM LDN193189, and 100 μM SB431542.

On Day 4.5, cultured tissues transitioned to basal DM supplemented with 100 nM retinoic acid, 100 ng/mL FGF9, 30 nM LDN193189, and 5 μM CHIR99021.

On Day 6.5, all aggregates were collected from suspension culture and pelleted via gentle centrifugation (100 g for 3 minutes). Following two DPBS washes and centrifugations (100 g for 3 minutes), aggregates were digested to single cells using 0.25% Trypsin-EDTA for 6 minutes in a 37° C. water bath. Aggregates were gently triturated with a p1000 pipette to ensure complete dissociation to single cells, followed by addition of DMEM supplemented with 10% Fetal Bovine Serum (FBS) and 0.5% DNase I to stop enzymatic activity. The resulting single cell suspension was centrifuged for 4 minutes at 300 g. The pellet was washed twice with Hanks Buffered Saline Solution (HBSS) supplemented with 20% FBS, 4 mM sodium hydrogen carbonate, 1 mM calcium chloride dihydrate, and 50 μg/mL DNase I, with centrifugation for 4 minutes at 300 g. Cells were then blocked with normal mouse serum for 15 min on ice, with occasional mixing. Cell surface marker staining was carried out in FACS buffer (comprised of HBSS supplemented with 1% bovine serum albumin, and 4 mM sodium hydrogen carbonate) containing 10% mouse serum, APC-conjugated anti-human CXCR4 antibody (1:500, Biolegend Catalog #306510) and PE-conjugated anti-human CKIT (1:100, Biolegend Catalog #313204) incubated for 30-45 minutes at 4° C. Following incubation, the single cell suspension was washed twice with FACS buffer prior to sorting, with centrifugation at 300 g, 4 min.

For cell sorting, stained cells were sorted for double-positive CXCR4/CKIT, using FACS Aria instrument (BD). Data analyses were performed with FlowJo software. Post-sort, CXCR4+/CKIT+ cells were seeded for aggregation at 5,000 cells per micro-cavitation chamber of Aggrewell™ 800 plates in basal DM supplemented with 100 nM retinoic acid, 5 ng/mL FGF9, 10 nM LDN193189, 1 μM CHIR99021, 100 ng/mL FGF1, 10 μM Y27632, and 10% Matrigel (v/v). Plates were centrifuged at 210 g for 4 min, followed by return to culture in a humidified incubator at 37° C., 5% $CO_2$. Temperature control is needed for managing Matrigel solidification.

On Day 8.5, aggregated cell masses were manually transferred to basal DM supplemented with 100 nM retinoic acid, 5 ng/mL FGF9, 10 nM LDN193189, 3 μM CHIR99021, 100 ng/mL FGF1, 1 ng/mL GDNF, 10 μM Y27632, and 10% Matrigel (v/v), using a wide bore pipette or a sieving spatula. To facilitate the generation of interconnected UB tissues from individual micromasses, Day 8.5 aggregates of Wolffian Duct progenitors were placed in close proximity to facilitate fusion with further culture. *Note that UB-UB connections can arise from juxtaposition of cells early in differentiation (as early as Day 6.5 sorted cells) or later stages of fully formed and maturing UBs.

On Day 10.5, maturing 3D aggregates were transitioned to basal DM supplemented with 100 nM retinoic acid, 3 μM CHIR99021, 10 nM LDN193189, 2 ng/mL GDNF, 100 ng/mL FGF1, and 10 μM Y27632. Connected tissues were preserved in transfer to retain early connection points for continued growth.

To promote the outgrowth and development of branching ureteric structures, Day 12.5 tissues were transitioned to transwell-based culture (Corning, Cat #3428). UB tissues were embedded in Branching Medium (comprising DMEM/F12 supplemented with 10% FBS, 250 units/mL of penicillin and streptomycin) supplemented with 100 nM retinoic acid, 100 ng/mL RSPO1, 2 ng/mL GDNF, 100 ng/mL FGF1, 30 ng/mL FGF7, 10 nM LDN193189, and 50% Matrigel (v/v), within transwells (apical). Culture medium was also added to each well (basal) to support tissue culture and branching morphogenesis, using the same medium as above but excluding Matrigel. Cultures were maintained with every other day feeds until the tissues reached mature UB structures at Day 20 to Day 24.5, when cultures were harvested for bioprinting and/or characterization. FIG. 1A shows an exemplary protocol for UB kidney tissue culture and characterization. FIG. 1B shows the media compositions and steps for generating the lumenized collecting duct.

Example 2. Recombination of Nephron Progenitors and UBs

On Day 18.5-24.5, UB tissues as described in Example 1 were manually extracted from 50% (v/v) Matrigel®-containing culture medium utilizing a wide bore p200 pipette with visual assistance of a stereoscope. As UB tissues were liberated, each sample was placed in basal branching media supplemented with 10 μM Y27632 until all samples had been collected. 20-50 UB tissues were collected for each syringe of bioink prepared. Tissues were spun for 2 minutes at 100 g, with the supernatant being aspirated. The pelleted material was then washed with 10 mL DPBS and centrifuged 2 minutes at 100 g. Following supernatant aspiration, residual Matrigel was next removed with the addition of 10 mL of 4° C. Corning Cell Recovery solution (Corning Catalog #354253), and incubated at 4° C. on a rotisserie tube rotator for 20 minutes. Following incubation, UB tissues were inspected under a microscope to ensure the Matrigel had been fully depolymerized, and then pelleted with a 1-minute spin at 100 g with the supernatant aspirated and replaced with 10 mL of basal branching media supplemented with 10 μM Y27632. UB tissues were fragmented by gentle passing through a blue, 22-gauge Nordson needle attached to a 3 mL syringe. Following each trituration, the extruded UB material was evaluated under a microscope to determine if all tissues had been fragmented (defined as the tip/stalk regions of the tissue being severed from the core mass of the tissue). Should whole tissues still be present, the trituration was performed until all tissues had been fragmented (maximum of 3 triturations to avoid transitioning the 3D cell material to a single cell state). Tip/stalk fragments, core masses, or a combination of both populations were then mixed into single cell suspension of day 7 posterior intermediate mesoderm cells produced in the nephron progenitor cell protocol (FIG. 1C) with adaption that a 1-hour pre-pulse with 5 μM CHIR99021 in E6 media was performed prior to harvesting day 7 monolayer cultures for bioprinting). The combined cell populations were pelleted for 3 minutes at 200 g. Following centrifugation, the supernatant was aspirated, and the pellet was resuspended in 1 mL of E6 media supplemented with 2% FBS (v/v). The freshly resuspend material was transferred to a 1.5 mL centrifuge tube and spun a 2nd time for 3 minutes at 200 g with the resulting supernatant being aspirated manually with a p1000 pipette. 50 μL E6 media supplemented with 2% FBS (v/v) was added back to the cell pellet to facilitate loosening of the cell pellet prior to direct transfer into a 100 μL Gastight syringe (Hamilton catalog #7656-05) with a 21-gauge needle (Hamilton catalog #7804-12). Loaded syringe was placed within the mechanical dispense tool (ASLS catalog #ASLS-0000227) prior to bioprint execution. Bioink extrusion was performed in a spatially defined location on 0.4 μM polyester membranes of 6-well Transwell permeable supports (Corning Costar catalog #3450) utilizing extrusion parameters as follows: 750 ms start delay, 10 mm/sec$^2$, acceleration with a final print speed of 0.6 mm/sec; mechanical dispense rate was 1250 steps/sec. Following print, all bioprinted tissues were maintained at the air-liquid interface with media refreshed every other day. For the day of print, and post-print days (PPD) 2 and 4, tissues were cultured in E6 media supplemented with 5% FBS (v/v), 100 ng/mL FGF9, 500 ng/mL heparin, 50 nM retinoic acid, 50 ng/mL RSPO1, 1 ng/mL GDNF, 50 ng/mL FGF1, 15 ng/mL FGF7, and 5 nM LDN193189. For PPD5 on, tissues were cultured in E6 media supplemented with 2% FBS (v/v), 50 nM retinoic acid, 50 ng/mL RSPO1, 1 ng/mL GDNF, 50 ng/mL FGF1, 15 ng/mL FGF7, and 5 nM LDN193189. From PPD5 to PPD14, media was changed every other day. Media composition post-recombination remained consistent with the minor adjustment that FGF9 and heparin were removed from the recipe. Tissues comprised of nephron and ureteric cell populations were cultured for 2 weeks at which point tissues were harvested for characterization. Samples for histological assessment were fixed overnight at 4° C. in 10% neutral buffered formalin, while samples for RNA were flash frozen in liquid nitrogen prior to RNA extraction.

Example 3. Characterization of UB Kidney Tissues

Figure 2:
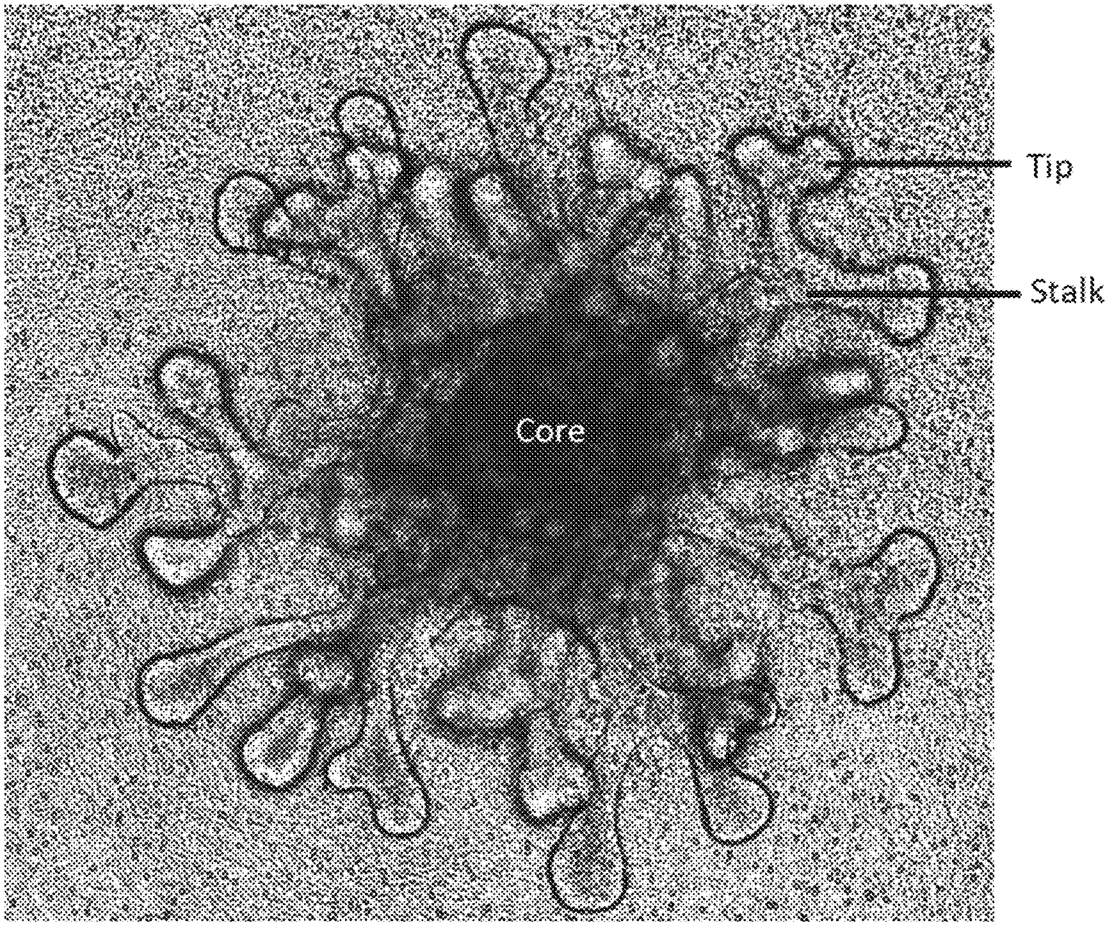
FIG. 2 shows an image of the morphology and structure of a human induced pluripotent stem cell-derived ureteric bud made by the methods provided herein. Arrows point to tips and stalks. The core is located in the center of the cell mass.
Figure 3:
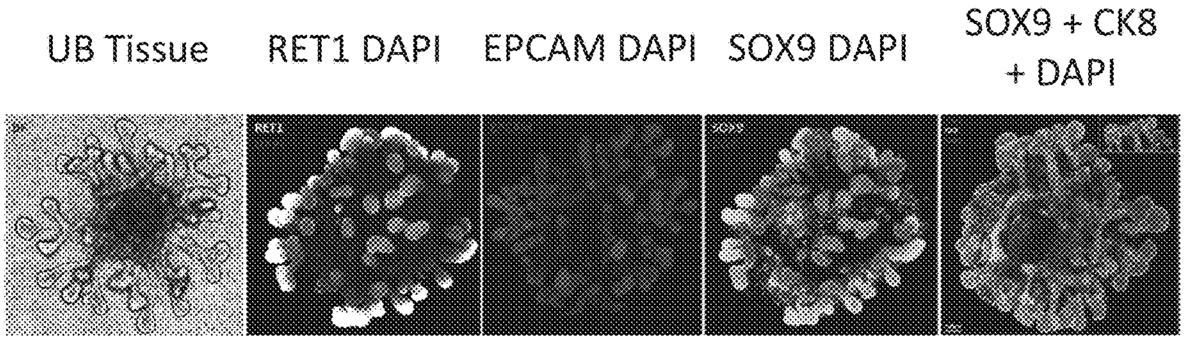
FIG. 3 shows microscopic images of single ureteric bud tissues derived from hiPSCs that express tip and stalk markers. Ureteric bud markers expressed include (from left to right) RET1, EPCAM, SOX9, and CK8.
Figure 4A:
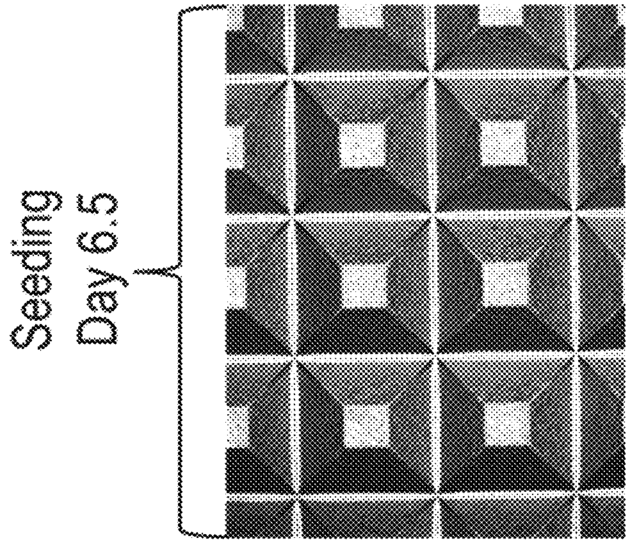
FIGS. 4A-4C show microscopic images of ureteric bud kidney tissue formation after FACS enrichment, deposition, and centrifugation.
Figure 4B:
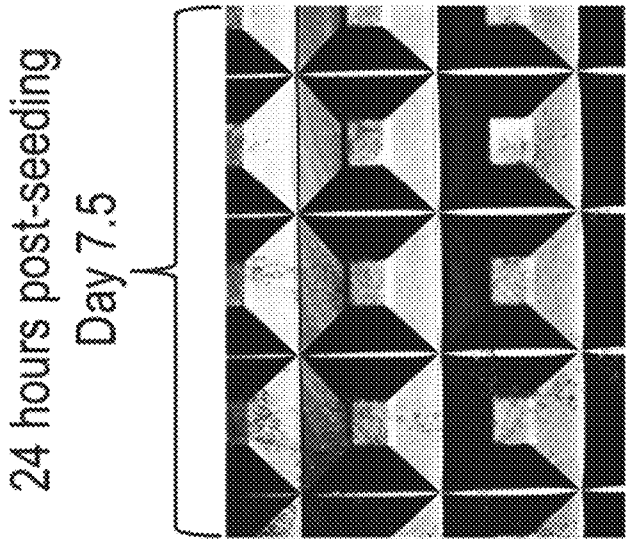
Figure 4C:
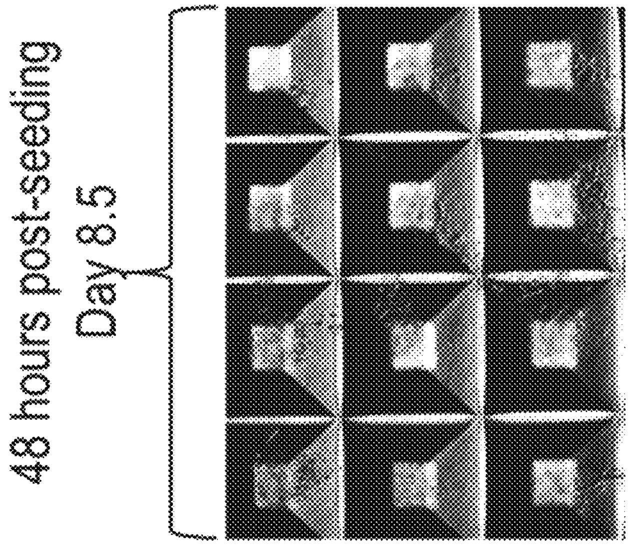

UB kidney tissues were made by the methods described in Example 1 to form whole UBs with a core comprising epithelial cells and renal stromal cells, tips, and stalks (FIG. 2). Single UB tissues derived from hiPSCs undergo branching morphogenesis and express tip and stalk markers, RET1, EPCAM, SOX9 and CK8 (FIG. 3). CXCR4+/CKIT+ cells in microwells following thaw and aggregation by brief centrifugation are shown in FIG. 4A, FIG. 4B, and FIG. 4C. Low speed centrifugation of UB cells and viscosity of Matrigel resulted in formation of a loose network of cells within and across microwells by 48 hours post-seeding.

Figure 5:
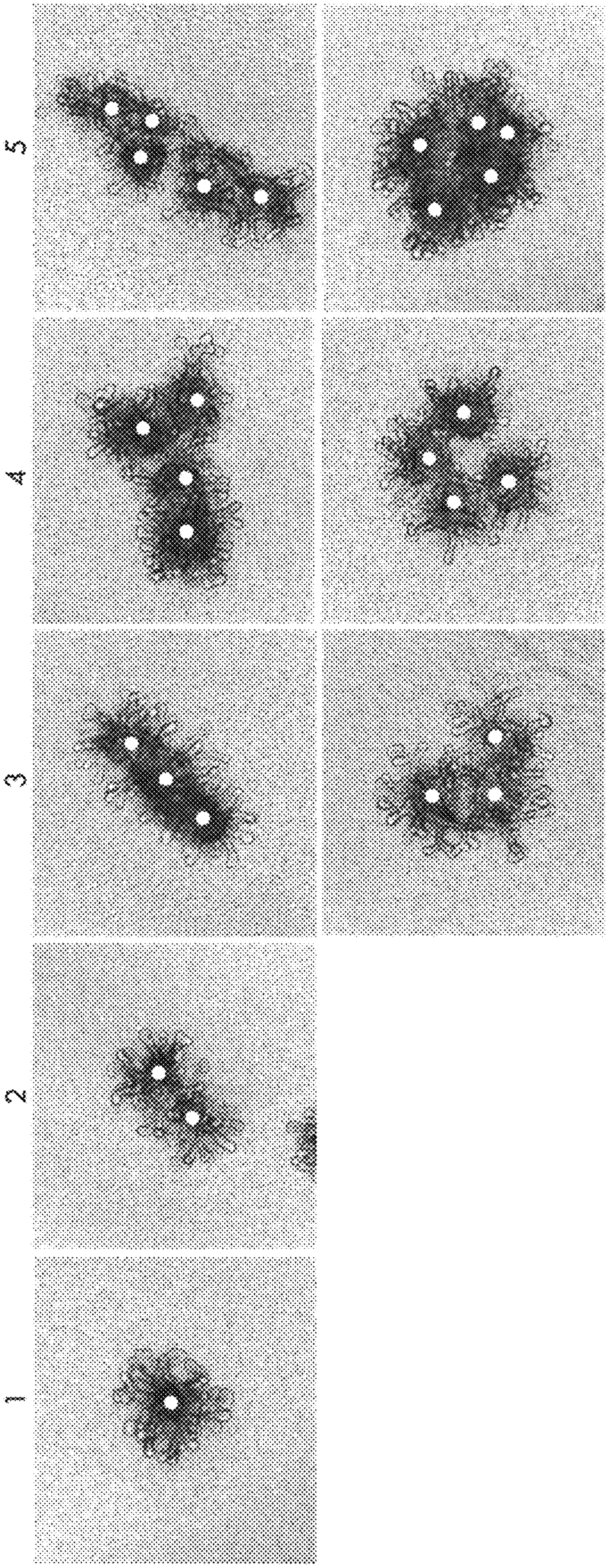
FIG. 5 shows images of individual UB tissues arranged in various patterns of increasing size at Day 22.5. Dots mark the center of each micro tissue.
Figure 6A:
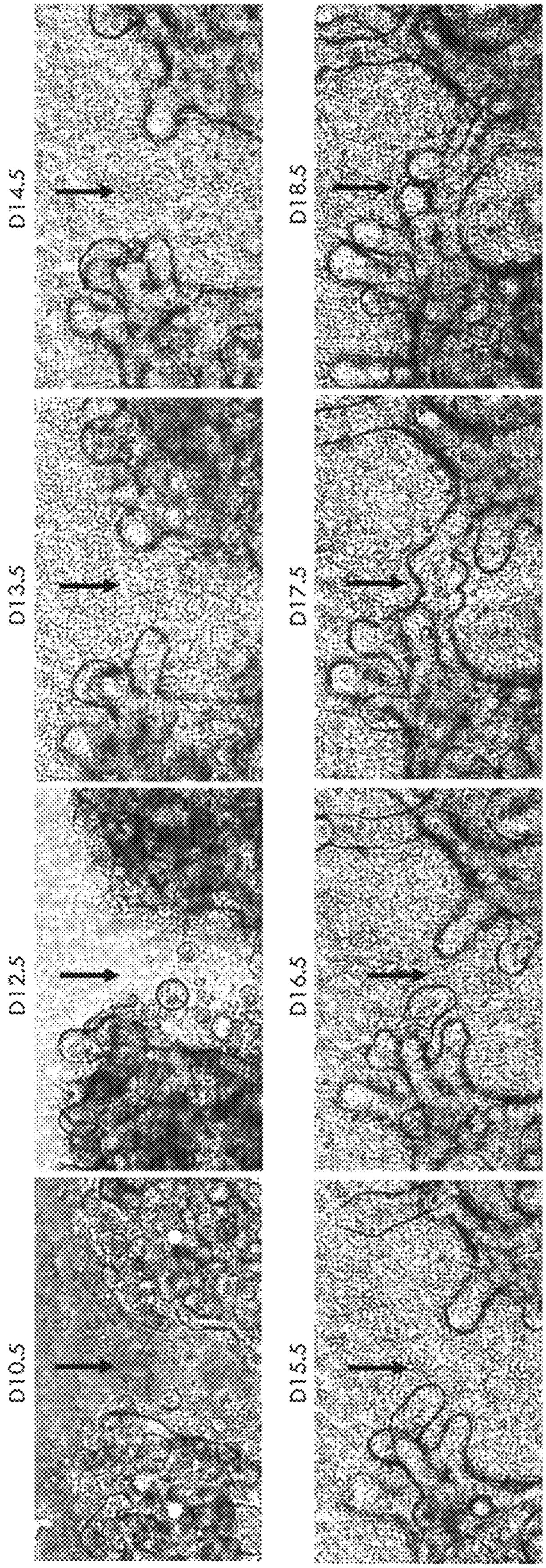
FIGS. 6A-6E show images of UB tissue fusion.
Figure 6B:
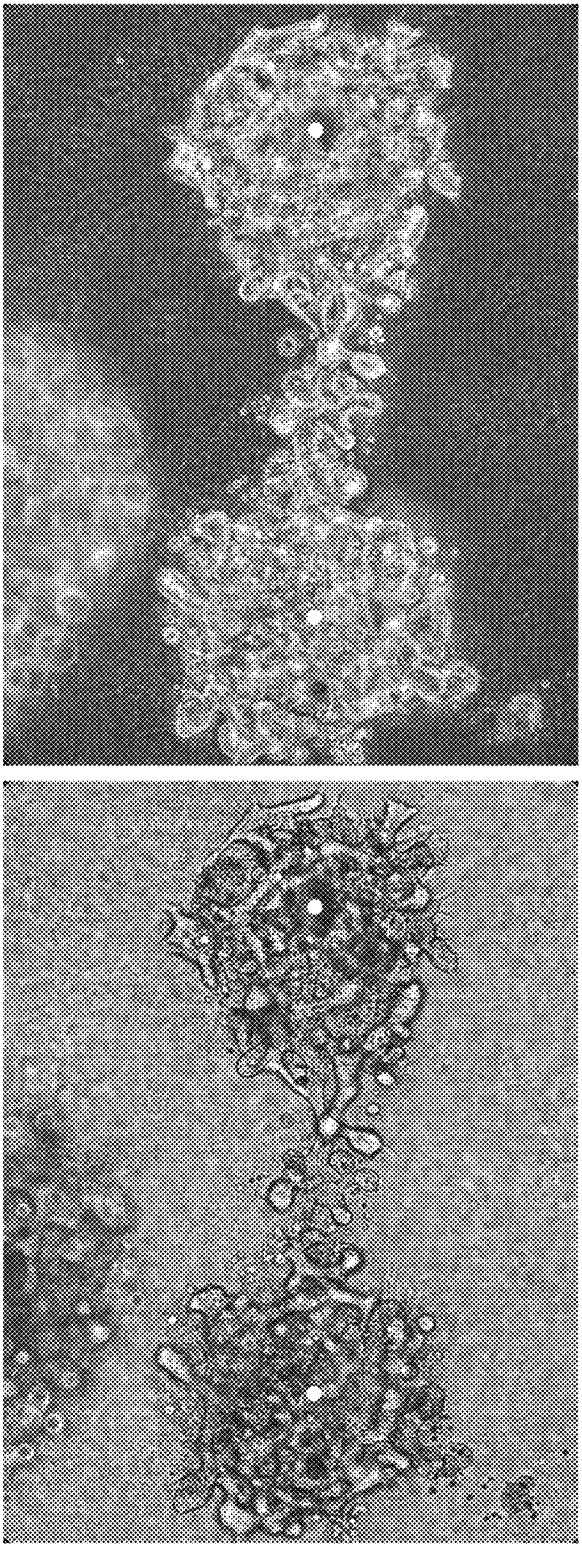
Figure 6C:
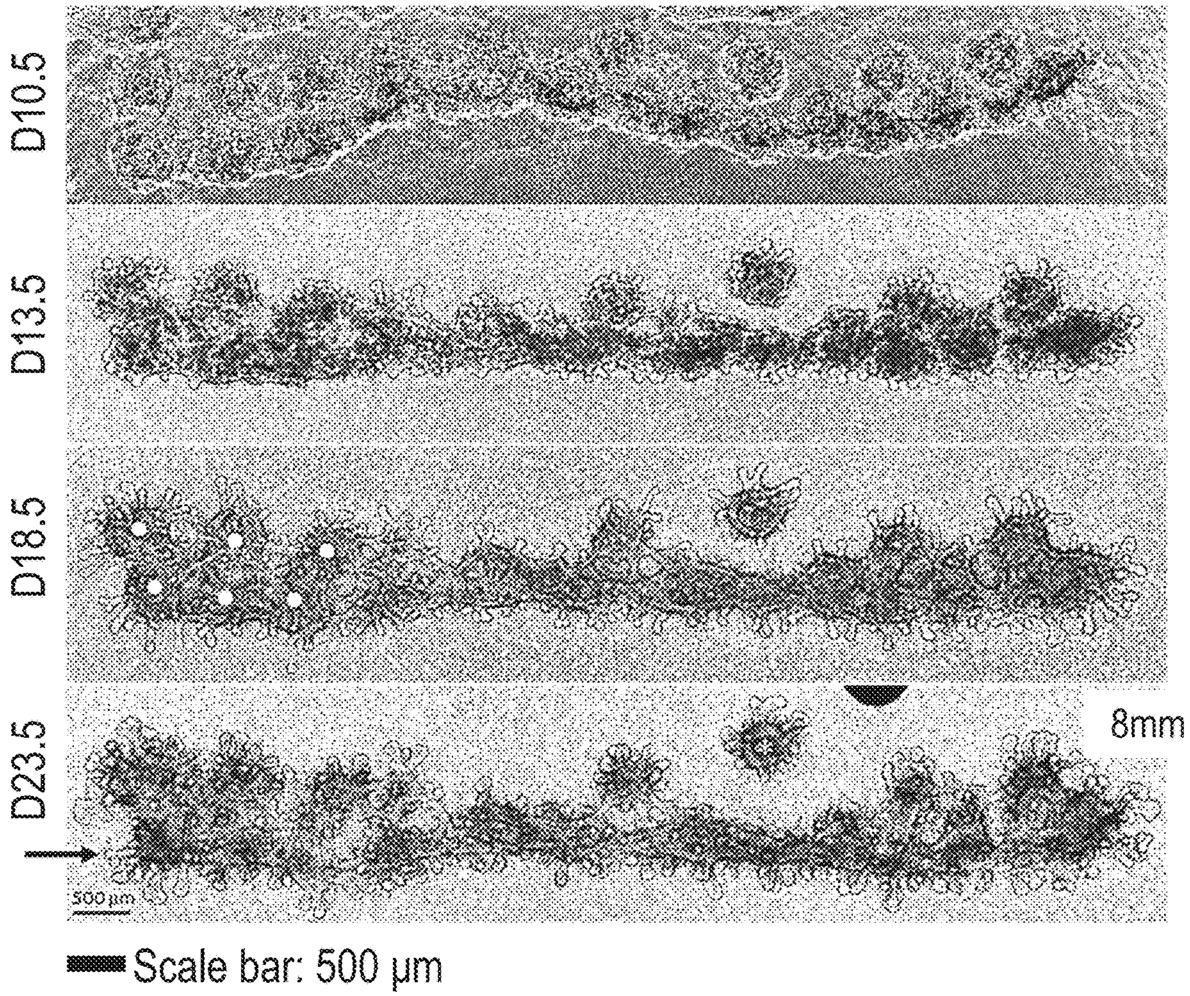
Figure 6D:
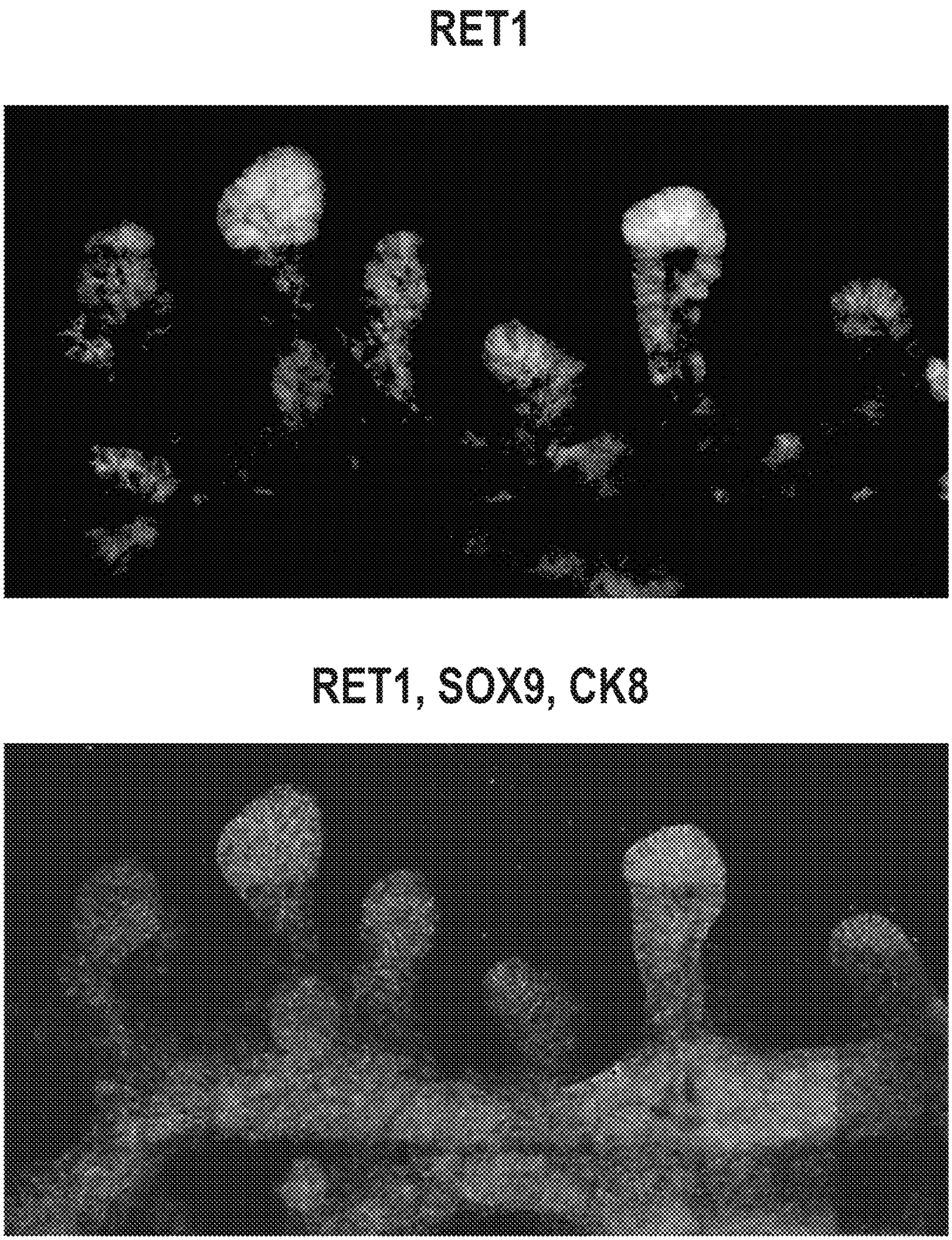
Figure 6E:
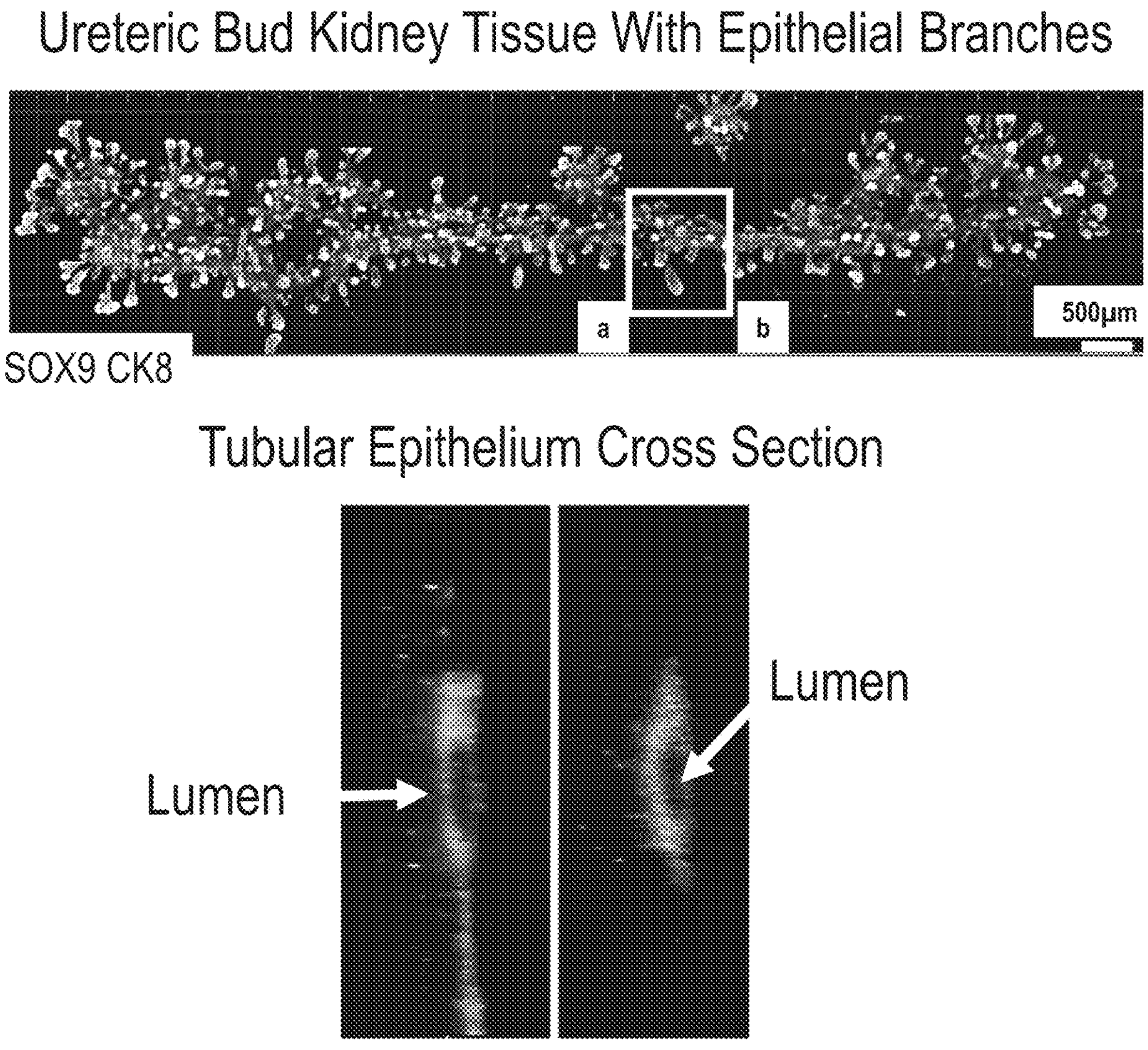

Individual UB tissues arranged in proximity to each other can form linear and group connections at day 22.5 (FIG. 5). UB tissues connect via fusion events between the tips of elongating epithelial branches. Tip fusion occurs between branches of adjacent tissues or within a single tissue (FIGS. 6A-6B). Large UB-only tissues can be generated when UB tissues are in close proximity and arranged in a continuum. Successive fusion events resulted in long contiguous tissues (Day 10.5-Day 23.5). Each tissue made multiple connections while undergoing branching morphogenesis. Fused tissues also remodeled over time to a form putative contiguous epithelium (FIG. 6C). A branched UB line maintains tip/stalk patterning and expressed marker genes enriched in the tip (SOX9, RET1) and stalk (CK8) (FIG. 6D). Intermittent lumens were detectable within a tubular epithelium. The size range for lumens were between about 25 and 75 millimeters (mm) in diameter and between about 25 and 250 mm long (FIG. 6E).

Example 4. Characterization of NPC-UB Kidney Tissues

Figure 7:
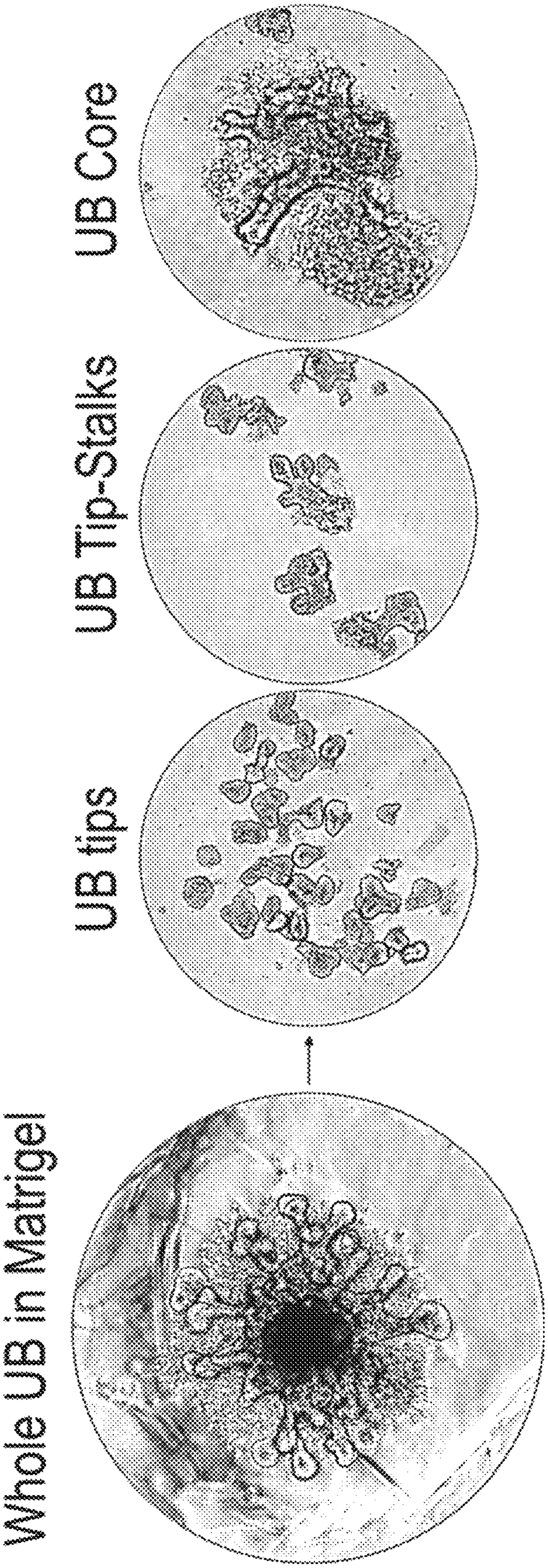
FIG. 7 shows images of extracted UBs from Matrigel culture and fragmentation into tip, stalk, and core components for recombination.
Figure 8:
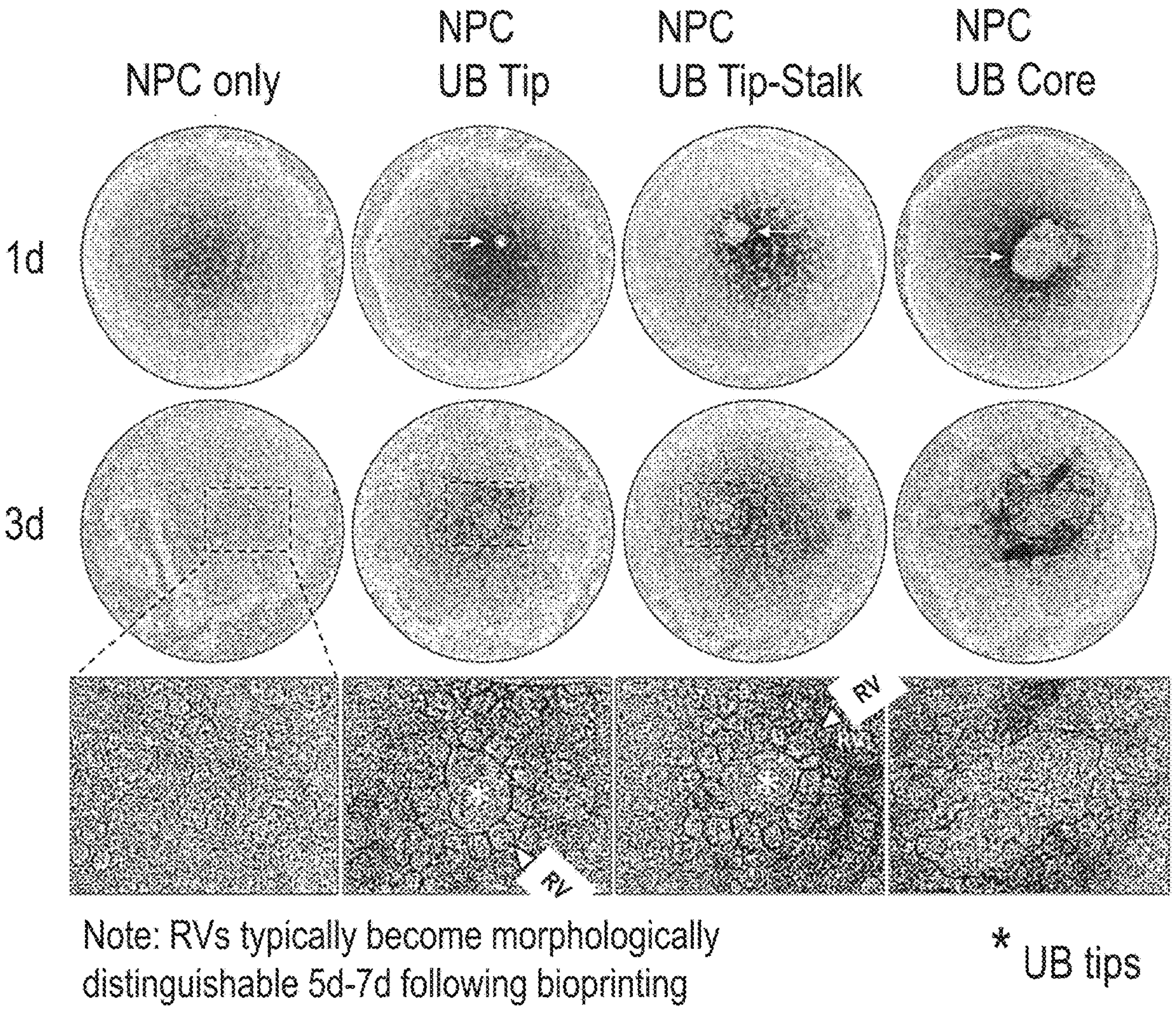
FIG. 8 shows images of kidney tissues that include nephron progenitor cells (NPCs) only; NPC with UB tips; NPCs with UB Tips and stalks; and NPCs with UB cores on day 1 (1 d) and day 3 (3 d) after recombination of the NPC and UB tissues.

UB kidney tissues were made by the methods described in Example 1 to form whole UBs with a core comprising epithelial cells and renal stromal cells, tips, and stalks (FIG. 2). The UB tissues were extracted from Matrigel suspension and then fragmented as shown in FIG. 7. Tips, stalks, and combinations of tips/stalks were isolated prior to recombination with nephron progenitor cells (NPCs). Kidney tissues containing UB tip preparations (Tip-only or Tip-Stalk) exhibited local acceleration of renal vesical induction and developed connection points between the two nephric/ureteric populations (FIG. 8).

Figure 9:
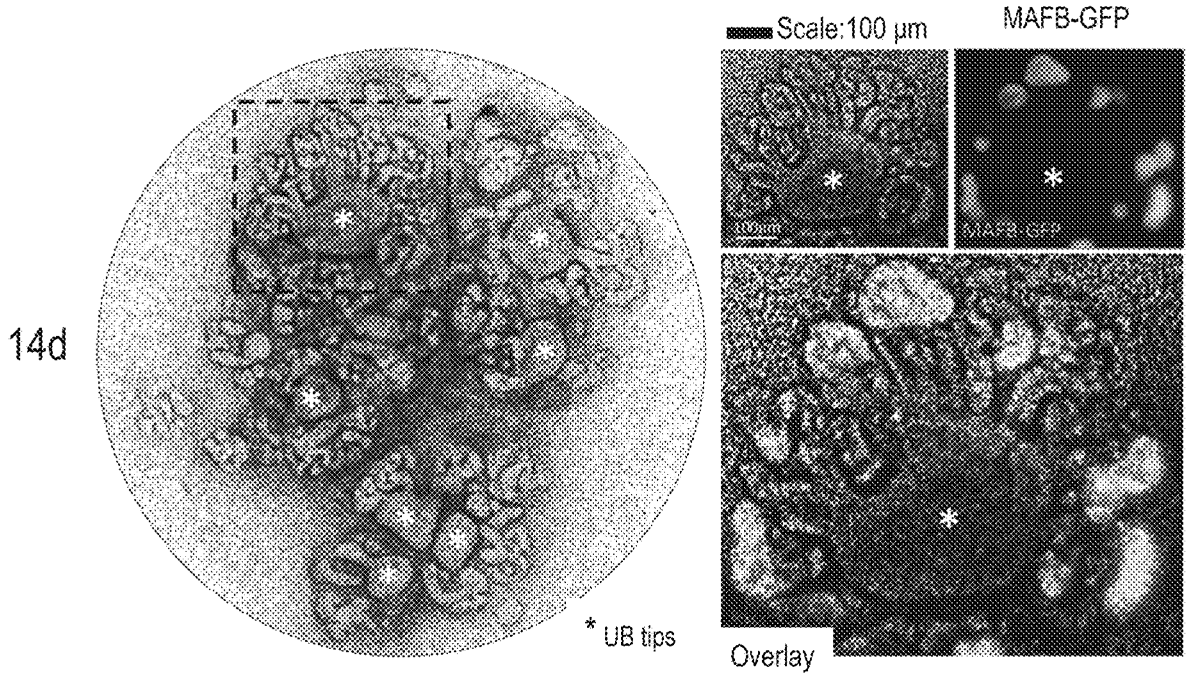
FIG. 9 shows an image of the combination of nephron and ureteric progenitor populations on day 14 after recombination with repeating units of centralized structure (UB-derived) with variable number of glomerular/tubular connections.
Figure 10:
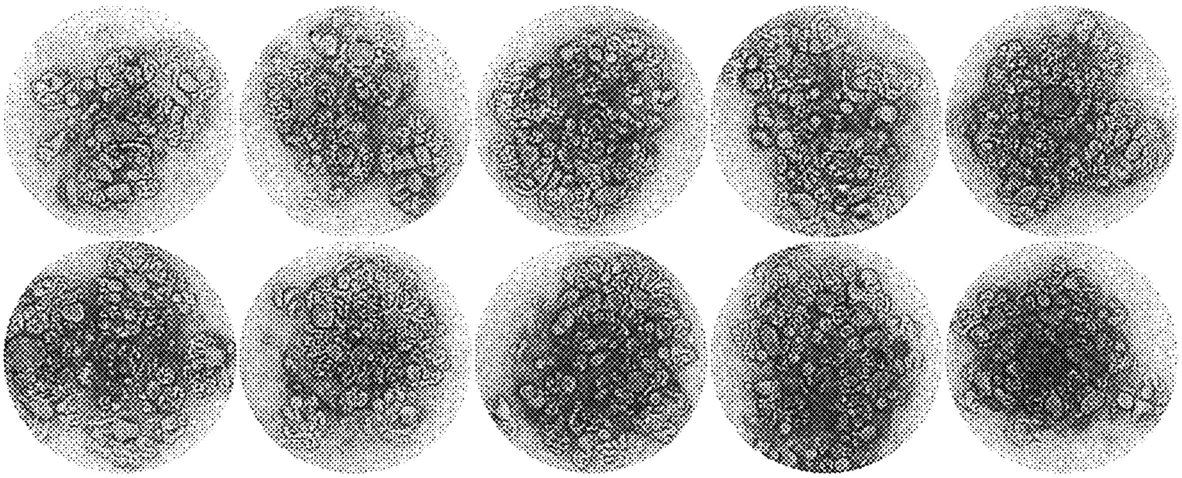
FIG. 10 shows images of the consistent morphology of recombined NPC and UB kidney tissues.
Figure 11A:
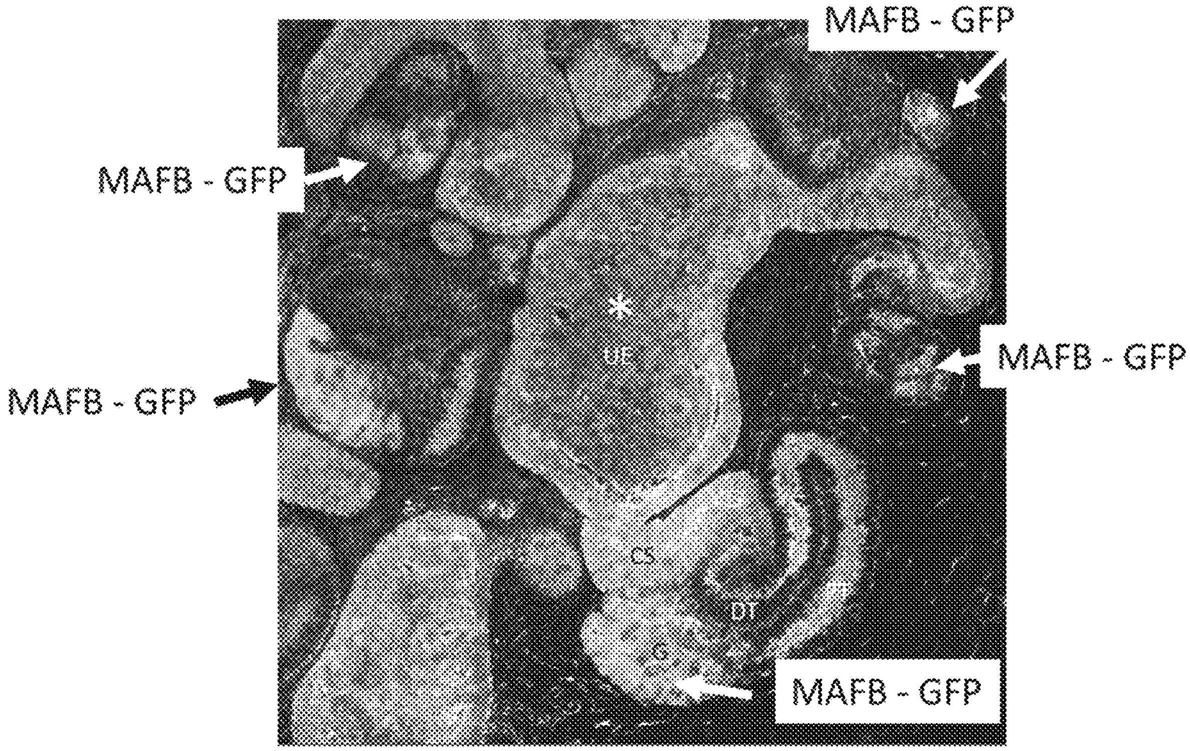
FIGS. 11A-11B shows images of the lumenal connections between segmented nephrons and ureteric epithelium.
Figure 11B:
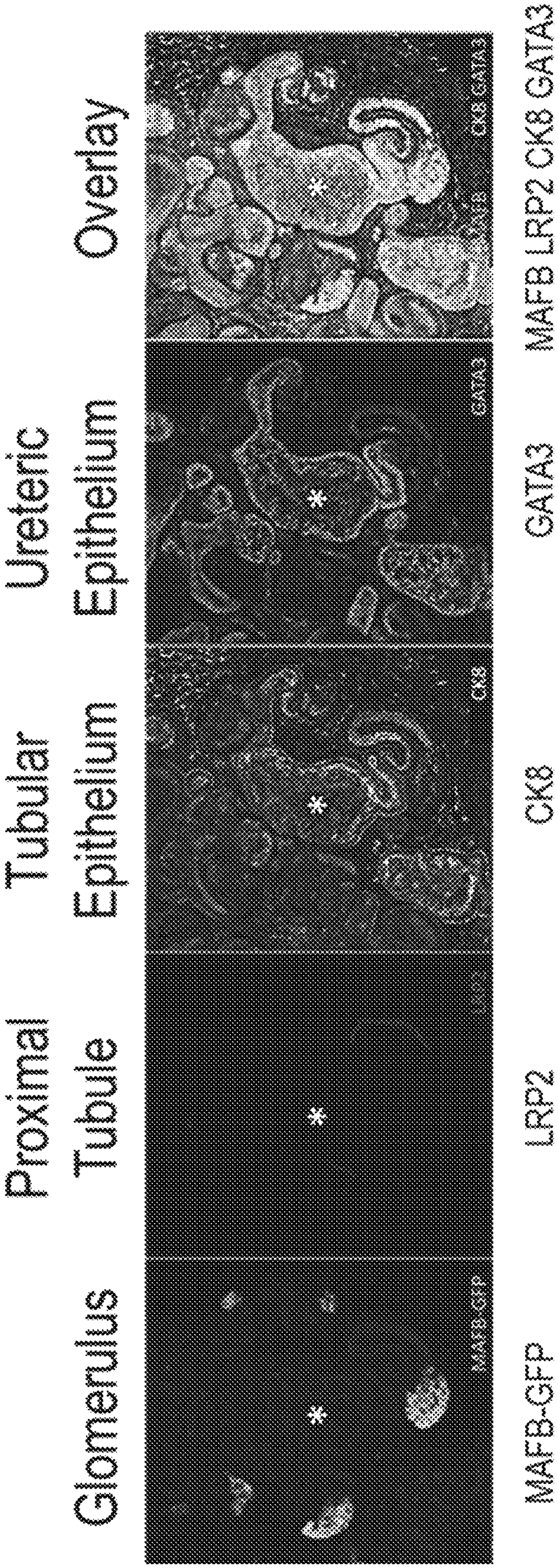

The nephron population was generated using a MAFB-GFP reporter line, which marks podocytes of glomeruli. The combination of nephron and ureteric progenitor populations produced tissues containing repeating units of centralized structure (UB-derived) (FIG. 9). The morphology of recombined tissues was highly consistent across samples generated by the methods described in Example 2. Lumenal connections between segmented nephrons and ureteric epithelium are shown in FIG. 10 and FIG. 11A. The ureteric epithelium also continued to undergo branching morphogenesis (reminiscent of development), with nephrons attached to bifurcated derivatives. Direct connections between segmented nephrons and ureteric epithelium (UE) were observed. One to three generations of UE branching was observed each with nephrons attached (FIG. 11B).

Figure 12A:
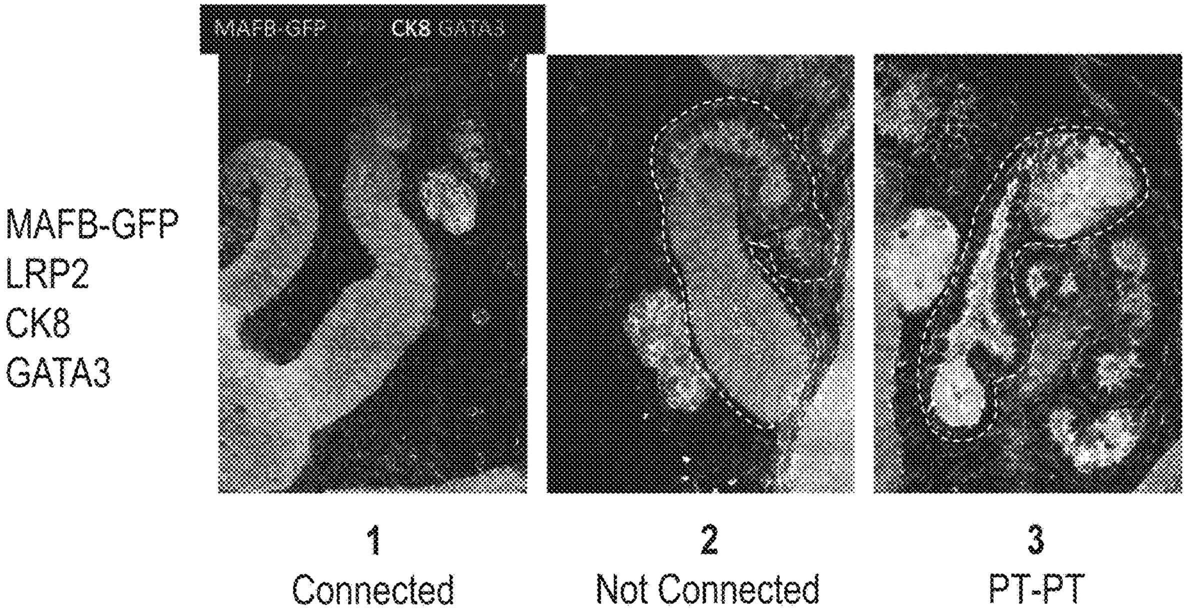
FIGS. 12A-12B show that nephrons in recombined tissues exhibit traceable connection to ureteric epithelium.
Figure 12B:
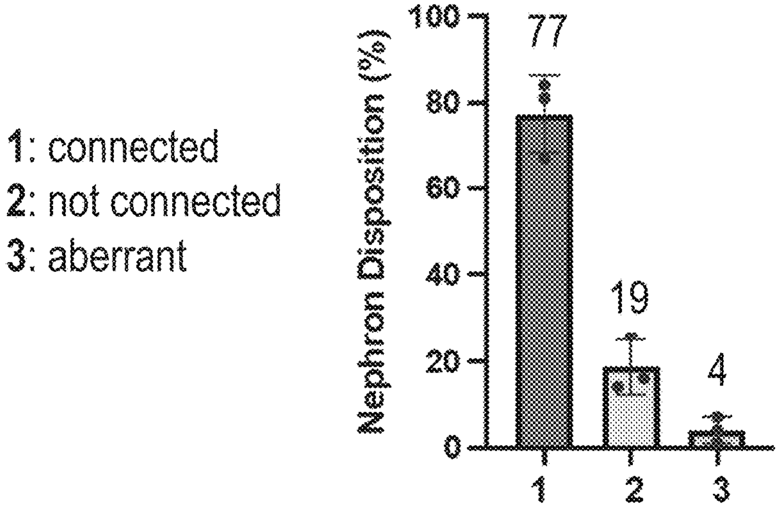

Connections between UB kidney tissues and NPCs were quantified by 3D mapping from confocal images of the UB-NPC kidney tissues. Tissues were categorized as connected, not-connected, or PT-PT. Exemplary images of each category are shown in FIG. 12A. Greater than 75% of nephrons in recombined tissues exhibited traceable connection to ureteric epithelium. 19% are either unable to be fully traced in 3D or not connected; 4% of samples had aberrant epithelial tubule-tubule connections (FIG. 12B).

Example 5. Wolffian Duct Progenitors Form an Epithelial Tube

Figure 18:
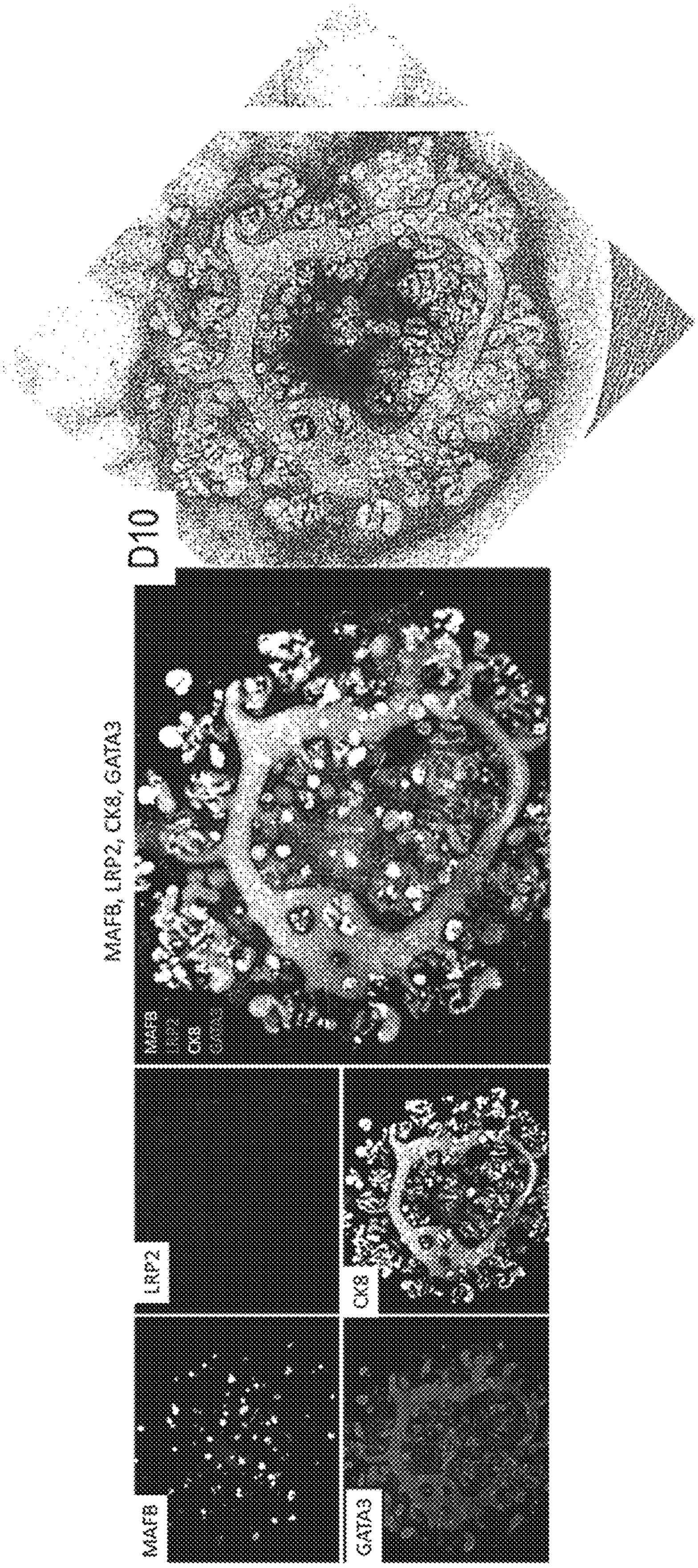
FIG. 18 shows images demonstrating that Wolffian duct progenitor cells form an epithelial tube with repeated points of connections with stem cell-derived nephrons (glomerulus and associated renal tubules) along its length. Markers include: MAFB, GATA3, LRP2, and CK8.

Wolffian duct progenitors were enriched for and used to generate recombined kidney tissues comprising stem cell-derived nephron progenitor cells as described in Examples 1 and 2. Wolffian duct progenitors on day 10 formed an epithelial tube with repeated points of connections with the stem cell-derived NPCs along its length (FIG. 18).

Example 6. Bioprinting Kidney Tissues

Figure 13:
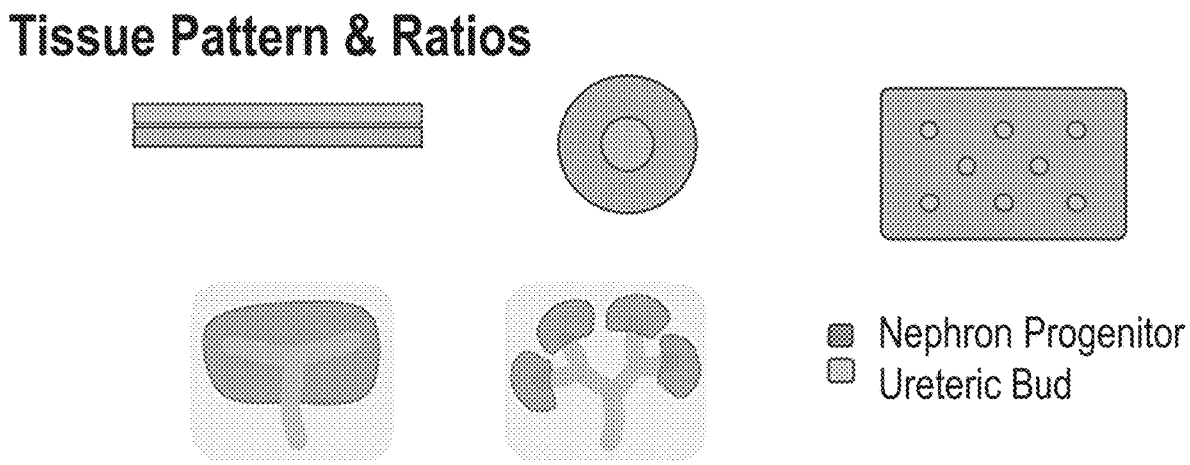
FIG. 13 shows exemplary patterns and ratio for cell bioprinting for generating kidney tissues.
Figure 14A:
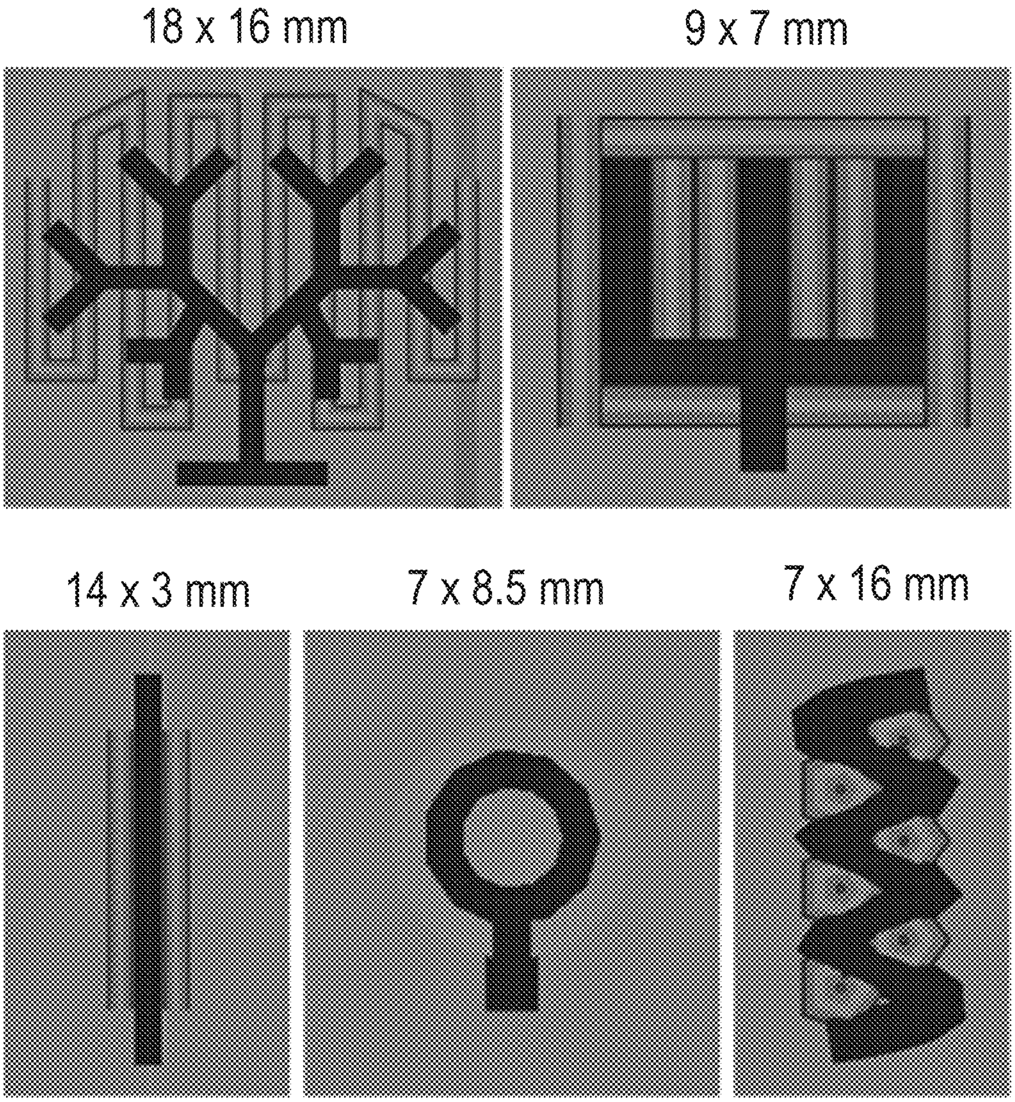
FIGS. 14A-14B shows exemplary kidney tissue bioprinting patterns with spatially controlled cellular populations.
Figure 14B:
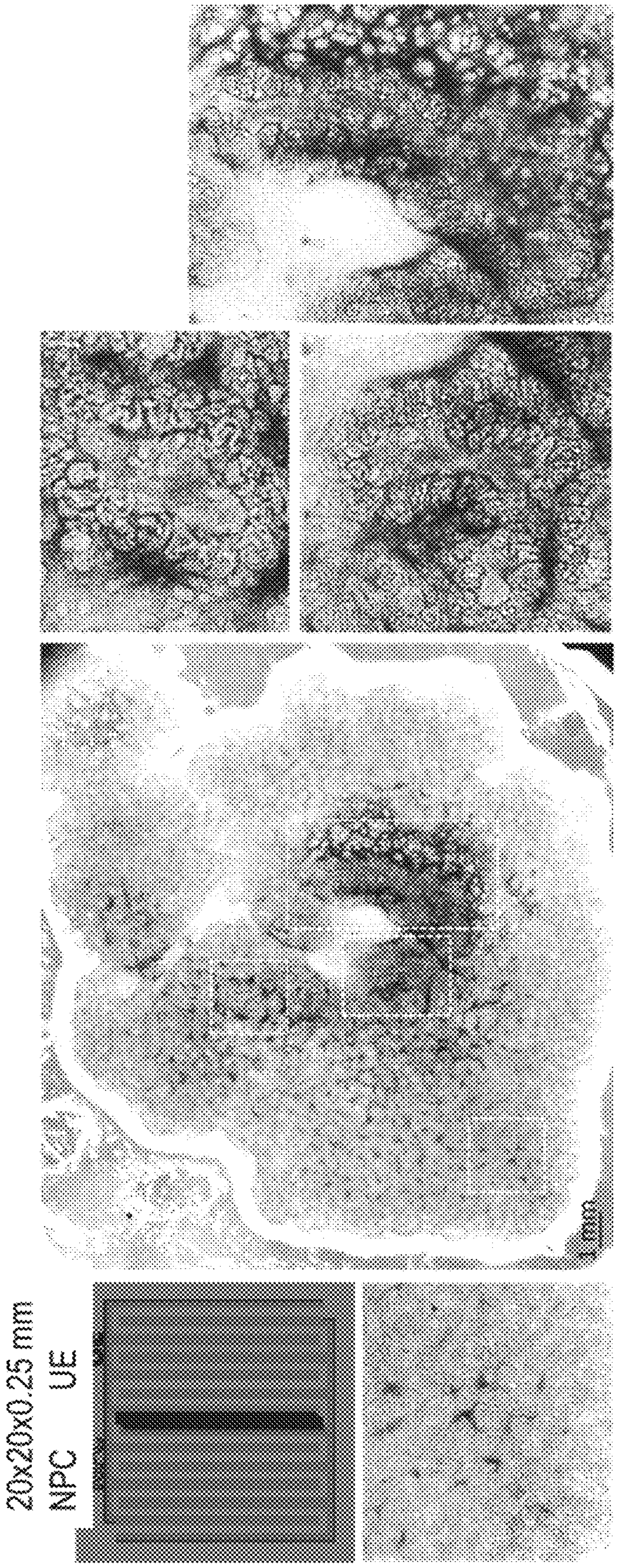

Bioprinting of spatially patterned tissues was performed using independent nephric and ureteric bioinks and a mixed bioink including both ureteric bud (UB) cells and nephron progenitor cells (NPCs). UB fragments and dissociated UBCs were printed. Various printing patterns were deposited include those shown in FIG. 13 and FIG. 14A. Bioprinted NPCs and UBs formed connections at the regions closest to the ureteric epithelium (FIG. 14B).

Figure 15:
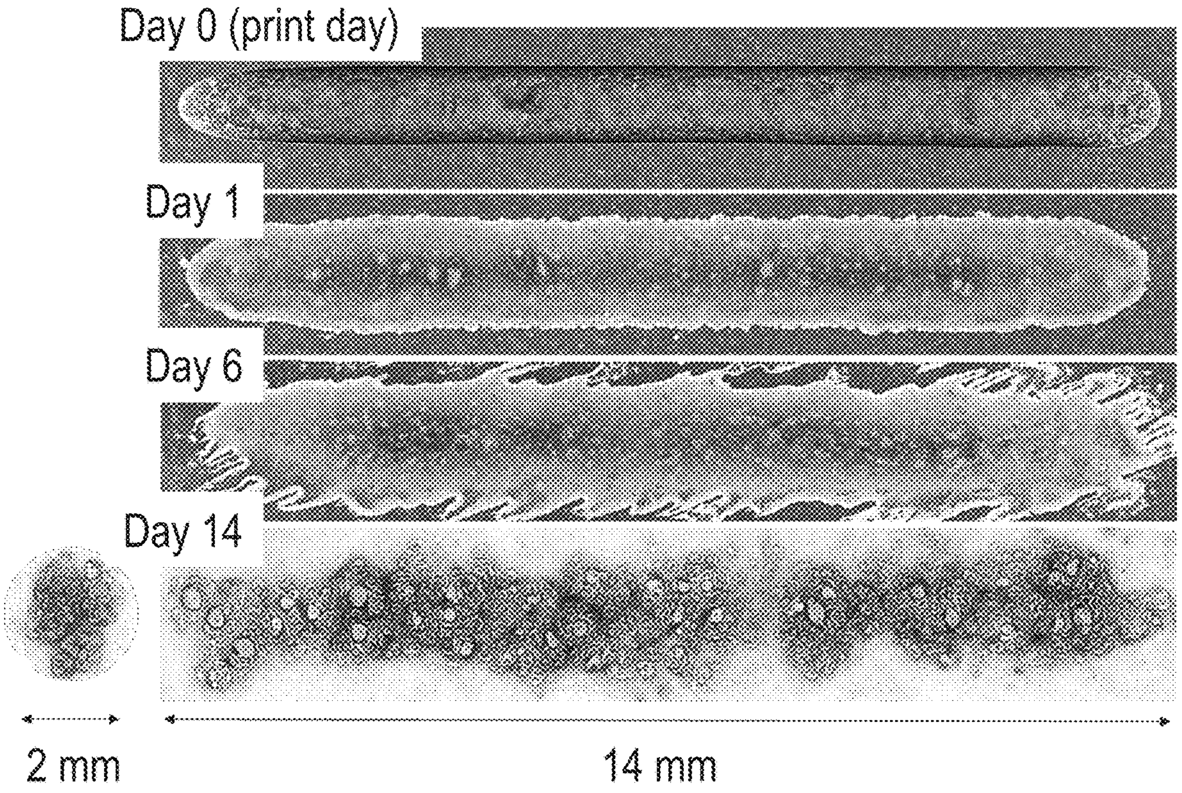
FIG. 15 shows images of scaled bioprinted kidney tissue over time from day 0 of printing to 14 days after printing as indicated from top to bottom. A 14 mm×2 mm linear pattern is shown relative to a circular tissue with 2 mm diameter.
Figure 16:
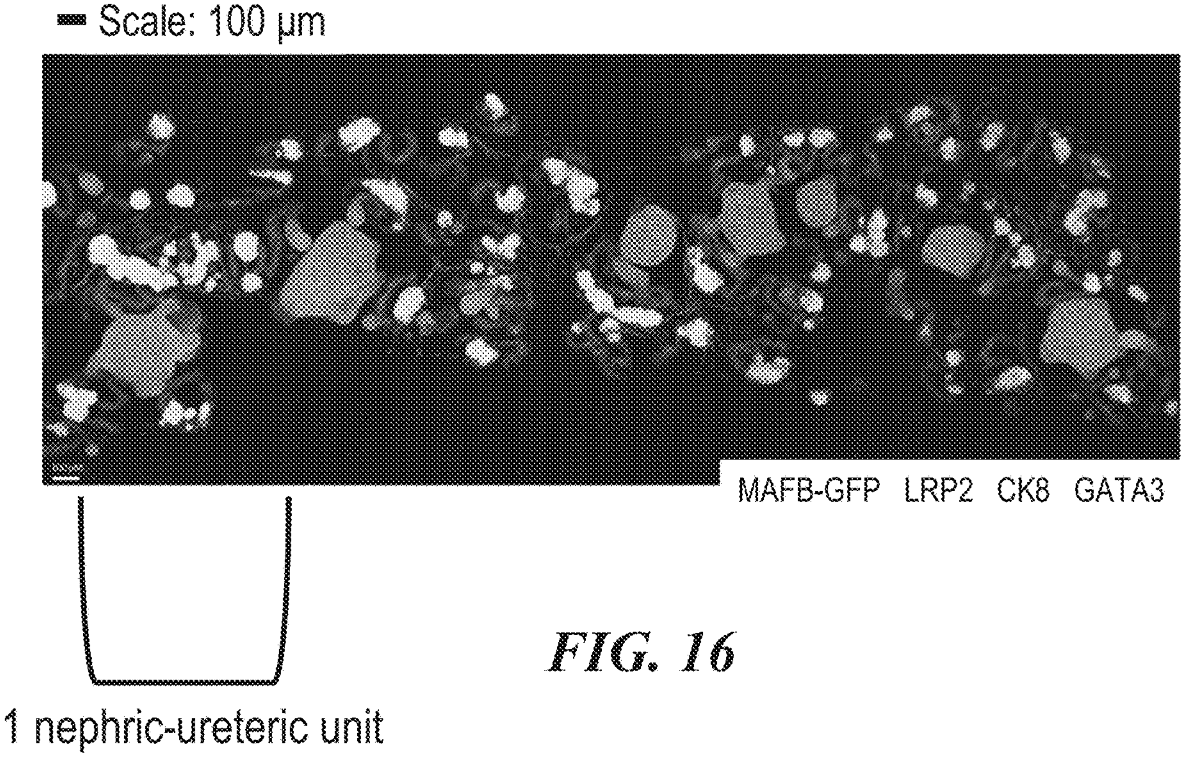
FIG. 16 shows and image of the repeating units of nephric-ureteric connections formed following bioprinting. 1 nephric-ureteric unit is approximately 700 microns in diameter.
Figure 17:
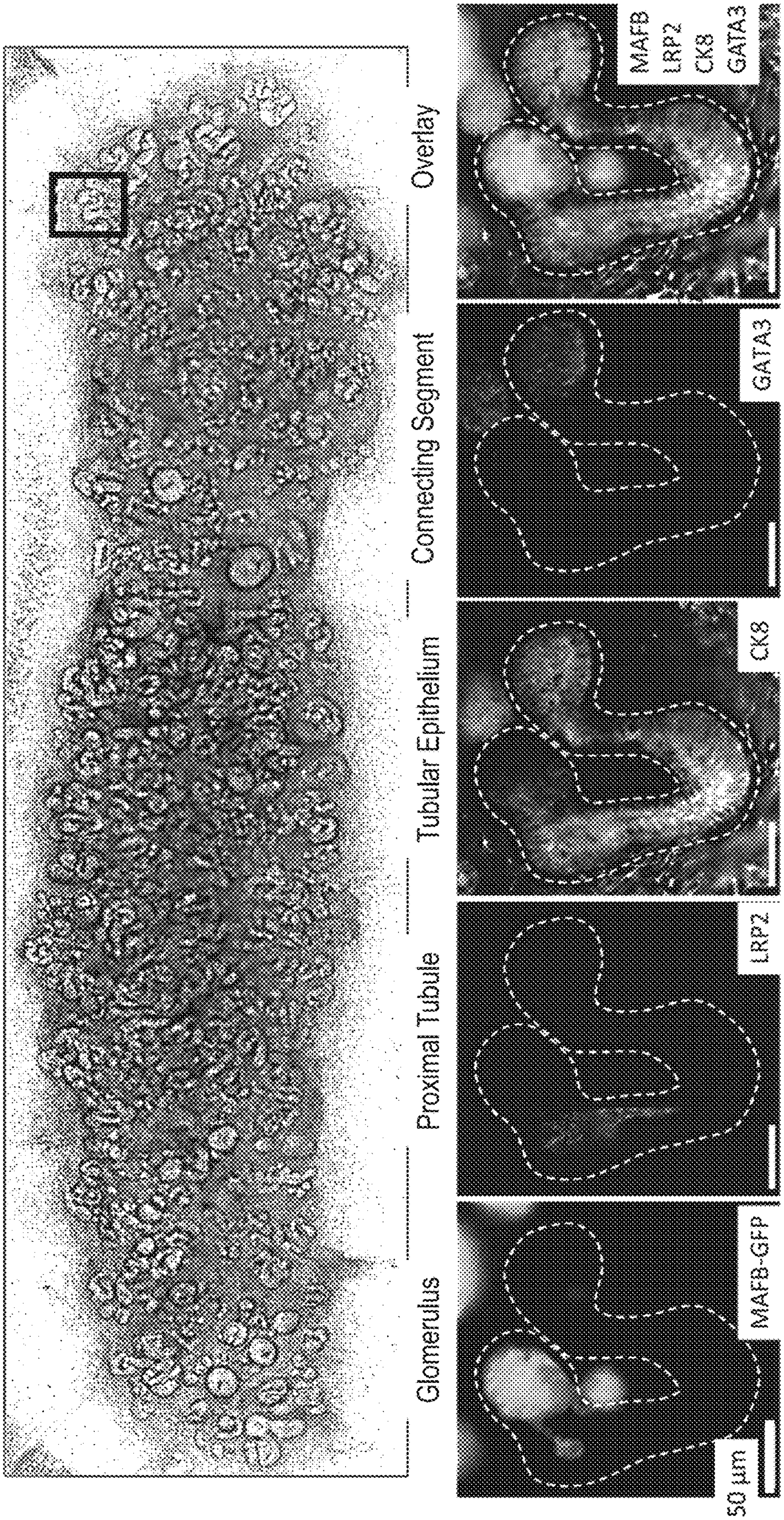
FIG. 17 shows images of a kidney tissue that includes structural and molecular characteristics of a glomerulus, a proximal tubule, a tubular epithelium, and a connecting segment.

Nephric and ureteric tissues (2 mm) were bioprinted in 14 mm by 2 mm linear tissue patches. Nephric-ureteric interactions scaled to larger tissues (FIG. 15). 3D tissue mapping by confocal microscopy and imaging confirmed repeating units of nephric-ureteric connections in larger tissue patches using the markers MAFB-GFP, LRP2, CK8, and GATA3 (FIG. 16). Kidney tissues bioprinted using a combination of differentially induced nephron progenitor cells and UB populations were also produced to form kidney tissues (FIG. 17).

Example 7. Method of Treating a Kidney Disease

Kidney tissues are produced according to the methods of Example 1 and Example 2. A patient with end-stage renal failure in need of renal replacement therapy and/or kidney transplant is selected by a physician to receive an engineered human kidney tissue by surgical procedure. The patient has a glomerular filtration rate below 15 ml/min/1.73 m2 and is receiving dialysis treatments.

The kidney tissues are surgically implanted and connected to the patient's own circulation by means of at least one arterial and at least one venous anastomosis, to establish blood flow to and from the implanted kidney tissue. The urine produced by the implanted kidney tissue is drained from the implanted tissue by means an engineered collecting duct, which is surgically connected to the patient's existing ureter, their bladder, or externalized via a urostomy. The patient is given immunosuppressive agents post-surgery and kidney function is evaluated. The patient is expected to have an improved GFR over 15 about 2 weeks post-surgery and can discontinue dialysis treatment when GFR reaches 20.

What is claimed is:

1. A method for generating a kidney tissue having a spatially-controlled 3-dimensional (3D) tubular architecture in vitro, the method comprising:

a) enriching a population of Wolffian duct progenitor cells for CXCR4 and cKit expressing Wolffian duct progenitor cells to form aggregates of CXCR4 and cKit expressing Wolffian duct progenitor cells;

b) culturing the aggregates of the CXCR4 and cKit expressing Wolffian duct progenitor cells in a first cell culture medium comprising: a retinoic acid, a fibroblast growth factor (FGF), an ALK inhibitor, a Rho kinase (ROCK) inhibitor, a WNT pathway activator and an extracellular matrix;

c) spatially arranging the aggregates of CXCR4- and cKit-expressing Wolffian duct progenitor cells in a sequential configuration and in a proximity sufficient to form fused tissues that are contiguously fused from at least one connecting point; and d) culturing the fused tissues in a branching medium comprising: a serum, a retinoic acid, a Wnt pathway activator, a fibroblast growth factor (FGF), a glial-derived neurotrophic factor (GDNF), an ALK inhibitor, and the extracellular matrix, thereby forming a kidney tissue having a spatially-controlled 3D tubular architecture, wherein the kidney tissue upon contact with a fluid facilitates fluid flow through the spatially-controlled 3D tubular architecture.

2. The method of claim 1, wherein the Wolffian duct progenitor cells are differentiated from human induced pluripotent stem cells.

3. The method of claim 1, wherein the Wolffian duct progenitor cells further express PAX2, EMX2, LHX1, RET1, HOXB7, or a combination thereof.

4. The method of claim 1, wherein the generating comprises aggregating the Wolffian duct progenitor cells using centrifugation and differentiating the aggregated Wolffian duct progenitor cells in a suspension culture.

5. The method of claim 1, wherein the generating further comprises enriching the Wolffian duct progenitor cells for CXCR4 and cKit expressing Wolffian duct progenitor cells.

6. The method of claim 1, wherein the generating comprises contacting the Wolffian duct progenitor cells with a cell culture medium comprising: retinoic acid, fibroblast growth factor 9 (FGF9), LDN193189, CHIR99021, fibroblast growth factor 1 (FGF1), glial-derived neurotrophic factor 1 (GDNF), Y27632, and a solubilized basement membrane preparation extracted from Engelbreth-Holm-Swarm (EHS) mouse sarcoma.

7. The method of claim 1, wherein the arranging comprises bioprinting the plurality of kidney tissues.

8. The method of claim 1, wherein the at least one connecting point of the fused tissues comprise:

(a) two or more tips of adjacent kidney tissues; or (b) two or more stalks of adjacent kidney tissues; or (c) a tip and a stalk of two adjacent kidney tissues.

9. A method of generating an in vitro-differentiated human kidney tissue, the method comprising:

(a) differentiating a population of human induced pluripotent stem cell (iPSC) aggregates to a population of Wolffian duct progenitor cell aggregates;

(b) isolating and enriching the Wolffian duct progenitor cells expressing CXCR4 and cKit to form Wolffian duct progenitor cell aggregates;

(c) contacting the Wolffian duct progenitor cell aggregates formed in (b) with a first cell culture medium, wherein the first cell medium comprises: retinoic acid, fibroblast growth factor 9 (FGF9), LDN193189, CHIR99021, fibroblast growth factor 1 (FGF1), glial-derived neurotrophic factor (GDNF), Y27632, and an extracellular matrix; and (d) culturing the Wolffian duct progenitor cell aggregates for at least 48 hours in static culture conditions in said first cell medium;

(e) arranging the Wolffian duct progenitor cell aggregates in a sequential configuration and in a proximity sufficient to form fused tissues that are contiguously fused from at least one connecting point; and (f) culturing the fused tissues in a branching culture medium for at least 48 hours to form an in vitro-differentiated human kidney tissue, wherein the branching culture medium comprises serum, retinoic acid, RSPO1, a neurotrophic factor, a fibroblast growth factor, a bone morphogenetic pathway inhibitor, an extracellular matrix, thereby generating an in vitro-differentiated human kidney tissue.

10. The method of claim 1, wherein the WNT pathway activator comprises CHIR98014, CHIR98024, CHIR99021, 2,4'-dibromoacetophenone, dihydronarwedine, or a combination thereof.

11. The method of claim 1, wherein the FGF comprises FGF1, FGF7, FGF9, or a combination thereof.

* * * * *